(12) United States Patent
Min et al.

(10) Patent No.: US 8,442,634 B2
(45) Date of Patent: May 14, 2013

(54) SYSTEMS AND METHODS FOR CONTROLLING VENTRICULAR PACING IN PATIENTS WITH LONG INTER-ATRIAL CONDUCTION DELAYS

(75) Inventors: Xiaoyl Min, Thousand Oaks, CA (US);
Duane Tsutsui, West Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 1144 days.

(21) Appl. No.: 12/328,605

(22) Filed: Dec. 4, 2008

(65) Prior Publication Data

US 2010/0145405 A1    Jun. 10, 2010

(51) Int. Cl.
*A61N 1/00*    (2006.01)

(52) U.S. Cl.
USPC ............................................ 607/25

(58) Field of Classification Search ............ 607/25
See application file for complete search history.

(56) References Cited

U.S. PATENT DOCUMENTS

| | | | |
|---|---|---|---|
| 4,712,555 | A | 12/1987 | Thornander et al. |
| 4,788,980 | A | 12/1988 | Mann et al. |
| 4,928,688 | A | 5/1990 | Mower |
| 4,940,052 | A | 7/1990 | Mann et al. |
| 4,944,298 | A | 7/1990 | Sholder |
| 5,086,774 | A | 2/1992 | Duncan |
| 5,174,289 | A | 12/1992 | Cohen |
| 5,179,949 | A | 1/1993 | Chirife |
| 5,391,189 | A | 2/1995 | van Krieken et al. |
| 5,466,254 | A | 11/1995 | Helland |
| 5,476,483 | A | 12/1995 | Bornzin et al. |
| 5,643,327 | A | 7/1997 | Dawson et al. |
| 5,741,308 | A | 4/1998 | Sholder |
| 5,749,906 | A | 5/1998 | Kieval et al. |
| 5,800,465 | A | 9/1998 | Thompson et al. |
| 5,814,077 | A | 9/1998 | Sholder et al. |
| 5,814,089 | A | 9/1998 | Stokes et al. |

(Continued)

FOREIGN PATENT DOCUMENTS

| | | |
|---|---|---|
| EP | 0494487 B1 | 1/1996 |
| EP | 1199085 B1 | 4/2002 |

(Continued)

OTHER PUBLICATIONS

NonFinal Office Action, mailed Nov. 17, 2005: Related U.S. Appl. No. 10/703,070.

(Continued)

*Primary Examiner* — Christopher D Koharski
*Assistant Examiner* — Philip Edwards

(57) ABSTRACT

Techniques are provided for use by implantable medical devices for controlling ventricular pacing. In one example, optimal atrio-ventricular and interventricular pacing delay values are determined for pacing the heart of the patient based, in part, on a measured inter-atrial conduction delay. Atrio-ventricular conduction delays are then measured within the patient. The atrio-ventricular pacing delays are compared with the measured atrio-ventricular conduction delays. If the atrio-ventricular pacing delays are less than the measured atrio-ventricular conduction delays, biventricular pacing is delivered using the atrio-ventricular pacing delay and the interventricular pacing delay. However, if the atrio-ventricular pacing delays are not less than the corresponding atrio-ventricular conduction delays, as can occur if the inter-atrial conduction delay is large, then alternative pacing regimes are selectively enabled, such as monoventricular pacing in the chamber having the longer conduction delay value, biventricular pacing with negative hysteresis, or biventricular pacing with pacing delays reduced using predetermined offset values.

13 Claims, 32 Drawing Sheets

U.S. PATENT DOCUMENTS

| | | | |
|---|---|---|---|
| 5,873,895 | A | 2/1999 | Sholder et al. |
| 6,122,546 | A | 9/2000 | Sholder et al. |
| 6,141,588 | A | 10/2000 | Cox et al. |
| 6,144,880 | A | 11/2000 | Ding et al. |
| 6,285,907 | B1 | 9/2001 | Kramer et al. |
| 6,314,323 | B1 | 11/2001 | Ekwall |
| 6,360,127 | B1 | 3/2002 | Ding et al. |
| 6,411,848 | B2 | 6/2002 | Kramer et al. |
| 6,424,865 | B1 | 7/2002 | Ding |
| 6,473,645 | B1 | 10/2002 | Levine |
| 6,473,647 | B1 | 10/2002 | Bradley |
| 6,496,730 | B1 | 12/2002 | Kleckner et al. |
| 6,567,700 | B1 | 5/2003 | Turcott et al. |
| 6,606,516 | B2 | 8/2003 | Levine |
| 6,622,040 | B2 | 9/2003 | Ding et al. |
| 6,668,194 | B2 | 12/2003 | VanHout |
| 6,711,439 | B1 | 3/2004 | Bradley et al. |
| 6,751,503 | B1 | 6/2004 | Kroll |
| 6,754,530 | B2 | 6/2004 | Bakels et al. |
| 6,804,555 | B2 | 10/2004 | Warkentin |
| 6,934,586 | B2 | 8/2005 | Struble et al. |
| 6,959,214 | B2 | 10/2005 | Pape et al. |
| 7,181,284 | B2 | 2/2007 | Burnes et al. |
| 7,203,541 | B2 | 4/2007 | Sowelam et al. |
| 7,248,925 | B2 * | 7/2007 | Bruhns et al. .................. 607/25 |
| 7,555,340 | B2 * | 6/2009 | Dong et al. ........................ 607/9 |
| 2001/0016759 | A1 | 8/2001 | Kramer et al. |
| 2001/0031993 | A1 | 10/2001 | Salo et al. |
| 2002/0049478 | A1 | 4/2002 | Ding et al. |
| 2002/0062139 | A1 | 5/2002 | Ding |
| 2002/0077559 | A1 | 6/2002 | Ding et al. |
| 2002/0161410 | A1 | 10/2002 | Kramer et al. |
| 2003/0004548 | A1 | 1/2003 | Warkentin |
| 2003/0014084 | A1 | 1/2003 | VanHout |
| 2003/0060851 | A1 | 3/2003 | Kramer et al. |
| 2003/0130702 | A1 | 7/2003 | Kramer et al. |
| 2003/0195580 | A1 | 10/2003 | Bradley et al. |
| 2003/0204212 | A1 | 10/2003 | Burnes et al. |
| 2004/0133246 | A1 | 7/2004 | Ding et al. |
| 2004/0147966 | A1 | 7/2004 | Ding et al. |
| 2004/0158293 | A1 | 8/2004 | Yonce et al. |
| 2004/0193223 | A1 | 9/2004 | Kramer et al. |
| 2004/0220635 | A1 | 11/2004 | Burnes |
| 2005/0090870 | A1 | 4/2005 | Hine et al. |
| 2005/0149138 | A1 | 7/2005 | Min et al. |
| 2006/0276848 | A1 | 12/2006 | Min et al. |

FOREIGN PATENT DOCUMENTS

| | | |
|---|---|---|
| EP | 1234597 A2 | 8/2002 |
| WO | 9958191 | 11/1999 |
| WO | 02051495 A2 | 7/2002 |
| WO | 03037427 A1 | 5/2003 |
| WO | 2005039690 A1 | 5/2005 |

OTHER PUBLICATIONS

Final Office Action, mailed Jul. 31, 2006: Related U.S. Appl. No. 10/703,070.
Advisory Action, mailed Oct. 20, 2006: Related U.S. Appl. No. 10/703,070.
NonFinal Office Action, mailed Apr. 10, 2007: Related U.S. Appl. No. 10/703,070.
Final Office Action, mailed Jun. 26, 2008: Related U.S. Appl. No. 10/703,070—Now Abandoned.
NonFinal Office Action, mailed Apr. 10, 2007: Related U.S. Appl. No. 10/974,123.
Final Office Action, mailed Jul. 9, 2008: Related U.S. Appl. No. 10/974,123—Now Abandoned.
NonFinal Office Action, mailed Jul. 31, 2006: Related U.S. Appl. No. 10/986,273.
Final Office Action, mailed Jul. 16, 2007: Related U.S. Appl. No. 10/986,273.
Final Office Action, mailed Mar. 14, 2008: Related U.S. Appl. No. 10/986,273.
NonFinal Office Action, mailed Sep. 18, 2008: Related U.S. Appl. No. 10/986,273.
NonFinal Office Action, mailed Oct. 9, 2007: Related U.S. Appl. No. 10/980,140.
Final Office Action, mailed Mar. 6, 2009: Related U.S. Appl. No. 10/980,140.
NonFinal Office Action, mailed Aug. 1, 2008: Related U.S. Appl. No. 11/129,540.
NonFinal Office Action, mailed Apr. 28, 2009: Related U.S. Appl. No. 11/129,540.
Chirife, Raul et al., "Automatic Beat-to-Beat Left Heart AV Normalizaiton: Is it Possible?" Pace. 2003;26:2103-2110.
Chirife, R. et al., "Nonphysiological Left Heart AV Intervals as a Result of DDD and AAI "Physiological" Pacing," Pace. 1991(Pt. II);14:1752-1756.
Chirife, Raul, "Proposal of a Method for Automatic Optimization of Left Heart Atrioventriular Interval Applicable to DDD Pacemakers," Pace. 1995(Pt. I);18:49-56.
Chirife, Raul MD, "Letters to the Editor," Pace. 2000;23:926.
de Teresa, E. et al., "An Even More Physiological Pacing: Changing the Sequence of Ventricular Activation," Cardiac Pacing, Proceedings of the VIIth World Symposium on Cardiac Pacing, Darmstadt, Germany; Steinkopff Verlag. 1983;395-400.
Ebner, Erich et al., "Ventricular Evoked Response as Clinical Marker for Hemodynamic Changes in Dilative Cardiomyopathy," Pace. 2004;27:166-174.
Gerber, Thomas C. MD et al., "Left Ventricular and Biventricular Pacing in Congestive Heart Failure," Mayo Clin. Proc. 2001;76-803-812.
Ishikawa, Toshiyuki et al., "Prediction of Optimal Atrioventricular Delay in Patients with Implanted DDD Pacemakers," Pace 1999;22:1365-1371.
Ismer, B et al., "Impact of Discriminating Electrophysiological and Electromechanical Determinations of the Optimal AV Delay in Right and Biventricular DDD Pacing," Folia Cardiol. 2006 (tom 13, supl C)—Abstract—029.
Merino, Jose L. MD et al., "Bundle-Branch Reentry and the Postpacing Interval After Entrainment by Right Ventricular Apex Stimulation—A New Approach to Elucidate the Mechanism of Wide-QRS-Complex Tachycardia With Atrioventricular Dissociation," Circulation. 2001;103:1102-1108.
Nelson, Gregory S. PhD, "Left Ventricular or Biventricular Pacing Improves Cardiac Function at Diminished Energy Cost in Patients with Dilated Cardiomyopathy and Left Bundle-Branch Block,"Circulation. 2000;102-3053-3059.
Schreier, G. et al., "Correlation between changes in stroke volume and the paced intracardiac electrogram," Europace. 2002;4;303-310.
Schuchert, Andreas et al., "Effects of Body Position and Exercise on Evoked Response Signal for Automatic Threshold Activation," Pace. 1999;22:1476-1480.
Wang, Paul et al., "Timing Cycles for Biventricular Pacing," Pace. 2002;25;62-75.
Levine, Paul A. MD, Facc et al., "Role of the AV Interval in DDD Pacing: Insights into Programming," 5th Virtual Congress of Cardiology (QVCC)—on the Intranet. Published Oct. 2007.
Levin, Vadim et al., "Interatrial Conduction Measured During Biventricular Pacemaker Implantation Accurately Predicts Optimal Paced Atrioventricular Intervals," J Am Coll Cardiol. 2007;49 (SuppA, 1A)—Abstract 810-6.

* cited by examiner

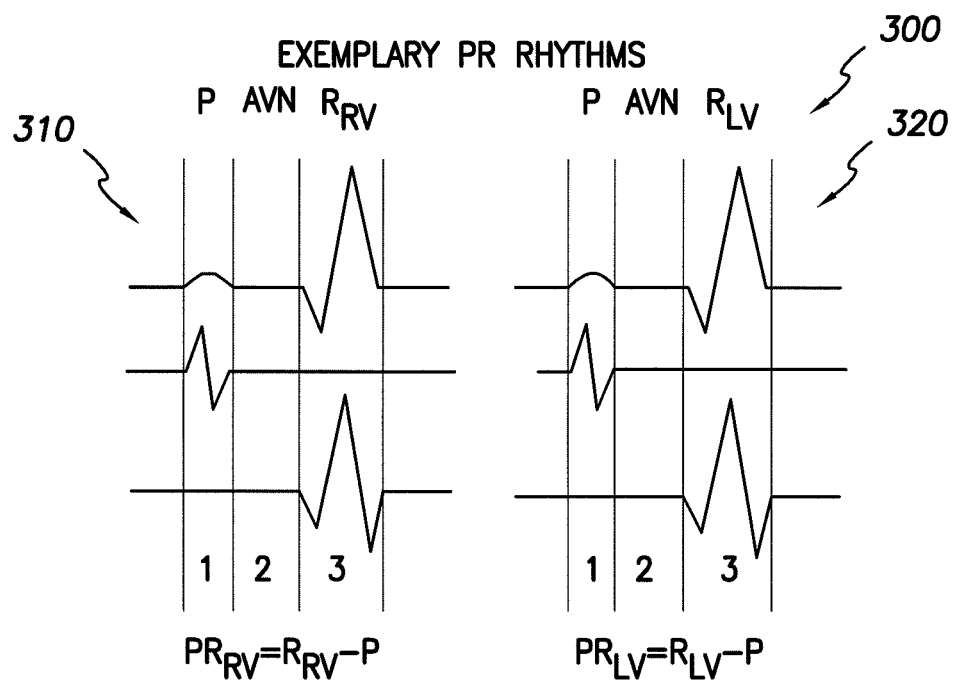
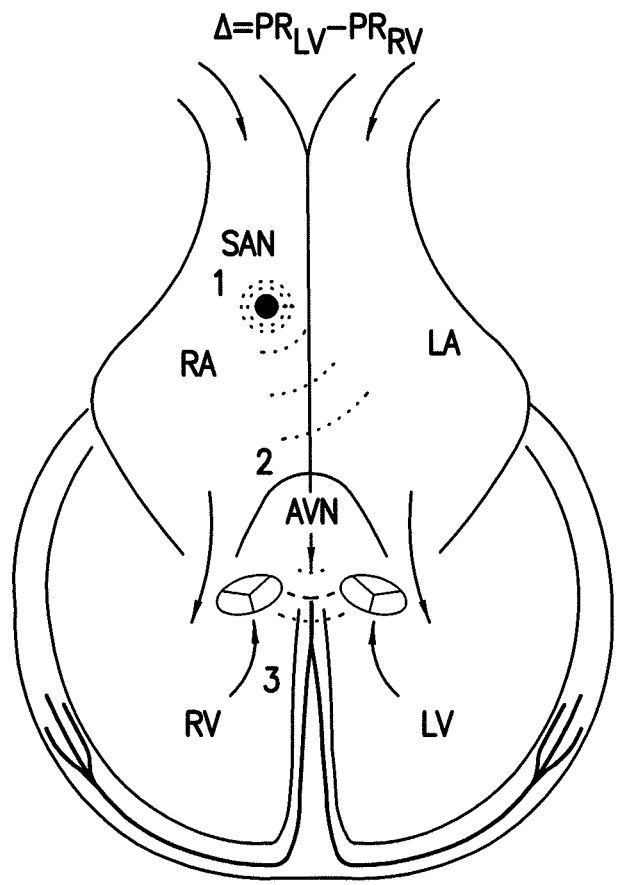
FIG. 3

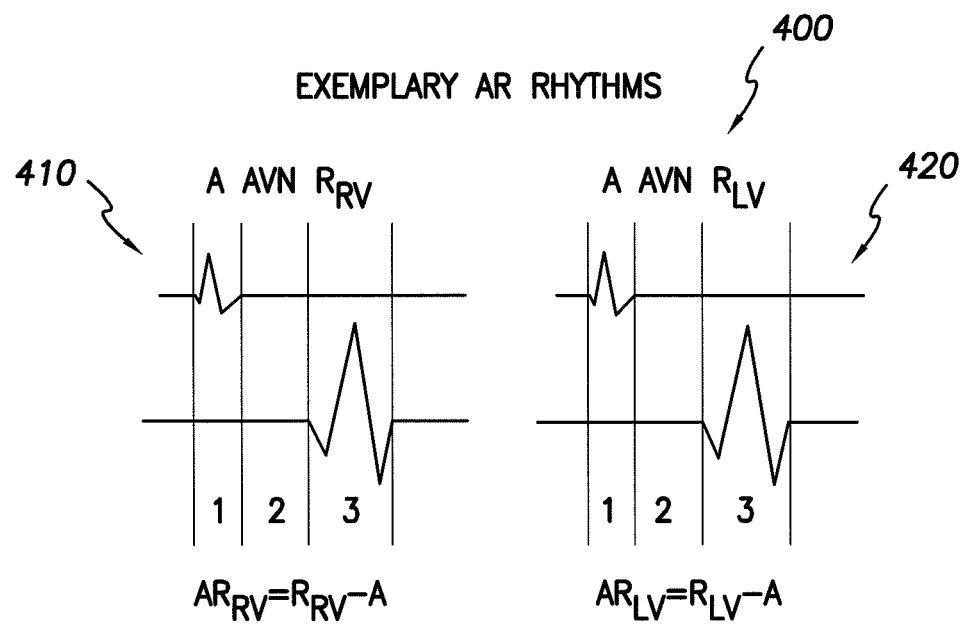
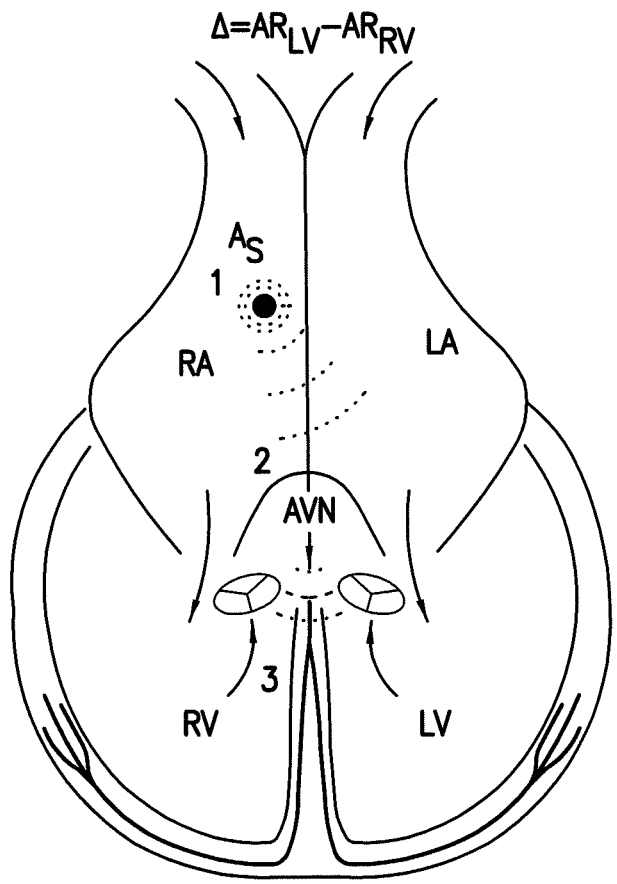
FIG. 4

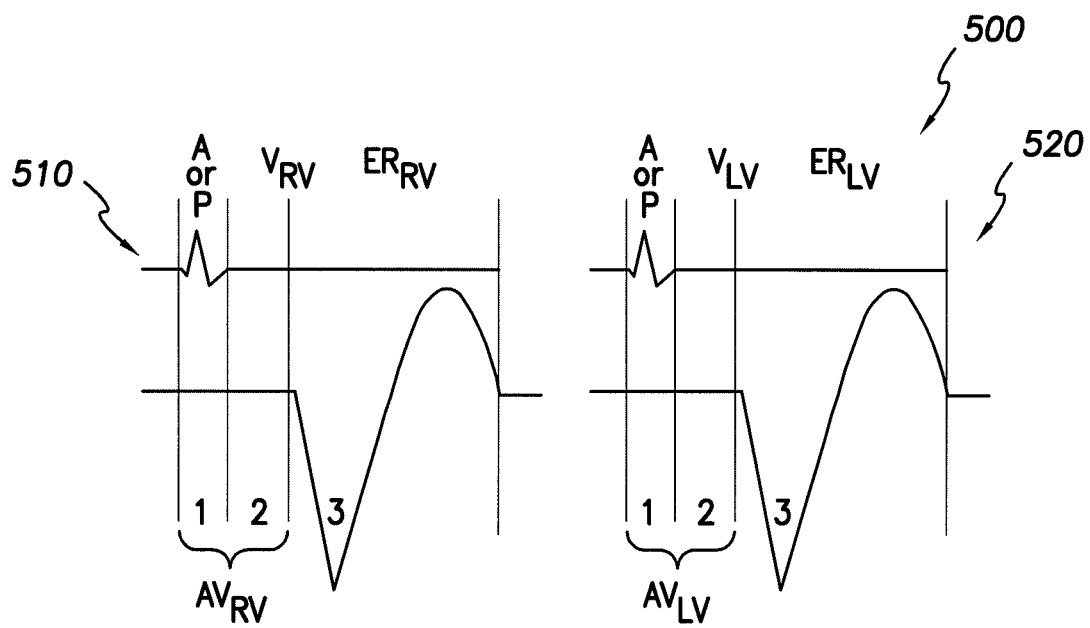
$$A-ER_{RV} = ER_{RV} - A$$
$$A-ER_{LV} = ER_{LV} - A$$
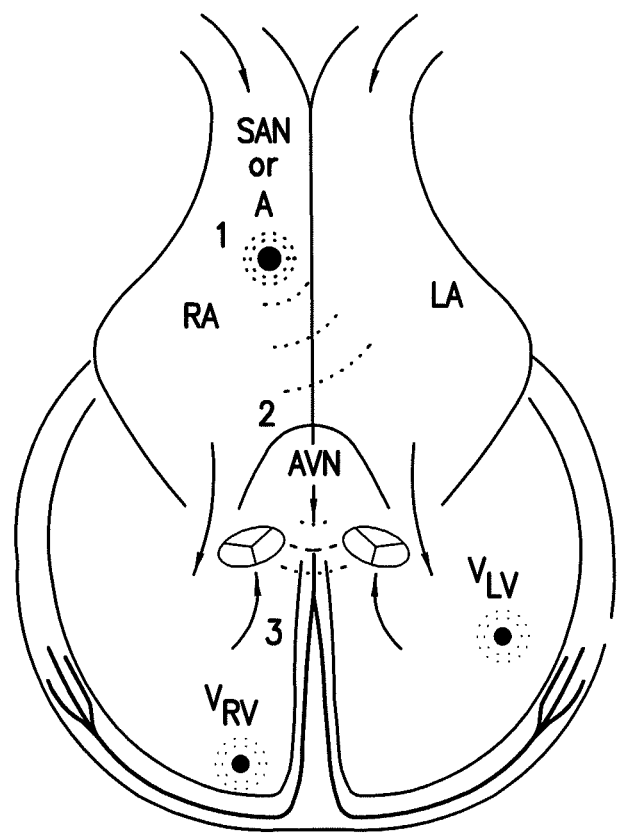
FIG. 5

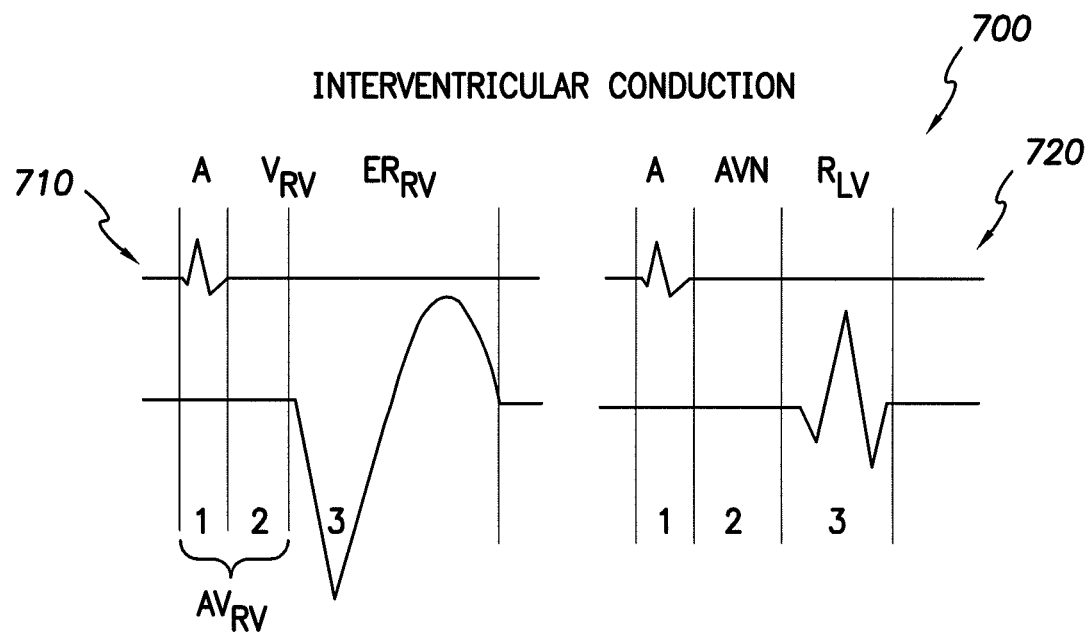
INTERVENTRICULAR CONDUCTION
$PIVCD-RL = R_{LV} - V_{RV}$
$\Delta_{PIVCD} = (R_{RV} - V_{LV}) - (R_{LV} - V_{RV})$   $\Delta_{PIVCD} = PIVCD-LR - PIVCD-RL$
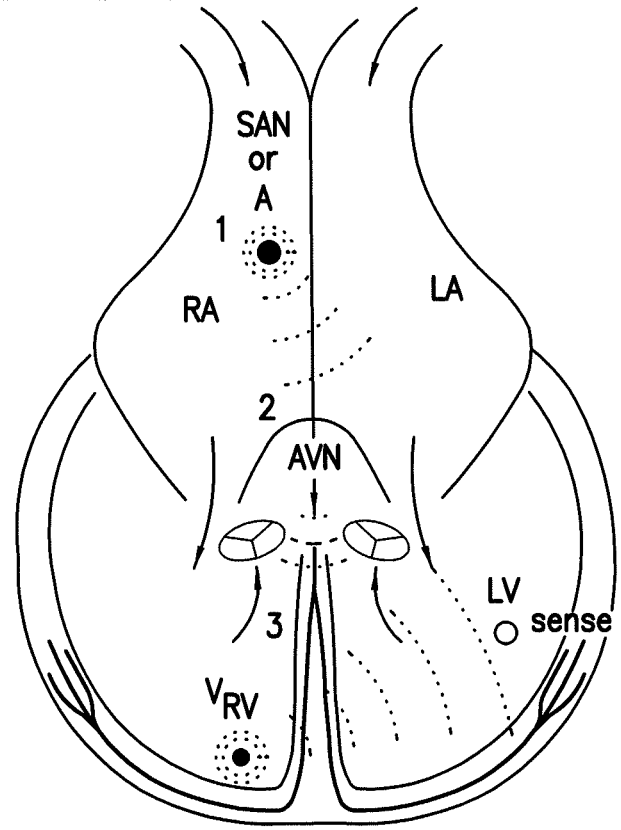
FIG. 7

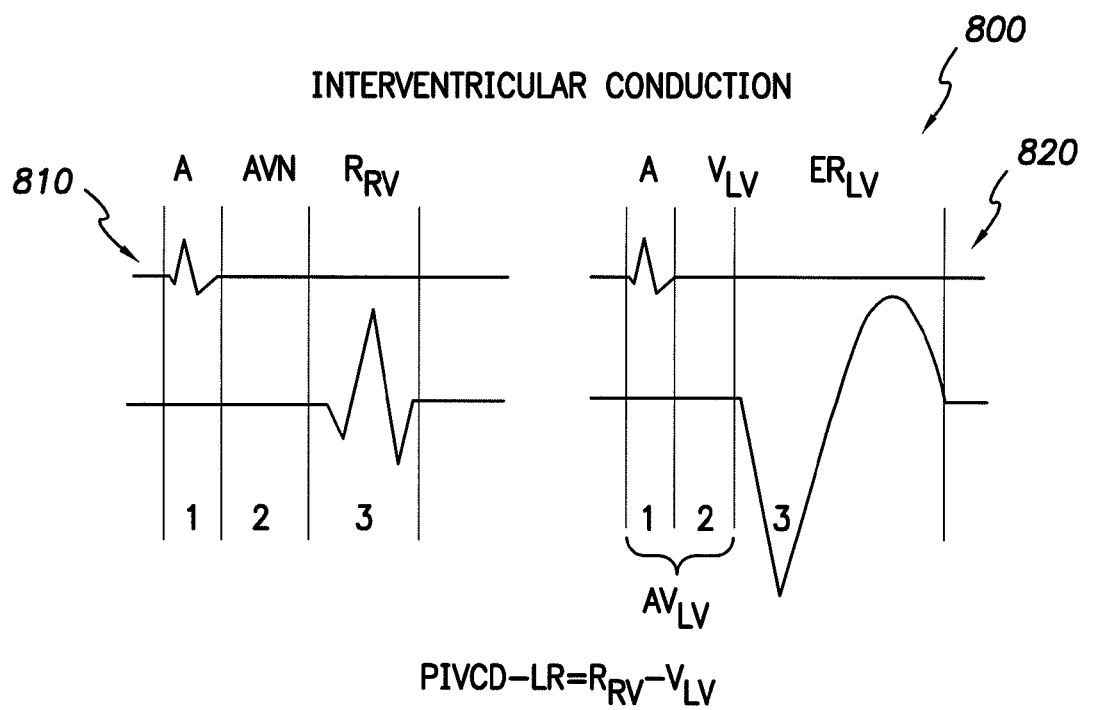
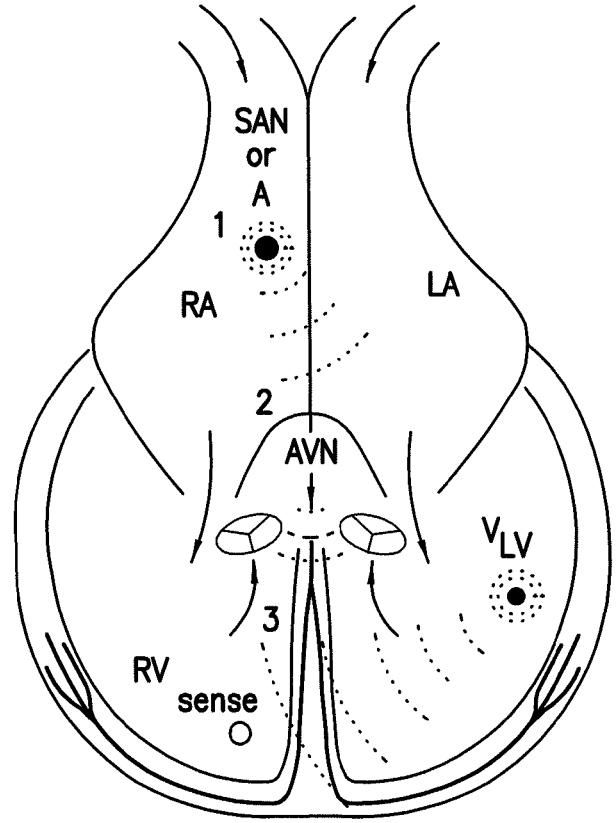
FIG. 8

*900*

EXEMPLARY SCENARIOS

SCENARIO I:   $AR_{LV}$ or $AR_{RV} > AR_{max}$

ACTION:   PACE IN VENTRICLE WITH $AR > AR_{max}$

SCENARIO II:   $AR_{LV}$ and $AR_{RV} > AR_{max}$

ACTION:   PACE IN BOTH VENTRICLES

SCENARIO III:   $AR_{LV}$ and $AR_{RV} < AR_{max}$

ACTION:   NO PACING IN VENTRICLES OR
          OTHER APPROPRIATE ACTIONS

FIG. 9

EXEMPLARY SCENARIOS

1000

SCENARIO I:   $AR_{LV}$ or $AR_{RV} > AR_{max}$

ACTION:   PACE IN VENTRICLE WITH $AR > AR_{max}$

IF $AR_{LV} > AR_{max}$, THEN LEFT BUNDLE BRANCH BLOCK AND PACE EARLY IN LEFT VENTRICLE.

$$\text{IF } |\Delta_{PIVCD}| < \varepsilon,$$
$$\text{THEN } AV_{LV} = AV_{optimal} - |\Delta|$$

$$\text{IF } |\Delta_{PIVCD}| \geq \varepsilon,$$
$$\text{THEN } AV_{LV} = AV_{optimal} - (|\Delta| + \Delta_{PIVCD})$$

IF $AR_{RV} > AR_{max}$, THEN RIGHT BUNDLE BRANCH BLOCK AND PACE EARLY IN RIGHT VENTRICLE $$\text{IF } |\Delta_{PIVCD}| < \varepsilon,$$
$$\text{THEN } AV_{RV} = AV_{optimal} - |\Delta|$$

$$\text{IF } |\Delta_{PIVCD}| \geq \varepsilon,$$
$$\text{THEN } AV_{RV} = AV_{optimal} - (|\Delta| - \Delta_{PIVCD})$$

FIG. 10

EXEMPLARY SCENARIOS

SCENARIO II:    $AR_{LV}$ and $AR_{RV} > AR_{max}$

ACTION:    PACE IN BOTH VENTRICLES

IF $AR_{LV} > AR_{RV}$, THEN:
     (a) SET $AV_{RV}$ to $AV_{optimal}$ and
     (b) PACE EARLY IN LEFT VENTRICLE IF $|\Delta_{PIVCD}| < \varepsilon$,
         THEN $AV_{LV} = AV_{RV} - |\Delta|$ IF $|\Delta_{PIVCD}| \geq \varepsilon$,
         THEN $AV_{LV} = AV_{RV} - (|\Delta| + \Delta_{PIVCD})$ IF $AR_{RV} > AR_{LV}$, THEN:
     (a) SET $AV_{LV}$ to $AV_{optimal}$ and
     (b) PACE EARLY IN RIGHT VENTRICLE IF $|\Delta_{PIVCD}| < \varepsilon$,
         THEN $AV_{RV} = AV_{LV} - |\Delta|$ IF $|\Delta_{PIVCD}| \geq \varepsilon$,
         THEN $AV_{RV} = AV_{LV} - (|\Delta| - \Delta_{PIVCD})$

FIG. 11

EXEMPLARY SCENARIOS 1200

SCENARIOS I OR II $AR_{LV} > AR_{RV}$

IF $|\Delta_{PIVCD}| < \varepsilon$,
      THEN $AV_{LV} = AV_{optimal} - \alpha|\Delta|$ IF $|\Delta_{PIVCD}| \geq \varepsilon$,
      THEN $AV_{LV} = AV_{optimal} - \alpha(|\Delta| + \Delta_{PIVCD})$ $AR_{RV} > AR_{LV}$ IF $|\Delta_{PIVCD}| < \varepsilon$,
      THEN $AV_{RV} = AV_{optimal} - \alpha|\Delta|$ IF $|\Delta_{PIVCD}| \geq \varepsilon$,
      THEN $AV_{RV} = AV_{optimal} - \alpha(|\Delta| + \Delta_{PIVCD})$

FIG. 12

SYSTEMS AND METHODS FOR CONTROLLING VENTRICULAR PACING IN PATIENTS WITH LONG INTER-ATRIAL CONDUCTION DELAYS

CROSS-REFERENCE TO RELATED APPLICATIONS

This application is related to U.S. patent applications:
1) Ser. No. 10/703,070, filed Nov. 5, 2003, entitled "Methods for Ventricular Pacing", now abandoned;
2) Ser. No. 10/974,123, filed Oct. 26, 2004, now abandoned;
3) Ser. No. 10/986,273, filed Nov. 10, 2004;
4) Ser. No. 10/980,140, filed Nov. 1, 2004;
5) Ser. No. 11/129,540, filed May 13, 2005;
6) Ser. No. 11/952,743, filed Dec. 7, 2007; and
7) Ser. No. 11/434,032, filed May 15, 2006, which are each incorporated herein by reference.

FIELD OF THE INVENTION

The invention generally relates to implantable cardiac stimulation devices such as pacemakers and implantable cardioverter-defibrillators (ICDs) and, in particular, to techniques for determining atrio-ventricular pacing delays for use in pacing the ventricles of a patient in which such a device is implanted.

BACKGROUND OF THE INVENTION

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or W pacing delay may occur at implantation and sometimes, a re-optimization may occur during a follow-up consultation. While such optimizations are beneficial, the benefits may not be long lasting due to changes in various factors related to device and/or cardiac function. The patent applications cited above set forth various improved systems and methods for, inter alia, allowing a pacemaker or ICD to determine and/or adjust AV/PV/VV pacing delays so as to help maintain the pacing delays at optimal values. In particular, techniques were set forth for exploiting various interventricular conduction delays to determine optimal AV/PV/VV pacing delays. Techniques were also set forth for exploiting the VV delays to determine which ventricles should be paced—the left ventricle (LV), the right ventricle (RV), both ventricles, or neither. These various techniques are also described herein below.

Other techniques have been set forth for determining AV/PV delays based on inter-atrial conduction delays and interventricular conduction delays. In particular, see U.S. Pat. No. 7,248,925, to Bruhns et al., entitled "System and Method for Determining Optimal Atrioventricular Delay based on Intrinsic Conduction Delays," which is fully incorporated by reference herein.

Within certain patients with long inter-atrial conduction delays, circumstances can arise where optimal AV/PV pacing delays are suggested that are longer than the intrinsic AR/PR conduction delays within the patient. This can occur, e.g., within heart failure patients having otherwise normal AR/PR delays (i.e. AR/PR delays of about 150 milliseconds (ms)). As can be appreciated, if the AV/PV pacing delays are set longer than the AR/PR conduction delays, the ventricles might depolarize only in response to atrio-ventricular conduction and hence the V-pulses will not capture. Improvements are set forth herein that address these concerns.

SUMMARY

In an exemplary embodiment, a method is provided for delivering cardiac pacing therapy using an implantable cardiac stimulation device. Briefly, an inter-atrial conduction time delay (IACT) is determined for a patient in which the device is implanted. (The IACT value may also be referred to as an A-A delay value.) Preferred or optimal atrio-ventricular pacing delays (AV/PV) and an interventricular pacing delay (VV) are also determined for use in pacing the heart of the patient based, in part, on the inter-atrial conduction delay (IACT). The determination of AV/PV and VV may exploit rapid or quick optimization techniques referred to herein as QuickOpt. Atrio-ventricular conduction delays (AR/PR) are then measured within the patient. The atrio-ventricular pacing delays (AV/PV) are compared with the measured atrio-ventricular conduction delays (AR/PR). If the atrio-ventricular pacing delays (AV/PV) are less than the measured atrio-ventricular conduction delays (AR/PR), biventricular pacing is delivered using the atrio-ventricular pacing delay (AV/PV) and the interventricular pacing delay (VV). However, if the atrio-ventricular pacing delays (AV/PV) are not less than the corresponding atrio-ventricular conduction delays (AR/PR), as can occur if the IACT is large for the patient, then alternative pacing regimes are selectively enabled, such as mono-ventricular pacing in the chamber having the longer PR/AR value, biventricular pacing with negative hysteresis, or biventricular pacing with AV/PV delays reduced using predetermined offset values.

The alternative regimes are provided to ensure that the AV/PV pacing delays properly exceed the AR/PR conductions delays within the patient despite the long IACT of the patient. In some embodiments, the implantable medical device further distinguishes among the alternative pacing regimes based on whether measured AR/PR conduction delays exceed predetermined conduction delay thresholds ($AR_{MIN-TH}/PR_{MIN-TH}$) and whether the measured IACT exceeds a predetermined IACT threshold ($IACT_{TH}$).

System and method implementations of these techniques are presented herein.

BRIEF DESCRIPTION OF THE DRAWINGS

Features and advantages of the described implementations can be more readily understood by reference to the following description taken in conjunction with the accompanying drawings.

FIG. 3 is an approximate anatomical diagram of a heart, a surface ECG and two IEGM waveforms that exhibit an intrinsic P wave and an R wave at RV lead and at a LV lead and the illustration of calculated $\Delta$.

FIG. 4 is an approximate anatomical diagram of a heart and two IEGM waveforms that exhibit an A wave and an R wave at a RV lead and a LV lead and the illustration of calculated $\Delta$.

FIG. 5 is an approximate anatomical diagram of a heart and two sets of IEGM waveforms that include an A or P wave on an atrial sensing channel and evoked response on a ventricular sensing channel.

FIG. 7 is an approximate anatomical diagram of a heart and two sets of IEGM waveforms wherein one set includes an evoked response in a right ventricle and the other set includes a response from a conducted event in a left ventricle for the illustration of the PIVCD_RL term needed for $\Delta_{PIVCD}$.

FIG. 8 is an approximate anatomical diagram of a heart and two sets of IEGM waveforms wherein one set includes an evoked response in a left ventricle and the other set includes a response from a conducted event in a right ventricle for the illustration of the PIVCD_LR needed for $\Delta_{PIVCD}$.

FIG. 9 is of various exemplary scenarios labeled Scenario I, Scenario II and Scenario III, which are related to cardiac therapy and, in particular, ventricular pacing.

FIG. 10 is of various exemplary equations related to Scenario I of FIG. 9, which may be indicative of left bundle branch block or right bundle branch block.

FIG. 11 is of various exemplary equations related to Scenario II of FIG. 9, which may be indicative of left bundle branch block or right bundle branch block.

FIG. 12 is of various exemplary equations related to Scenario I and/or Scenario II of FIG. 9, wherein an exemplary parameter such as $\alpha$ of FIG. 6 may be used to one or more determine pacing delays.

DETAILED DESCRIPTION OF THE PREFERRED EMBODIMENTS

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used at times to reference like parts or elements throughout the description.

Overview

Exemplary methods, devices and/or systems pertain generally to ventricular pacing. For example, various exemplary methods include deciding whether to use ventricular pacing and, if so, whether to pace in a single ventricle or in both ventricles. If such a method decides that ventricular pacing is appropriate, then the method may also determine an atrio-ventricular delay for one or both ventricles. For the case of bi-ventricular pacing, the method may determine an atrio-ventricular delay for each ventricle and/or an interventricular delay (e.g., which may be inherent in the use of two atrio-ventricular delay times). Such a method may reduce frequency of ventricular or bi-ventricular pacing and/or enhance cardiac performance. Further, such a method may optimize pacing as a function of time or in response to changes in any of a variety of factors related to cardiac and/or device performance.

With respect to cardiac performance, various exemplary methods, devices and/or systems include an adjustable cardiac performance parameter. Such a performance parameter is optionally determined via cardiac testing. As described below, echocardiogram testing or other hemodynamic sensors (e.g., pressure, etc.) may be used to determine an optimal interventricular pacing delay suitable for use in bi-ventricular pacing. In this example, the performance parameter may be a function of this delay and an intrinsic interventricular conduction delay, which may be measured in vivo. Various exemplary methods, devices and/or systems may make adjustments to pacing therapy based on information from in vivo electrocardiogram sensing. Such methods, devices and/or systems may or may not include other sensors such as hemodynamic sensors.

The following description begins with a discussion of exemplary implantable devices and associated components followed by a discussion of heart rhythms and associated waveforms. Next, a discussion of cardiac performance follows, and the detailed description continues with a discussion of various exemplary methods, devices and/or systems.

Exemplary Stimulation Device

The techniques described below are intended to be implemented in connection with any stimulation device that is configured or configurable to stimulate nerves and/or stimulate and/or shock a patient's heart.

Figure 1:
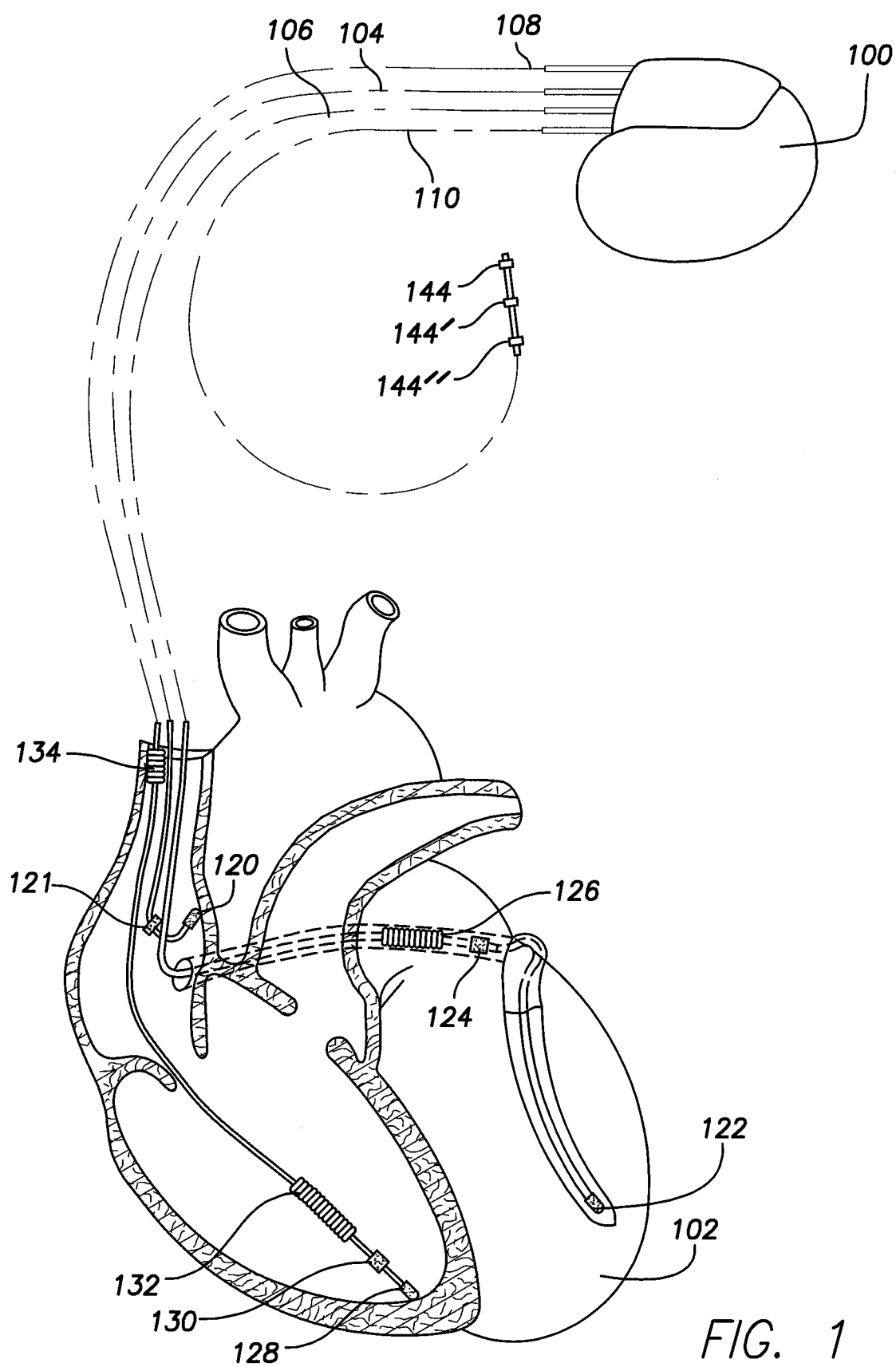
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve. Such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve. Such an electrode may be positioned on the lead or a bifurcation or leg of the lead.

Figure 2:
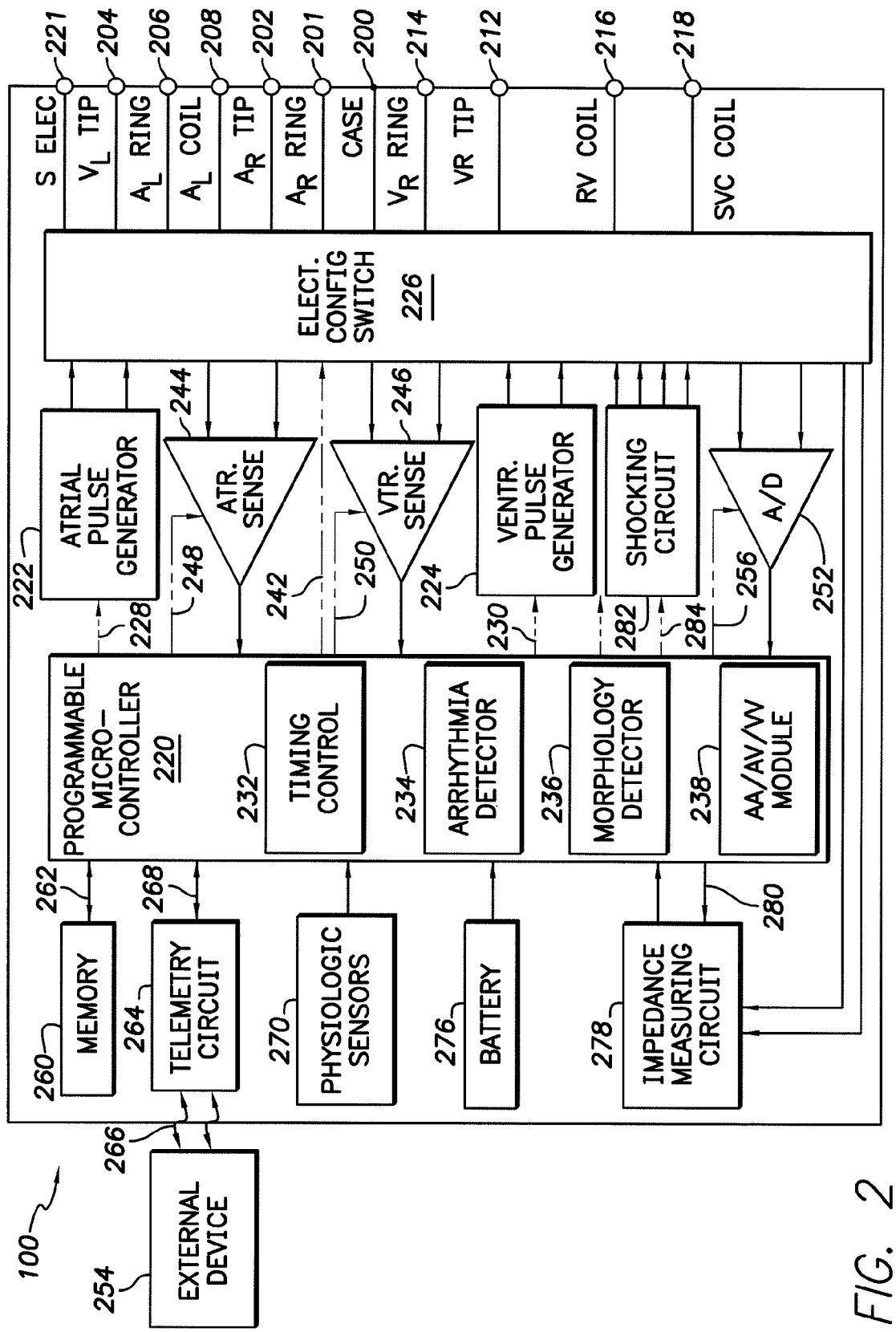
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (e.g., AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module; the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes an AA delay, AV delay and/or VV delay module 238 for performing a variety of tasks related to AA delay, AV delay and/or VV delay. This component can be utilized by the stimulation device 100 for determining desirable times to administer various therapies, including, but not limited to, ventricular stimulation therapy, biventricular stimulation therapy, resynchronization therapy, atrial stimulation therapy, etc. The AA/AV/VV module 238 may be implemented in hardware as part of the microcontroller 220, or as software/firmware instructions programmed into the device and executed on the microcontroller 220 during certain modes of operation. Of course, such a module may be limited to one or more of the particular functions of AA delay, AV delay and/or VV delay. Such a module may include other capabilities related to other functions that may be germane to the delays. Such a module may help make determinations as to fusion.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Heart Rhythms

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction. Depending on patient or other factors, the time could be set at some time other than 5 ms.

The variable Δ represents an interventricular delay that is based on an atrio-ventricular delay for the left ventricle ($PR_{LV}$) and an atrio-ventricular delay for the right ventricle ($PR_{RV}$). The variable |Δ| is shown as the absolute value of the difference while herein and in the figures the variable Δ (e.g., $\Delta=PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa. In general, the term "atrio-ventricular" delay may pertain to an AV delay, a PV delay, an AR delay or a PR delay.

With respect to cardiac condition, a long interventricular delay may be indicative of a conduction block. For example, left bundle branch block (LBBB) may cause the left ventricle to contract more than approximately 50 ms after contraction of the right ventricle (e.g., Δ>0). Whereas a right bundle branch block (RBBB) may be expected to cause the right ventricle to contract well after the left ventricle (e.g., Δ<0). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

As inferred in the Background section, significant asynchronous ventricular contraction (e.g., non-optimal VV delay) may in some instances impair cardiac function. Thus, where a patient has an interventricular delay that would result in significant asynchronous contraction, various exemplary methods, devices and/or systems described herein may treat such a cardiac condition and reduce deleterious effects associated with such the condition. Hence, various exemplary methods that pace in response to right and left ventricular conduction asymmetries may improve cardiac function.

FIG. 4 shows an approximate anatomical diagram of a heart and two sets of waveforms 400. One set of waveforms 410 corresponds in part to right ventricular activity while another set of waveforms 420 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 410, 420 show various IEGMs of heart activity (e.g., polarization, depolarization, etc.) wherein atrial depolarization is represented as an "A wave" and ventricular depolarization is represented as an "R wave", or QRS complex. Both sets 410, 420 show an A wave followed by an AVN conduction delay (AVN) and a right ventricular R wave or QRS complex ($R_{RV}$) for the set 410 and a left ventricular R wave or QRS complex ($R_{LV}$) for the set 420. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 4 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g., $\Delta=AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode to yield a low standby rate, etc.

Referring to FIG. 5, an approximate anatomical diagram of a heart and two sets of waveforms 500. One set of waveforms 510 corresponds to atrial and right ventricular activity and the other set of waveforms 520 corresponds to atrial and left ventricular activity. The two sets of waveforms approximate IEGM waveforms that may be sensed in vivo using an implanted device. In both sets 510, 520, A represents an atrial waveform based on an atrial pace and ER represents an evoked response (e.g., capture) based on a ventricular pace (labeled "$V_{RV}$" or "$V_{LV}$").

In FIG. 5, action potentials propagating through the heart are labeled as follows: 1, associated with a paced atrial stimulus or an intrinsic SAN stimulus and the atria; 2, associated with the atrio-ventricular node (AVN); and 3, associated with a paced right ventricle and a paced left ventricle. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3). However, ventricular pacing may override an atrial paced or intrinsic stimulus or may allow for ventricular stimulation and contraction where AVN conduction is impaired. Thus, in this example, ventricular rhythm typically relies on ventricular stimulation and conduction of electrical activity through the ventricles.

As mentioned, the two sets of waveforms of heart activity (e.g., polarization, depolarization, etc.) include atrial depolarization represented as an "A wave" and ventricular depolarization represented as an "ER wave" or evoked response. The delay between the atrial stimulus and the right ventricular stimulus is referred to as $AV_{RV}$ while the delay between the atrial stimulus and the left ventricular stimulus is referred to as $AV_{LV}$. The set 510 shows an A wave followed by an AVN conduction delay (AVN) and a right ventricular ER wave or evoked response. The set 520 shows an A wave followed by an AVN conduction delay (AVN) and a left ventricular evoked response ($ER_{LV}$). Often detection of an R wave or an evoked response relies on signal amplitude or signal derivative with respect to time. Further, many detection methods are capable of assigning a time to a detected R wave or evoked response or assigning a time span to an A wave to R wave or evoked response interval, which are shown in FIG. 5 as A-$ER_{RV}$ for the right ventricle and A-$ER_{LV}$ for the left ventricle. If A-$ER_{RV}$ and A-$ER_{LV}$ are approximately equal, then the right ventricle and the left ventricle contract in a substantially synchronous manner. While FIG. 5 shows a paced atrial stimulus, an intrinsic SAN stimulus may suffice and hence result in P-ER waveforms and corresponding P-$ER_{RV}$ and P-$ER_{LV}$ times. Information shown in FIG. 6 may be related to a scenario such as that shown in FIG. 5. In particular, where pacing occurs in both ventricles, corresponding IEGM waveforms may appear substantially the same as those of the set 510 and/or the set 520. Noting that, in general, an implanted device typically has a single atrial sensing channel and typically one or two ventricular channels (e.g., optionally one switchable channel that can switch between sensing in the left ventricle and the right ventricles and/or one ventricle and both ventricles).

Figure 6:
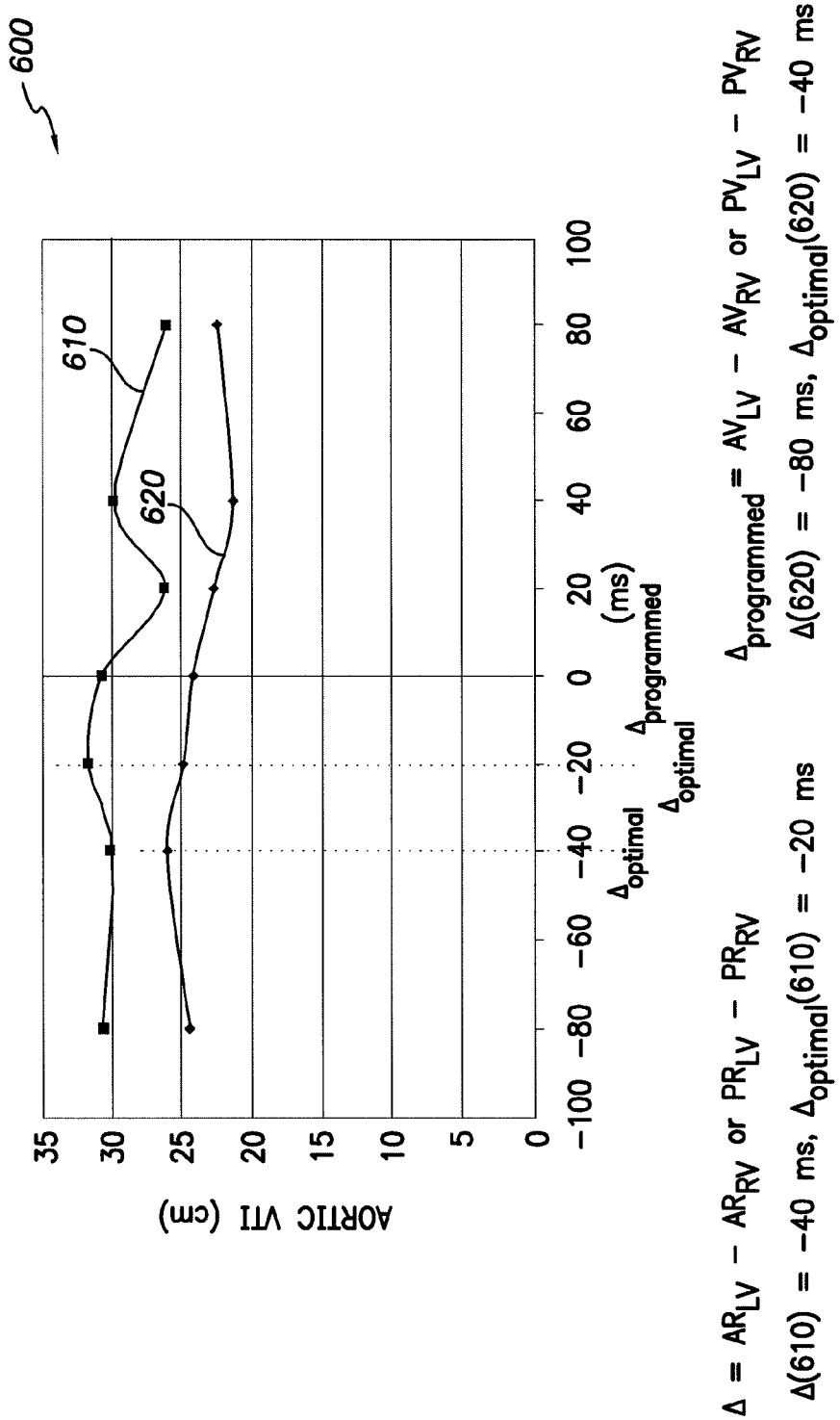
FIG. 6 is an exemplary plot of aortic velocity time integral and exemplary equations for a parameter $\alpha$.

FIG. 6 shows a plot 600 of aortic velocity time integral versus $\Delta_{programmed}$ wherein, as shown, $\Delta_{programmed}=AV_{LV}-AV_{RV}$ or $PV_{LV}-PV_{RV}$. Thus, a $\Delta_{programmed}$ value less than zero indicates that for bi-ventricular pacing, a pacing stimulus or stimuli was delivered to the left ventricle prior to the right ventricle. A $\Delta_{programmed}$ of zero indicates that both $AV_{RV}$ and $AV_{LV}$ or $PV_{RV}$ and $PV_{LV}$ were set to approximately equal AV or PV times, which may optionally be an overall optimal time (e.g., $AV_{optimal}$ and $PV_{optimal}$).

The information of plot 600 was acquired using human subjects and echocardiograms. The velocity time integral, VTI, is the product of blood velocity in the aorta over a period of time. In general, the period of time corresponds to a beat-to-beat time and hence VTI typically correlates well with or serves as an indicator of cardiac performance. Thus, a higher VTI value normally indicates better cardiac performance.

The plot 600 includes data 610, 620 for two patients. As plotted, the upper data 610 exhibits a maximum VTI at a $\Delta_{programmed}$ of approximately −20 ms (e.g., left ventricular stimulus delivered 20 ms prior to the right ventricular stimulus) whereas the lower data 620 exhibits a maximum VTI at a $\Delta_{programmed}$ of approximately −40 ms (e.g., left ventricular stimulus delivered 40 ms prior to the right ventricular stimulus). Thus, the data 610, 620 indicate that, for these particular patients, cardiac performance is improved by pacing the left ventricle prior to the right ventricle. Further, for each patient, a corresponding optimal $\Delta_{programmed}$ exists, referred to herein as $\Delta_{optimal}$.

Referring again to FIG. 3 or 4, a comparison between Δ and $\Delta_{programmed}$ or $\Delta_{optimal}$ can indicate a difference between a current cardiac therapy or state and a potentially better cardiac therapy or state. For example, consider the following equation (Eqn. 1):

$$\alpha = \Delta_{optimal}/\Delta \quad (1)$$

where α is an optimization parameter. Hence in the example of FIG. 6, where the patient corresponding to data 610 had a Δ of approximately −40 ms and the patient corresponding to data 620 had a Δ of approximately −80 ms, the parameter α was approximately 0.5 for both patients. The use of such an optimization parameter is described further below. In general, the closer α is to unity, there may be little need to pace either ventricle if the $PR_{RV}$, $PR_{LV}$, $AR_{RV}$, and/or $AR_{LV}$ times are acceptable (noting that acceptable AR times are generally longer than acceptable PR times due to conduction differences between a paced atrial stimulus and intrinsic atrial activity).

While the information of FIG. 6 pertains primarily to ventricular activity, such an analysis may be performed for atrial activity. For example, where bi-atrial pacing is available, a programmed value for atrial activity may be defined as $\Delta_{programmed} = A_{LA} - A_{RA}$, wherein a negative value indicates that the right atrium was paced prior to the left atrium. An echocardiogram examination or other suitable examination may be used to determine an optimal value (e.g., $\Delta_{optimal} = A_{LA} - A_{RA}$). Yet further, an atrial parameter, or $\alpha_{atrial}$, may be used in an implantable device to adjust and/or determine one or more pacing times of one or both atria.

Some implantable devices allow left atrial pacing via an electrode on a lead positioned in the coronary sinus. For example, the exemplary device 100 includes the lead 106, which optionally has one or more electrodes positioned proximate to the left atrium and capable of delivering stimulation to the left atrium and/or sensing left atrial activity. Right atrial pacing and/or sensing may occur via, for example, the lead 104 and one or more electrodes, as appropriate. Yet further, one or more electrodes may be used to sense both right atrial and left atrial activity using one or more sensing channels. For example, a right atrial lead and a left atrial lead may connect to a single sensing channel to acquire a signal that includes indicia of right atrial activity and left atrial activity. Such an arrangement may allow for determination of an atrial Δ (e.g., $P_{LA} - P_{RA}$, $A_{LA} - P_{RA}$, $P_{LA} - A_{RA}$) and/or other parameters.

FIGS. 7 and 8 show plots, approximate anatomical diagrams and equations associated with yet another delay time, $\Delta_{PIVCD}$, referred to a paced interventricular conduction delay (PIVCD). FIG. 7 pertains to pacing in a right ventricle and sensing in a left ventricle wherein the time between pacing and sensing is referred to as a right to left PIVCD or PIVCD-RL, which equals $R_{LV} - V_{RV}$, wherein $V_{RV}$ is a pace time of a pacing stimulus in the right ventricle and $R_{LV}$ is a sense time of a right ventricle, evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices and/or systems include a capture algorithm (e.g., autocapture).

FIG. 7 shows a set of waveforms 710 that include an atrial event (e.g., A or P), an atrial to ventricular paced delay $AV_{RV}$, a ventricular pace time $V_{RV}$ and a sensed evoked response in the right ventricle $ER_{RV}$. Another set of waveforms 720 pertains primarily to the left ventricle and includes an atrial event (e.g., A or P), an AVN delay and a sensed evoked response in the left ventricle $R_{LV}$ which is a result of the stimulus $V_{RV}$ in the right ventricle. To ensure that the sensed evoked response in the left ventricle $R_{LV}$ is not due to conducted electrical activity from the atria, a sufficiently short ventricular paced delay $AV_{RV}$ is used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

FIG. 8 pertains to pacing in a left ventricle and sensing in a right ventricle wherein the time between pacing and sensing is referred to as a left to right PIVCD or PIVCD-LR, which equals $R_{RV} - V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, PIVCD-LR is normally greater than zero. To ensure that the pacing stimulus in the left ventricle results in an evoked response, a capture routine or algorithm may be implemented. Thus, various exemplary methods, devices and/or systems include a capture algorithm (e.g., autocapture).

FIG. 8 shows a set of waveforms 820 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 810 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 70 ms may suffice. In one example, $AV_{LV}$ is set to approximately 50 ms to approximately 80 ms. $AV_{LV}$ may also be set sufficiently short to avoid fusion. While AV is referred to, PV may also apply where appropriate.

In general, bipolar sensing (or other multipolar/combipolar sensing) may increase signal to noise of the sensed activation response in the left ventricle when compared to unipolar sensing that includes use of an in vivo, yet non-local electrode such as a pulse generator can. The latter technique is often more used in detection of evoked response or the applications utilizing far-field signals. Further, bipolar sensing that includes two electrodes positioned in proximity to each other (e.g., less than approximately 4 cm), may increase signal to noise and sensitivity and better localize an activation wavefront.

Thus, in summary, FIG. 3 through FIG. 8 described the following delays that are related to pacing in the right ventricle and/or the left ventricle:

PV Delay between an atrial event and a paced ventricular event
$PV_{optimal}$ Optimal PV delay
$PV_{RV}$ PV delay for right ventricle
$PV_{LV}$ PV delay for left ventricle
AV Delay for a paced atrial event and a paced ventricular event
$AV_{optimal}$ Optimal AV delay
$AV_{RV}$ AV delay for right ventricle
$AV_{LV}$ AV delay for left ventricle
$\Delta$ Estimated interventricular delay, e.g., via IEGM, etc.
$\Delta_{programmed}$ Programmed interventricular delay (e.g., a programmed VV delay)
$\Delta_{optimal}$ Optimal interventricular delay, e.g., via hemodynamic sensing/sensor or other cardiac sensing
PIVCD-RL Delay between paced RV and sensed LV
PIVCD-LR Delay between paced LV and sensed RV
$\Delta_{PIVCD}$ Paced interventricular conduction delay FIG. 9 shows various exemplary scenarios wherein at least some delay information is known. In these scenarios, delay information pertains to delay between an atrial event (e.g., A or P) and a sensed ventricular event (e.g., R). Thus, such delay information pertains to conduction from the atrium (or atria) to the right ventricle and/or the left ventricle.

In a first scenario, Scenario I, delay information, $AR_{LV}$ and/or $AR_{RV}$ (or $PR_{LV}$ and/or $PR_{RV}$), is assessed relative to a predetermined delay, $AR_{max}$ (or $PR_{max}$). As already mentioned, $AR_{max}$ or $PR_{max}$ may be approximately 250 ms or approximately 200 ms, respectively. Other values may be suitable depending on patient or other circumstances. In Scenario I, if one of the delays exceeds the predetermined delay, then pacing should occur in the ventricle associated with the delay that exceeds the predetermined delay. This ventricle is referred to herein as the master ventricle. For example, if $AR_{max}$ is 250 ms, $AR_{RV}$ is 150 ms and $AR_{LV}$ is 300 ms, then pacing should occur in the left ventricle because $AR_{LV}$ is greater than 250 ms.

In a second scenario, Scenario II, delay information, $AR_{LV}$ and $AR_{RV}$ (or $PR_{LV}$ and $PR_{RV}$), is assessed relative to a predetermined delay, $AR_{max}$ (or $PR_{max}$). In Scenario II, if both of the delays exceed the predetermined delay, then pacing should occur in both ventricles and first in the ventricle associated with the longest delay, which ventricle is referred to herein as the master ventricle. For example, if $PR_{max}$ is 200 ms, $PR_{RV}$ is 250 ms and $PR_{LV}$ is 300 ms, then pacing should occur in both ventricles and first in the left ventricle because $PR_{LV}$ is greater than $PR_{RV}$.

In a third scenario, Scenario III, delay information, $AR_{LV}$ and $AR_{RV}$ (or $PR_{LV}$ and $PR_{RV}$), is assessed relative to a predetermined delay, $AR_{max}$ (or $PR_{max}$). In Scenario III, if both of the delays do not exceed the predetermined delay, then ventricular pacing may or may not occur depending on one or more other circumstances. For example, if $AR_{max}$ is 250 ms, $AR_{RV}$ is 150 ms and $AR_{LV}$ is 200 ms, then pacing may not occur because intrinsic conduction is apparently adequate. However, if the difference between $AR_{RV}$ and $AR_{LV}$ is deemed excessive or otherwise undesirable, then single or biventricular pacing may occur in an effort to compensate or correct for this difference.

FIG. 10 shows various, more specific examples related to Scenario I of FIG. 9, wherein at least some delay information is known about paced interventricular conduction delay (PIVCD). In these scenarios, such delay information pertains to delay between a paced event (e.g., V) in one ventricle and a sensed event (e.g., R) in another ventricle. Thus, such delay information pertains to conduction between the right ventricle and the left ventricle.

The more specific examples rely on a comparison between $|\Delta_{PIVCD}|$ and a PIVCD conduction related parameter $\epsilon$. The parameter $\epsilon$ represents an interventricular correction term for conduction between the ventricles and may represent a tolerable limit for conduction heterogeneity. (Note that, in the predecessor applications cited above, this term was referred to as a conduction limit rather than a correction term. The terminology used to refer to these and other terms is, of course, arbitrary.) For example, a large $\epsilon$ may be used to tolerate or to not compensate for conduction in one direction being significantly greater than conduction in the other direction.

As shown in FIG. 10, if $AR_{LV}$ is greater than $AR_{max}$ (or $PR_{LV}$ is greater than $PR_{max}$) and $|\Delta_{PIVCD}|$ is less than $\epsilon$, then pacing occurs in the left ventricle wherein the timing of the paced stimulus (or stimuli) follows the equation (Eqn. 2):

$$AV_{LV}=AV_{optimal}-|\Delta| \text{ or } PV_{LV}=PV_{optimal}-|\Delta| \qquad (2)$$

In Eqn. 2, $AV_{optimal}$ or $PV_{optimal}$ represents an optimal or predetermined delay. Thus, Eqn. 2 ensures that pacing compensates for at least some of the conduction problem associated with the left ventricle. If however, $|\Delta_{PIVCD}|$ is greater than or equal to $\epsilon$, then pacing occurs in the left ventricle wherein the timing of the paced stimulus (or stimuli) follows the equation (Eqn. 3):

$$AV_{LV}=AV_{optimal}-(|\Delta|+\Delta_{PIVCD}) \text{ or}$$

$$PV_{LV}=PV_{optimal}-(|\Delta|+\Delta_{PIVCD}) \qquad (3)$$

Thus, Eqn. 3 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 210 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms−210 ms| or 90 ms and $\Delta_{PIVCD}$ is (10 ms−20 ms) or −10 ms. Thus, pacing should occur in the left ventricle with an atrioventricular delay as follows:

$$AV_{LV}=180 \text{ ms}-(90 \text{ ms}+(-10 \text{ ms}))=100 \text{ ms}$$

In this example, if $AR_{RV}$ is 210 ms, then the difference between ventricular activation is approximately 210 ms−100 ms or 110 ms, wherein the left ventricle is activated prior to the right ventricle, which may be referred to as $|\Delta_{actual}|$ which is equal to $|AV_{LV}-AR_{RV}|$.

As shown in FIG. 10, if $AR_{RV}$ is greater than $AR_{max}$ (or $PR_{RV}$ is greater than $PR_{max}$) and $|\Delta_{PIVCD}|$ is less than $\epsilon$, then pacing occurs in the right ventricle wherein the timing of the paced stimulus (or stimuli) follows the equation (Eqn. 4):

$$AV_{RV}=AV_{optimal}-|\Delta| \text{ or } PV_{RV}=PV_{optimal}-|\Delta| \quad (4)$$

In Eqn. 4, $AV_{optimal}$ or $PV_{optimal}$ represents an optimal or predetermined delay. Thus, Eqn. 4 ensures that pacing compensates for at least some of the conduction problem associated with the right ventricle. If however, $|\Delta_{PIVCD}|$ is greater than or equal to $\epsilon$, then pacing occurs in the right ventricle wherein the timing of the paced stimulus (or stimuli) follows the equation (Eqn. 5):

$$AV_{RV}=AV_{optimal}-(|\Delta|-\Delta_{PIVCD}) \text{ or}$$

$$PV_{RV}=PV_{optimal}-(|\Delta|-\Delta_{PIVCD}) \quad (5)$$

Thus, Eqn. 5 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 230 ms, $AV_{optimal}$ is 190 ms, $\epsilon$ is 5 ms, PIVCD-LR is 10 ms and PIVCD-RL is 20 ms (better left to right or poorer right to left conduction). In this situation, $|\Delta|$ is |230 ms−280 ms| or 50 ms and $\Delta_{PIVCD}$ is (10 ms−20 ms) or −10 ms. Thus, pacing should occur in the right ventricle with an atrio-ventricular delay as follows:

$$AV_{RV}=190 \text{ ms}-(50 \text{ ms}-(-10 \text{ ms}))=130 \text{ ms}$$

In this situation, the calculated delay of the pacing stimulus (or stimuli) in the right ventricle accounts for conduction issues from the atria to the ventricles and for poor right to left interventricular conduction. Further in this example, if $AR_{LV}$ is 230 ms, then the difference between ventricular activation is approximately 230 ms−130 ms or 100 ms, wherein the right ventricle is activated prior to the left ventricle, which may be referred to as $|\Delta_{actual}|$ which is equal to $|AR_{LV}-AV_{RV}|$.

FIG. 11 shows various, more specific examples related to Scenario II of FIG. 9, wherein at least some delay information is known about paced interventricular conduction delay (PIVCD). In these scenarios, such delay information pertains to delay between a paced event (e.g., V) in one ventricle and a sensed event (e.g., R) in another ventricle. Thus, such delay information pertains to conduction between the right ventricle and the left ventricle.

The more specific examples rely on a comparison between $|\Delta_{PIVCD}|$ and a PIVCD conduction related parameter $\epsilon$. The parameter $\epsilon$ represents an interventricular correction term for conduction between the ventricles and may represent a tolerable limit for conduction heterogeneity. For example, a large $\epsilon$ may be used to tolerate or to not compensate for conduction in one direction being significantly greater than conduction in the other direction.

As shown in FIG. 11, if $AR_{LV}$ and $AR_{RV}$ are greater than $AR_{max}$ (or $PR_{LV}$ and $PR_{RV}$ are greater than $PR_{max}$), $AR_{LV}$ is greater than $AR_{RV}$ and $|\Delta_{PIVCD}|$ is less than $\epsilon$, then pacing occurs in both ventricles wherein $AV_{RV}$ is set to $AV_{optimal}$ and in the left ventricle the timing of the paced stimulus (or stimuli) follows the equation (Eqn. 6):

$$AV_{LV}=AV_{RV}-|\Delta| \text{ or } PV_{LV}=PV_{RV}-|\Delta| \quad (6)$$

Thus, Eqn. 6 ensures that pacing compensates for at least some of the conduction problem associated with the left ventricle. If however, $|\Delta_{PIVCD}|$ is greater than or equal to $\epsilon$, then $AV_{RV}$ is set to $AV_{optimal}$ and pacing occurs in the left ventricle wherein the timing of the paced stimulus (or stimuli) follows the equation (Eqn. 7):

$$AV_{LV}=AV_{RV}-(|\Delta|+\Delta_{PIVCD}) \text{ or}$$

$$PV_{LV}=PV_{RV}-(|\Delta|+\Delta_{PIVCD}) \quad (7)$$

Thus, Eqn. 7 ensures that pacing compensates for at least some of the conduction problem associated with the left ventricle and for at least some of the conduction problem associated with conduction between ventricles.

Consider a situation where $AR_{max}$ is 250 ms, $AR_{LV}$ is 300 ms, $AR_{RV}$ is 260 ms, $AV_{optimal}$ is 180 ms, $\epsilon$ is 5 ms, PIVCD-LR is 10 ms and PIVCD-RL is 20 ms (better left to right or poorer right to left conduction). In this situation, $|\Delta|$ is |300 ms−260 ms| or 40 ms and $\Delta_{PIVCD}$ is (10 ms−20 ms) or −10 ms. Thus, pacing should occur in the left ventricle with an atrio-ventricular delay as follows:

$$AV_{LV}=180 \text{ ms}-(40 \text{ ms}+(-10 \text{ ms}))=150 \text{ ms}$$

In this example, if $AV_{RV}$ is 180 ms, then the difference between ventricular activation is approximately 180 ms−150 ms or 30 ms, wherein the left ventricle is activated prior to the right ventricle, which may be referred to as $\Delta_{actual}$ which is equal to $|AV_{LV}-AV_{RV}|$.

As shown in FIG. 11, if $AR_{RV}$ and $AR_{LV}$ are greater than $AR_{max}$ (or $PR_{RV}$ and $PR_{LV}$ are greater than $PR_{max}$), $AR_{RV}$ is greater than $AR_{LV}$ and $|\Delta_{PIVCD}|$ is less than $\epsilon$, then $AV_{LV}$ is set to $AV_{optimal}$ and pacing occurs in the right ventricle wherein the timing of the paced stimulus (or stimuli) follows the equation (Eqn. 8):

$$AV_{RV}=AV_{LV}-|\Delta| \text{ or } PV_{RV}=PV_{LV}-|\Delta| \quad (8)$$

Thus, Eqn. 8 ensures that pacing compensates for at least some of the conduction problem associated with the right ventricle. If however, $|\Delta_{PIVCD}|$ is greater than or equal to $\epsilon$, then $AV_{LV}$ is set to $AV_{optimal}$ and pacing occurs in the right ventricle wherein the timing of the paced stimulus (or stimuli) follows the equation (Eqn. 9):

$$AV_{RV}=AV_{LV}-(|\Delta|-\Delta_{PIVCD}) \text{ or}$$

$$PV_{RV}=PV_{LV}-(|\Delta|-\Delta_{PIVCD}) \quad (9)$$

Thus, Eqn. 9 ensures that pacing compensates for at least some of the conduction problem associated with the right ventricle and for at least some of the conduction problem associated with conduction between ventricles.

Consider a situation where $AR_{max}$ is 250 ms, $AR_{RV}$ is 280 ms, $AR_{LV}$ is 270 ms, $AV_{optimal}$ is 190 ms, $\epsilon$ is 5 ms, PIVCD-LR is 10 ms and PIVCD-RL is 20 ms (better left to right or poorer right to left conduction). In this situation, $|\Delta|$ is |270 ms−280 ms| or 10 ms and $\Delta_{PIVCD}$ is (10 ms−20 ms) or −10 ms. Thus, pacing should occur in the right ventricle with an atrio-ventricular delay as follows:

$$AV_{RV}=190 \text{ ms}-(10 \text{ ms}-(-10 \text{ ms}))=170 \text{ ms}$$

In this situation, the calculated delay of the pacing stimulus (or stimuli) in the right ventricle accounts for conduction issues from the atria to the ventricles and for poor right to left interventricular conduction. Further in this example, because $AV_{LV}$ is 190 ms, the difference between ventricular activation is approximately 190 ms−170 ms or 20 ms, wherein the right ventricle is activated prior to the left ventricle, which may be referred to as $|\Delta_{actual}|$ which is equal to $|AV_{LV}-AV_{RV}|$.

In the foregoing examples of FIG. 10 and FIG. 11, there is no explicit compensation based on the information shown in the plot 600 of FIG. 6. For example, the exemplary parameter $\alpha$ (e.g., $\alpha=\Delta_{optimal}/\Delta$) does not appear in Eqns. 2 through 9. FIG. 12 exhibits how the parameter $\alpha$ may be used to further enhance cardiac performance in Scenario I and/or Scenario II. In general, the examples of FIG. 12 use an optimal AV delay and use the parameter $\alpha$ to arrive at an optimal interventricular delay.

For $AR_{RV} > AR_{LV}$ (or $PR_{RV} > PR_{LV}$) and pacing in a single ventricle (e.g., Scenario I), the following equation (Eqn. 10) may be used to determine an appropriate $AV_{RV}$:

$$AV_{RV} = AV_{optimal} - \alpha|\Delta| \text{ or } PV_{RV} = PV_{optimal} - \alpha|\Delta| \quad (10)$$

In Eqn. 10 the term $\alpha|\Delta|$ equals or approximates $\Delta_{optimal}$. Thus, a patient's device may deliver therapy using an optimal atrio-ventricular delay in one chamber together with an optimal interventricular delay.

In instances where $\Delta_{PIVCD}$ information is available and an adjustment for interventricular conduction desirable, then the following equation (Eqn. 11) may be used in Scenario I where $AR_{LV} > AR_{RV}$ (or $PR_{LV} > PR_{RV}$):

$$AV_{LV} = AV_{optimal} - \alpha(|\Delta| + \Delta_{PIVCD}) \text{ or}$$

$$PV_{LV} = PV_{optimal} - \alpha(|\Delta| + \Delta_{PIVCD}) \quad (11)$$

For Scenario I where $AR_{RV} > AR_{LV}$ (or $PR_{RV} > PR_{LV}$), the sign of the paced interventricular conduction delay time is switched from "+" to "−", where $\Delta_{PIVCD}$ is defined as PIVCD-LR−PIVCD-RL. Similar equations exist for Scenario II, wherein the parameter $\alpha$ is used to adjust $\Delta$ or the term $|\Delta| \pm \Delta_{PIVCD}$.

While the parameter $\alpha$ was described with respect to echocardiogram data, other techniques may be suitable to determine such a parameter. As already mentioned, the parameter $\alpha$ may depend on or be adjusted based wholly, or in part, on IEGM information acquired in vivo using traditional sensing leads, electrodes and circuitry. Further, a patient may have more than one such parameter. For example, a patient may have an $\alpha_{sleep}$, an $\alpha_{exercise}$, an $\alpha_{normal}$, etc., depending on conditions or states the patient is likely to experience. In such a manner, a detector may detect a condition or state and then select a corresponding $\alpha$. Parameters and/or parameter selection may be based on cardiac information such as QRS and conduction times. For example, if a patient exhibits normal $PR_{RV}$ conduction, a QRS less than approximately 150 ms and excessive $PR_{LV}$ conduction, then $\alpha$ may be set to 0.5 or other value as appropriate. Various sensors are mentioned above with respect to the exemplary device 100 of FIG. 2. Such sensors may provide information for use in determining an $\alpha$ parameter or other parameters suitable for use in adjusting pacing variables.

Various information pertaining to conduction is optionally used to determine, estimate and/or update an optimal atrio-ventricular delay (e.g., $AV_{optimal}$ or $PV_{optimal}$). For example, if $AR_{RV} < AR_{LV}$ or $PR_{RV} < PR_{LV}$, a new optimal atrio-ventricular delay may be determined using the following equation (Eqn. 12):

$$AV_{optimal}(n+1) = AV_{optimal}(n) * (AR_{RV}(n+1)/AR_{RV}(n)) \text{ or}$$

$$AV_{optimal}(n+1) = AV_{optimal}(n) * (PR_{RV}(n+1)/PR_{RV}(n)) \quad (12)$$

If $AR_{LV} < AR_{RV}$ or $PR_{LV} < PR_{RV}$, then $AR_{LV}$ or $PR_{LV}$ could be used to update $AV_{optimal}$. For example, if $AR_{LV}(n+1)$ is 160 ms, $AR_{RV}(n+1)$ is 210 ms, $AV_{optimal}(n)$ is 150 ms and $AR_{LV}(n)$ is 170 ms, then $AV_{optimal}(n+1)$ is approximately 150 ms*(160 ms/170 ms) or 141 ms.

Updating of information such as an $AV_{optimal}$ delay may occur based on a schedule, a number of beats, a change in cardiac condition, etc. For example, if a change of more than 10% occurs in the shorter atrio-ventricular conduction delays over a 1 hour period, then $AV_{optimal}$ is updated. Of course, updating may occur upon a session with a caretaker wherein information is obtained and used to determine $AV_{optimal}$. Further, an exemplary implanted device optionally stores changes in $AV_{optimal}$ which may be subsequently used by a caretaker, for example, to improve therapy, to diagnose cardiac condition, etc.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

Figure 13:
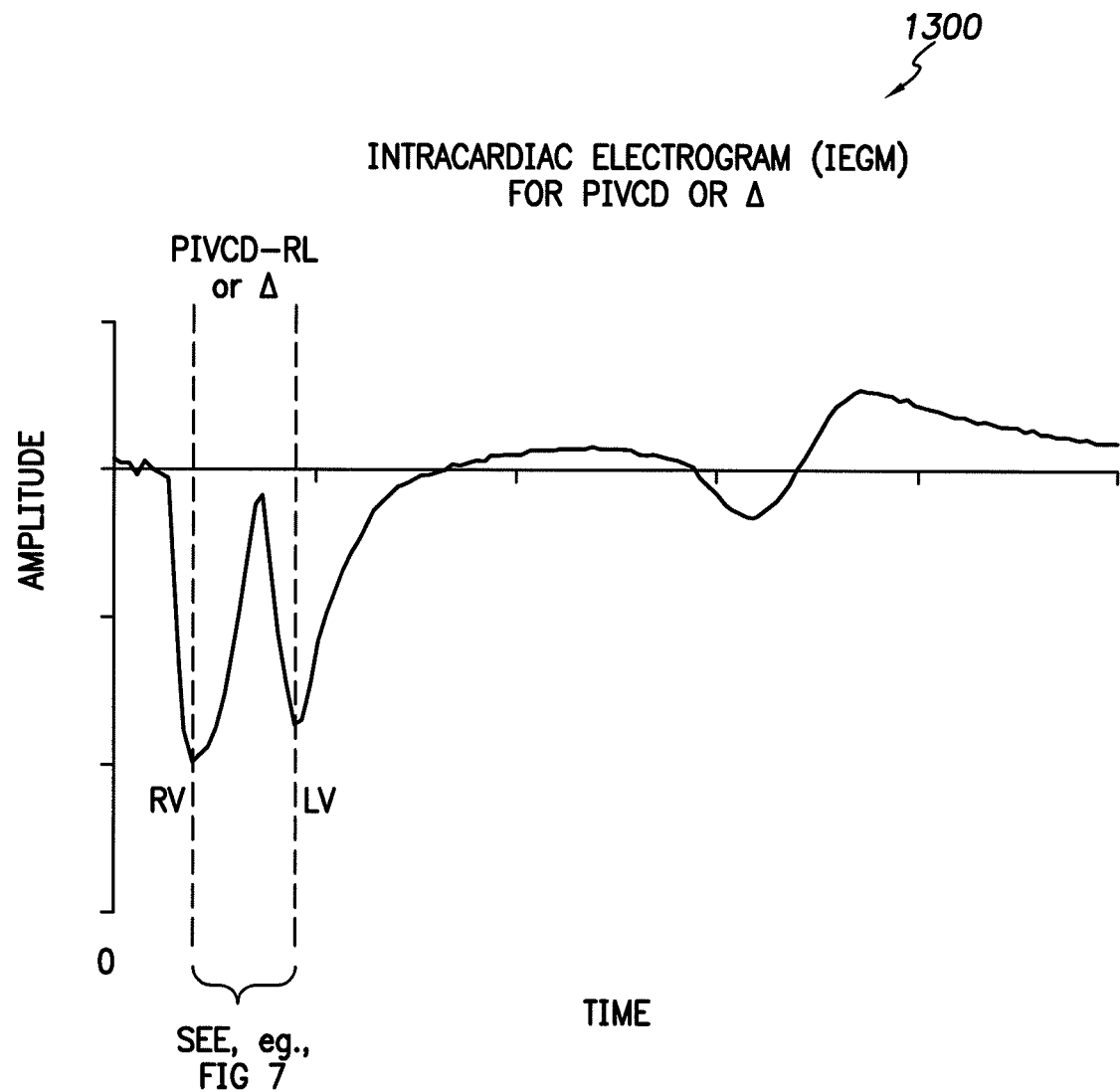
FIG. 13 is an exemplary IEGM plot acquired in a study using a unipolar sensing arrangement for a right ventricular tip electrode and a left ventricular tip electrode having a common electrode.

FIG. 13 shows an exemplary IEGM plot 1300 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle. In this example, the peak-to-peak time delay typically approximates $\Delta$. However, it may approximate PIVCD-RL in the case of FIGS. 7 and 8. If RV is paced at a short AV delay, the time delay from pacing RV to the peak of the conduction to the left ventricle approximates PIVCD-RL. In an alternative example, not shown in FIG. 13, a pacing stimulus was delivered to the right ventricle at a time of approximately 0 ms. This pacing stimulus resulted in capture of the right ventricle and the IEGM showed a corresponding right ventricular evoked response. In this example, the left ventricle was not paced or initially captured by the pace to the right ventricle but after a short delay, the left ventricle depolarized spontaneously due to conduction of the paced event from the right ventricle. Hence, the delay between the right ventricular peak (RV) and the left ventricular peak (LV) approximates a paced interventricular conduction delay from right ventricle to left ventricle (see, e.g., PIVCD-RL of FIG. 7). Thus, the plot 1300 helps to demonstrate a particular exemplary manner in which an implantable device that uses a single sensing amplifier for right and left ventricular sensing channels can determine paced interventricular conduction delay and thus, $\Delta_{PIVCD}$. In addition, such a sensing arrangement may be used to determine a VV delay (e.g., $\Delta$, etc.) based on an intrinsic or a paced atrial event that is then conducted to the left ventricle and the right ventricle.

Further, some implantable devices having sensing and pacing capabilities can deliver a stimulus to one ventricle and then switch to sensing of both ventricles. For example, in the plot 1300, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 14:
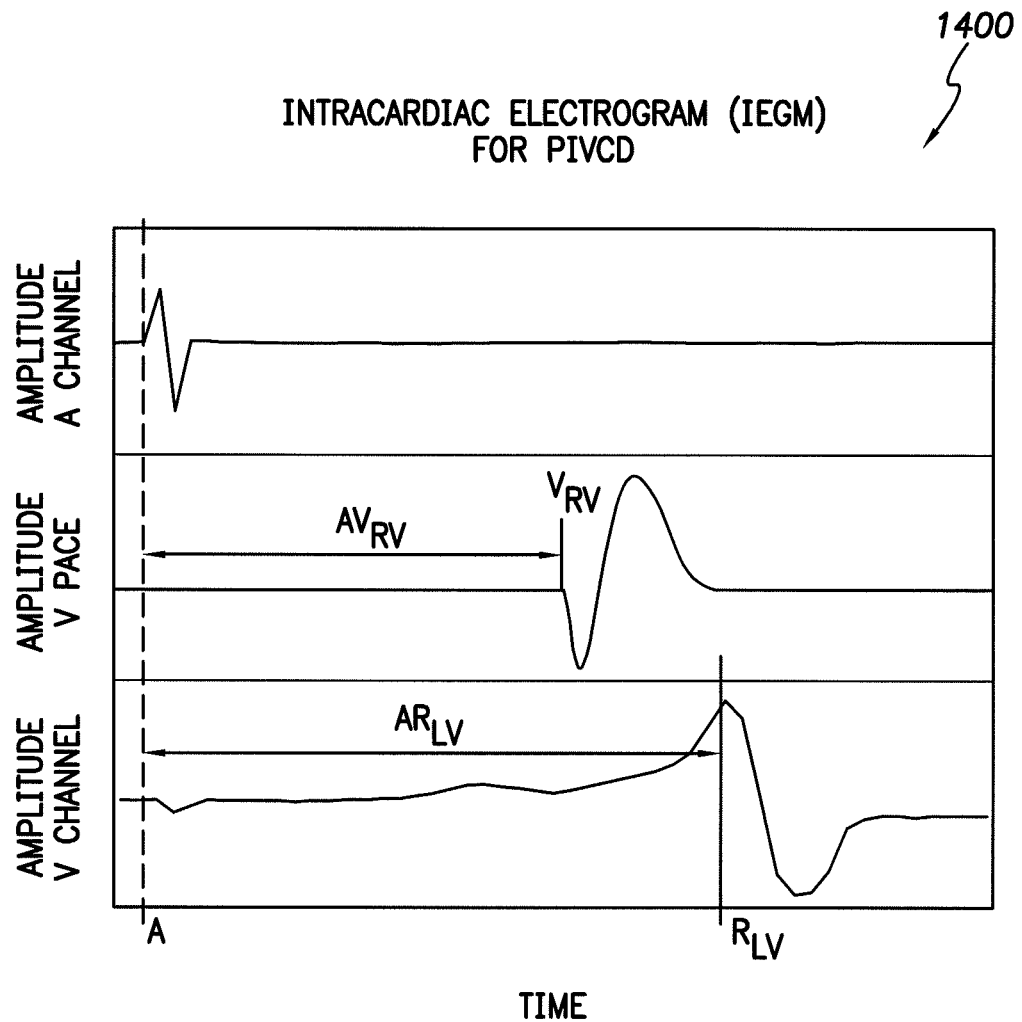
FIG. 14 is an exemplary atrial and ventricular IEGM plot acquired in a study using an implantable device optionally including a switchable channel for RV and LV sensing and/or pacing.

FIG. 14 shows an exemplary IEGM plot 1400 wherein the ventricular IEGM was acquired in a study using an implantable device including switchable channel for RV and LV sensing. Such a device may allow for measurement of $AR_{RV}/PR_{RV}$ and $AR_{LV}/PR_{LV}$ by switching between RV sensing to LV sensing. Accordingly, $\Delta$ may be ascertained. Such a device may also allow for pacing in the right ventricle and/or left ventricle. Further, such a device may ascertain PIVCD-RL and/or PIVCD-LR and optionally $\Delta_{PIVCD}$. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, PIVCD-RL may equal $AR_{LV}$–$AV_{RV}$ or $PR_{LV}$–$PV_{RV}$.

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

Figure 15:
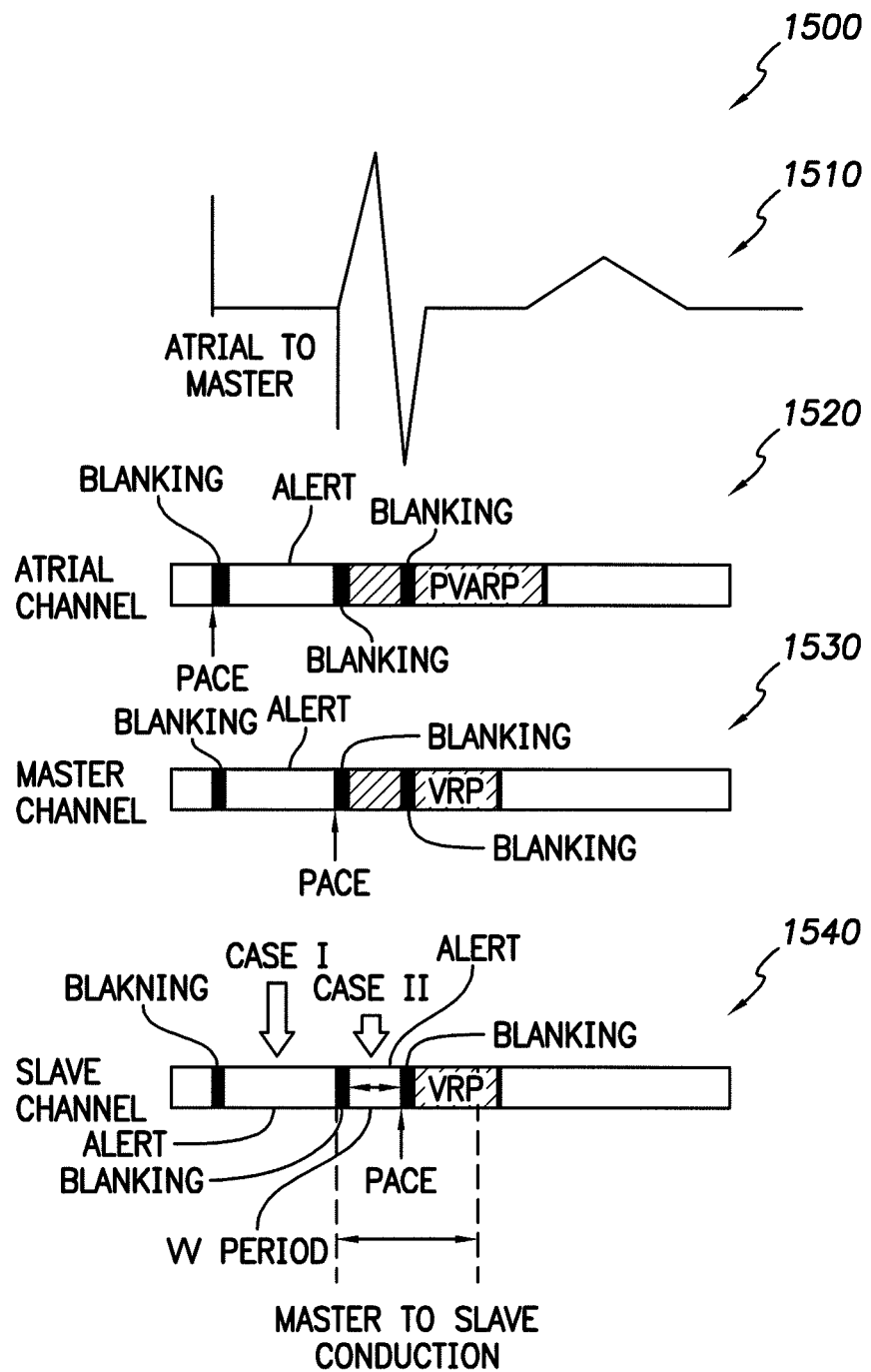
FIG. 15 is an exemplary scheme for triggering and/or inhibiting stimulation in response to sensing of intrinsic activity.

FIG. 15 shows an exemplary scheme 1500 wherein several cases exist for sensing an intrinsic or non-paced event. A waveform 1510 shows an atrial pace, a ventricular pace and a corresponding ventricular waveform (e.g., for a single ventricular sensing channel). An atrial channel 1520 includes various events including an atrial pace event. As shown, the atrial channel 1520 includes an atrial pace blanking period, an alert period, a first ventricular blanking period (e.g., a master ventricle blanking period), a post ventricular atrial refractory period (PVARP), and a second ventricular blanking period (e.g., a slave ventricle blanking period). Some of these periods are optional, depending, for example, on one or more sensed and/or programmed events.

The exemplary scheme 1500 also includes a master ventricular channel 1530. The master ventricular channel 1530 includes an atrial blanking period, an alert period, a master ventricle pace event, a master ventricle blanking period, a ventricular refractory period (VRP, e.g., a master ventricle refractory period), and a second ventricular blanking period (e.g., a slave ventricle blanking period). Various events of the master ventricular channel 1530 coincide or occur in coordination with one or more sensed and/or programmed events and/or periods of one or more other channels. Further, some of the events or periods of the master channel 1530 are optional depending, for example, on one or more sensed and/or programmed events.

The exemplary scheme 1500 also includes a slave ventricular channel 1540. The slave ventricular channel 1540 includes an atrial blanking period, a first alert period, a master blanking period, a second alert period, a slave ventricle pace event, a slave ventricle blanking period, and a ventricular refractory period (VRP, e.g., a slave ventricle refractory period). Various events of the slave ventricular channel 1540 coincide or occur in coordination with one or more sensed and/or programmed events and/or periods of one or more other channels. Further, some of the events or periods of the slave channel 1540 are optional, depending, for example, on one or more sensed and/or programmed events.

Two particular cases are shown with respect to the slave channel 1540 that relate to detection or sensing of activity in the slave ventricle prior to delivery of a master ventricle pace event (e.g., Case I) and detection or sensing of activity in the slave ventricle after delivery of a master ventricle pace event (e.g., Case II). In Case I, the slave ventricle activity occurs in an alert period that lies somewhere between the atrial pace event (or detection/sensing of an intrinsic atrial event) and the scheduled delivery time of a master ventricle pace event. In response to Case I, an exemplary method, device and/or system may deliver a master ventricle pace and/or inhibit any scheduled slave ventricle pace. In delivering a pace to a master ventricle, the exemplary scheme 1500 may act via sensing or detecting to ensure that the pace avoids any vulnerable period (e.g., T wave, etc.). An alternative choice is also to inhibit master channel. In Case II, the slave ventricle activity occurs in an alert period that lies somewhere between the master ventricle pace event and a scheduled slave ventricle pace event, for example, the alert period may be coextensive with a VV delay. In response to Case II, an exemplary method, device and/or system may inhibit the scheduled slave ventricle pace event.

The exemplary slave channel 1540 also shows a master ventricle to slave ventricle conduction period (e.g., as determined by PIVCD-RL, PIVCD-LR, etc.). In this example, the ventricular refractory period extends to times greater than the master ventricle to slave ventricle conduction period as measured from delivery of a master pace event. The refractory period may be represented by the following equation (Eqn. 13):

$$VRP_{Slave\ Ventricle} > PIVCD\text{-}RL \text{ or } PIVCD\text{-}LR - VV \qquad (13)$$

In Eqn. 13, the $VRP_{slave\ Ventricle}$ follows the scheduled slave ventricle pace event.

Various schemes that include one or more features of the exemplary scheme 1500 may help to avoid issues relating to double counting, which may trigger tachycardia therapy. For example, in some implantable devices, a pacing stimulus delivered to one ventricle may be sensed in the other ventricle and be classified as a fast ventricular rhythm (i.e., double counting). In the exemplary scheme 1500, a pacing stimulus generally occurs in the other ventricle before the paced stimulus can be conducted to that ventricle. In other words, the desired VV delay is less than any inherent interventricular conduction and thus, the probability of sensing ventricular paced beats in the alert interval is quite small. In addition, if an auto capture algorithm is used to detect capture of a paced stimulus; then, double counting may be avoided based on such detection.

Figure 16:
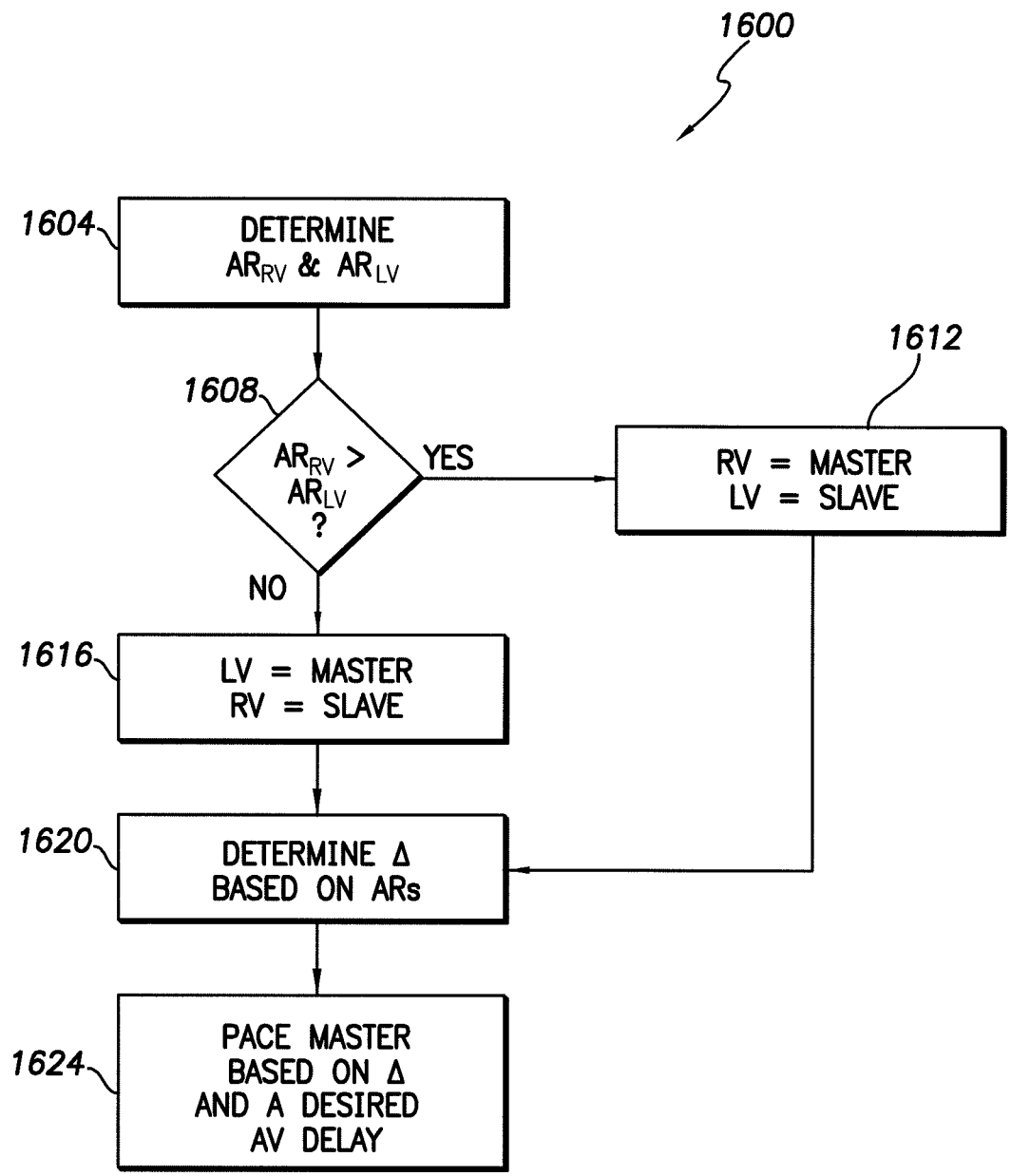
FIG. 16 is a block diagram of an exemplary method for ventricular pacing based on an $AR_{RV}$ time and an $AR_{LV}$ time without an optional correction term.

FIG. 16 shows a block diagram of an exemplary method 1600 for ventricular pacing. In a determination block 1604, an implantable device determines an $AR_{RV}$ time and an $AR_{LV}$ time or equivalent times wherein one or both rely on detection of an intrinsic atrial event. A decision block 1608 follows wherein a decision is made as to whether $AR_{RV}$ is greater than $AR_{LV}$. If $AR_{RV}$ exceeds $AR_{LV}$, then in a set block 1612, the right ventricle is set to the master and the left ventricle is set to the slave. If $AR_{LV}$ exceeds $AR_{RV}$, then in a set block 1616, the left ventricle is set to the master and the right ventricle is set to the slave. Both set blocks 1612, 1616 continue in a determination block 1620 which determines a $\Delta$ value based on the $AR_{RV}$ and $AR_{LV}$ times. A pace master block 1624 follows wherein the master ventricle is paced based on the $\Delta$ and a desired AV delay. The desired AV delay may be determined, for example, based on an echocardiogram or other study. The AV delay is optionally determined by an implantable device based on sensed information.

Thus, as described with respect to FIG. 16, such an exemplary method includes determining an atrial to ventricular activation time for a right ventricle; determining an atrial to ventricular activation time for a left ventricle; and determining a pacing sequence that paces the right ventricle prior to activation of the left ventricle if the time for the right ventricle exceeds the time for the left ventricle or that paces the left ventricle prior to activation of the right ventricle if the time for the left ventricle exceeds the time for the right ventricle wherein pacing of the prior activated ventricle occurs based at least in part on a difference between the time for the right ventricle and the time for the left ventricle and a desired atrio-ventricular delay. In some instances, an interventricular delay may be used instead of, or in addition, to one or more atrial to ventricular activation times.

Figure 17:
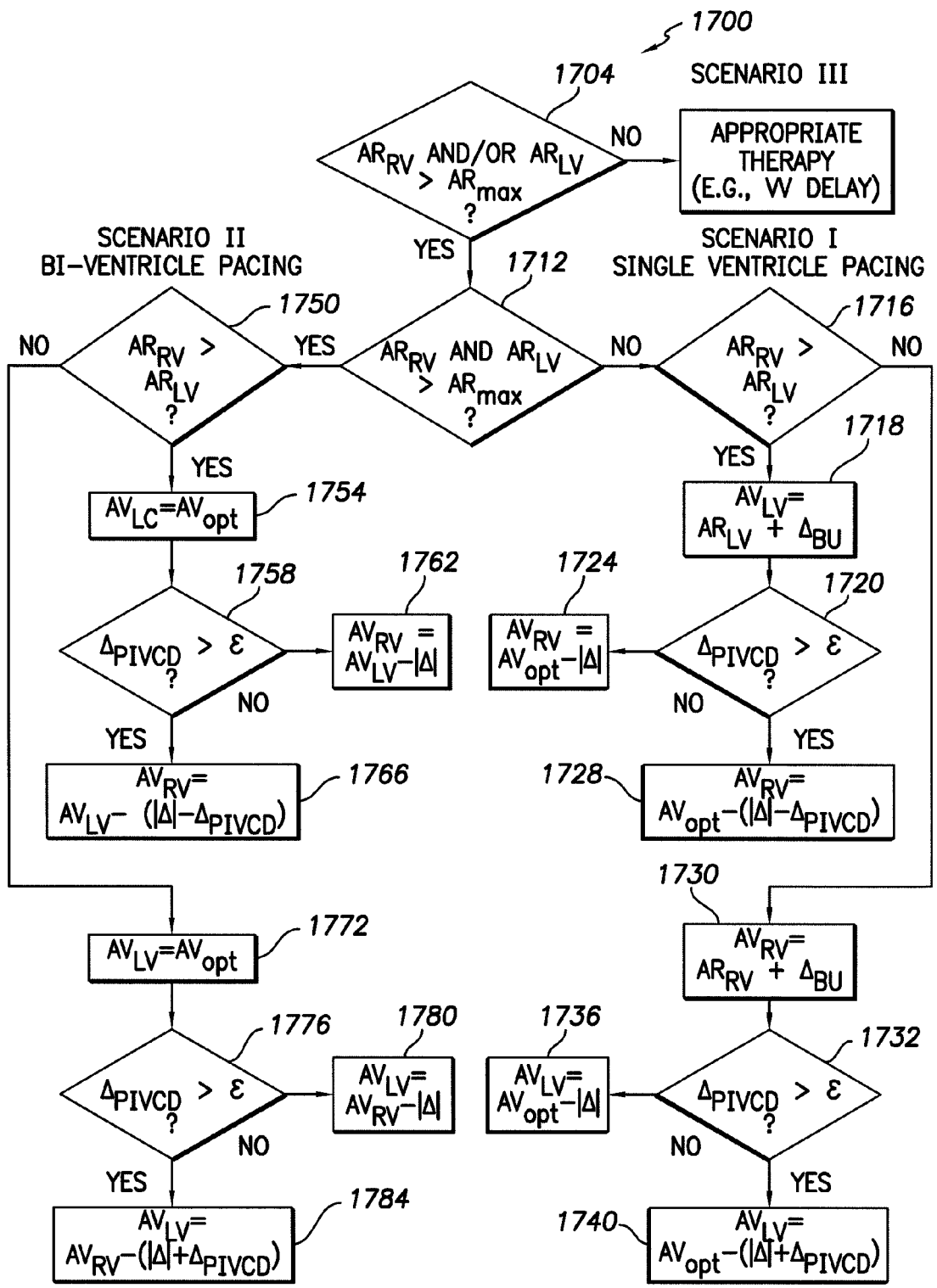
FIG. 17 is a block diagram of an exemplary method for ventricular pacing.

FIG. 17 shows a block diagram of an exemplary method 1700. While the method 1700 pertains to atrial pacing, such a method may omit atrial pacing (e.g., rely on an intrinsic atrial activity, etc.) and/or include atrial pacing and intrinsic atrial activity, etc. (e.g., PR, AR, AV, and/or PV). The exemplary method 1700 includes Scenarios I, II and III as presented above. For example, in a decision block 1704 a decision is made as to whether $AR_{RV}$ and/or $AR_{LV}$ have exceeded a predetermined $AR_{max}$ value. If neither value exceeds $AR_{max}$, then Scenario III follows in no ventricular pacing or other appropriate therapy block 1708. Other appropriate therapy optionally includes therapy that achieves a desirable VV delay. If however one or both values exceed $AR_{max}$, then the method 1700 continues in another decision block 1712. The decision block 1712 decides whether $AR_{RV}$ and $AR_{LV}$ have exceeded $AR_{max}$. If both values do not exceed $AR_{max}$, then single ventricular pacing occurs, for example, Scenario I. If both values exceed $AR_{max}$, then bi-ventricular pacing occurs, for example, Scenario II.

Scenario I commences with a decision block 1716 that decides if $AR_{RV}$ is greater than $AR_{LV}$. If $AR_{RV}$ exceeds $AR_{LV}$, then single ventricular pacing occurs in the right ventricle (e.g., right ventricle master). If $AR_{RV}$ does not exceed $AR_{LV}$, then single ventricular pacing occurs in the left ventricle (e.g., left ventricle master).

For right ventricular pacing, the method 1700 continues in a back-up pacing block 1718 where $AV_{LV}$ is set to $AR_{LV}$ plus some back-up time (e.g., $\Delta_{BU}$). The block 1718, while optional, acts to ensure that pacing will occur in the left ventricle if no activity occurs within some given interval. The method 1700 then continues in a decision block 1720 where, if appropriate, a decision is made as to whether $\Delta_{PIVCD}$ exceeds some value $\epsilon$. If the decision block 1720 decides that $\Delta_{PIVCD}$ is small, then in a set block 1724, the method 1700 sets the $AV_{RV}$ delay to $AV_{optimal}$-|Δ|. Otherwise, the method 1700 uses $\Delta_{PIVCD}$ as a correction factor in a set block 1728, which sets $AV_{RV}$ delay to $AV_{optimal}$-(|Δ|-$\Delta_{PIVCD}$).

For left ventricular pacing, the method 1700 continues in a back-up pacing block 1730 where $AV_{LV}$ is set to $AR_{LV}$ plus some back-up time (e.g., $\Delta_{BU}$). The block 1730, while optional, acts to ensure that pacing will occur in the left ventricle if no activity occurs within some given interval. The method 1700 then continues in a decision block 1732 where, if appropriate, a decision is made as to whether $\Delta_{PIVCD}$ exceeds some value $\epsilon$. If the decision block 1732 decides that $\Delta_{PIVCD}$ is small, then in a set block 1736, the method 1700 sets the $AV_{LV}$ delay to $AV_{optimal}$-|Δ|. Otherwise, the method 1700 uses $\Delta_{PIVCD}$ as a correction factor in a set block 1740, which sets $AV_{LV}$ delay to $AV_{optimal}$-(|Δ|+$\Delta_{PIVCD}$).

If the decision block 1712 decides that bi-ventricular pacing is appropriate, for example, Scenario II, then the method 1700 continues in a decision block 1750, which that decides if $AR_{RV}$ is greater than $AR_{LV}$. If $AR_{RV}$ exceeds $AR_{LV}$, then bi-ventricular pacing occurs wherein the right ventricle is the master (e.g., paced prior to the left ventricle or sometimes referred to as left ventricle slave). If $AR_{RV}$ does not exceed $AR_{LV}$, then bi-ventricular pacing occurs wherein the left ventricle is the master (e.g., paced prior to the right ventricle or sometimes referred to as right ventricle slave).

For right ventricular master pacing, the method 1700 continues in a set block 1754 which sets $AV_{LV}$ to $AV_{optimal}$. A decision block 1758 follows where, if appropriate, a decision is made as to whether $\Delta_{PIVCD}$ exceeds some value $\epsilon$. If the decision block 1758 decides that $\Delta_{PIVCD}$ is small, then in a set block 1762, the method 1700 sets the $AV_{RV}$ delay to $AV_{LV}$-|Δ|. Otherwise, the method 1700 uses $\Delta_{PIVCD}$ as a correction factor in a set block 1766, which sets $AV_{RV}$ delay to $AV_{LV}$-(|Δ|-$\Delta_{PIVCD}$).

For left ventricular master pacing, the method 1700 continues in a set block 1772 which sets $AV_{RV}$ to $AV_{optimal}$. A decision block 1776 follows where, if appropriate, a decision is made as to whether $\Delta_{PIVCD}$ exceeds some value $\epsilon$. If the decision block 1776 decides that $\Delta_{PIVCD}$ is small, then in a set block 1780, the method 1700 sets the $AV_{LV}$ delay to $AV_{RV}$-|Δ|. Otherwise, the method 1700 uses $\Delta_{PIVCD}$ as a correction factor in a set block 1784, which sets $AV_{LV}$ delay to $AV_{RV}$-|Δ|+$\Delta_{PIVCD}$).

If a parameter such as the aforementioned a parameter is available, then such a parameter is optionally used to further adjust and/or set one or more delays, as appropriate (see, e.g., Eqns. 10 and 11).

Figure 18:
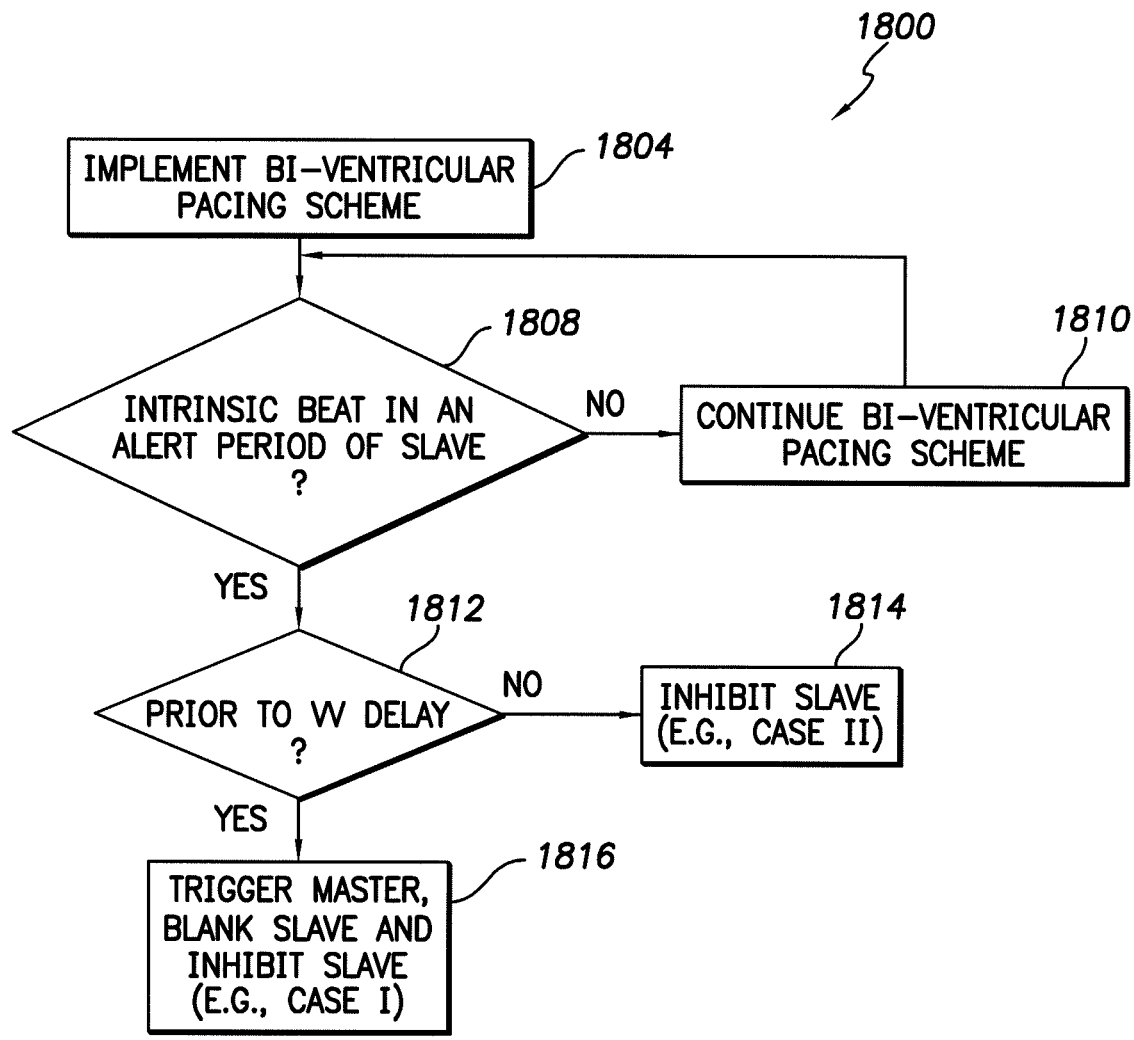
FIG. 18 is a block diagram of an exemplary method corresponding to the scheme of FIG. 15 for immediate delivery of a master stimulation and/or inhibition of a slave stimulation based on the presence and timing of intrinsic beats.

FIG. 18 shows a block diagram of an exemplary method 1800 that optionally relates to the exemplary scheme 1500 of FIG. 15. In an implementation block 1804, a bi-ventricular pacing scheme is implemented. A decision block 1808 follows wherein a decision is made as to whether an intrinsic event has occurred in an alert period of a ventricular channel (e.g., a slave channel). If the decision block 1808 decides that no activity or event has occurred in an alert period, then the method 1800 proceeds to a continuation block 1810 where the bi-ventricular pacing scheme continues where, as appropriate, the method 1800 flows back to the decision block (e.g., after certain programmed events, etc.). However, if the decision block 1808 decides that an intrinsic event occurred in an alert period, then another decision block 1812 follows. The decision block 1812 decides if the activity or event occurred prior to a VV delay period (e.g., a $\Delta_{programmed}$). If the decision block 1812 decides that the occurrence was not prior to a VV delay period then the method 1800 continues in an inhibition block 1814 that inhibits delivery of a pace event to a ventricle (e.g., to a slave ventricle, see Case II of FIG. 15). However, if the decision block 1812 decides that the occurrence was prior to a VV delay period then the method 1800 continues in a trigger, blank and inhibition block 1816. The trigger, blank and inhibition block 1816 acts to trigger delivery of a pace to a ventricle (e.g., a master ventricle), to initiate one or more blanking periods (e.g., atrial and/or ventricular), and to inhibit delivery of a pace to another ventricle (e.g., a slave ventricle).

Of course, an alert period for a master ventricular channel may exist wherein an intrinsic event in the master ventricle causes inhibition of a scheduled pace event in the master ventricle and causes an update in the timing of a scheduled slave pace event. For example, if an intrinsic event is sensed or detected in the master ventricle, then the VV delay may commence in response thereto. Such an exemplary method would act to preserve the VV delay (e.g., $\Delta_{programmed}$) to ensure appropriate timing of contractions in left and right ventricles.

Various exemplary methods, devices and/or systems include setting an interchamber delay between a master chamber and a slave chamber. For example, an interventricular delay may determine timing of ventricular events while an interatrial delay may determine timing of atrial events.

Accordingly, an exemplary method includes setting an interchamber delay between a master chamber and a slave chamber, sensing for cardiac activity, if the sensing senses intrinsic activity in the slave chamber, determining whether the intrinsic activity occurred during the interchamber delay, and if the intrinsic activity occurred before the interchamber delay, immediately delivering stimulation to the master chamber.

With respect to the ventricles, an exemplary method includes setting an interventricular (VV) delay between a master ventricle and a slave ventricle (e.g., setting $\Delta_{programmed}$) and sensing for ventricular activity. If activity is sensed in the slave ventricle prior to the VV delay period and hence prior to delivery of a pace to the master ventricle, then immediately delivering stimulation to the master ventricle and inhibiting delivery of stimulation to the slave ventricle. If activity is sensed in the slave ventricle after delivery of stimulation to the master ventricle and prior to expiration of the VV delay, then the exemplary method may inhibit delivery of stimulation to the slave ventricle. Such a method optionally includes adjusting the ventricular refractory period in the slave ventricle channel to be greater than the appropriate PIVCD minus VV. PIVCD could be either PIVCD-LR or PIVCD-RL or average of the two.

An exemplary implantable device includes a power supply, a processor, a lead including one or more electrodes capable of being positioned proximate to a master ventricle, a lead including one or more electrodes capable of being positioned proximate to a slave ventricle, and control logic, executable through use of the processor, to set an interventricular delay between the master ventricle and the slave ventricle and to call for immediate delivery of stimulation to the master ventricle using the lead proximate to the master ventricle upon detection of intrinsic activity in the slave ventricle prior to the interventricular delay (e.g., prior to delivery of stimulation to the master ventricle). Such control logic optionally inhibits delivery of stimulation to the slave ventricle.

Various exemplary methods, devices and/or systems may consider instances where normal atrio-ventricular conduction exists for one ventricle. For example, if an atrio-ventricular conduction time for the right ventricle does not exceed one or more limits representative of normal conduction, then the atrio-ventricular time for the right ventricle may serve as a basis for determining an appropriate time for delivery of stimulation to the left ventricle (or vice versa). The following equation (Eqn. 14) may be used in such a situation:

$$AV_{LV}=AR_{RV}-|\Delta| \text{ or } PV_{LV}=PR_{RV}-|\Delta| \tag{14}$$

With respect to backup pulses, a backup pulse (e.g., for purposes of safety, etc.) may be set according to the following equation (Eqn. 15):

$$AV_{RV}=AR_{RV}+|\gamma| \text{ or } PV_{RV}=PR_{RV}+|\gamma| \tag{15}$$

Of course, administration of a backup pulse may occur upon one or more conditions, for example, failure to detect activity in the particular ventricle within a given period of time. In Eqn. 15, the parameter $\gamma$ is a short time delay, for example, of approximately 5 ms to approximately 10 ms.

According to Eqn. 14, there may not be an a priori need for a particular $AV_{optimal}$ or $PV_{optimal}$. Instead, a need may exist for one or more limits to determine if a sensed AR or PR may be considered normal or acceptable. Further, in such exemplary methods, devices and/or systems, an alert period may be implemented wherein sensing or detection of an intrinsic event in a channel associated with the scheduled pace event causes inhibition of the pace event. For example, if an alert period exist prior to the scheduled pace event and intrinsic activity is detected then inhibition of the pace event may occur, which may act to conserve energy of an implanted device. However, if the alert period expires without sensing or detecting intrinsic activity, the back up pacing pulse in the right ventricle is delivered at $AV_{RV}$ and $AV_{LV}$ will be kept scheduled.

In many instances, heart condition will affect $AR_{RV}$ and $AR_{LV}$, and PIVCD, which, in turn, may affect an existing optimal VV delay setting. Various exemplary methods, devices and/or systems include triggering of an algorithm to update an existing optimal VV delay according to a predetermined time or event period or activity sensors for exercise, resting, etc. An exemplary device may include a learning method that learns based on differences in conduction times (e.g., $AR_{RV}$ and $AR_{LV}$, PIVCD, etc.) such that parameters associated with different heart demands can be stored. The exemplary learning method may then extract such learned or other parameters to set an optimal VV delay.

In the aforementioned learning example, if the device learns on the basis of different cardiac demands, the device may adjust AV delay and/or VV delay and/or learn a new AV delay and/or VV delay upon a change in cardiac demand. According to this example, use of external measurement or sensing equipment (e.g., echocardiogram, etc.) is optional. Further, use of internal measurement or sensing equipment for sensing pressure or other indicators of hemodynamic performance is optional. Again, adjustment and learning may rely on IEGM information and/or cardiac other rhythm information.

An exemplary method relies on an atrial to right ventricular conduction time, an atrial to left ventricular conduction time and a α parameter, for example, as described above, to determine an optimal AV delay and/or VV delay. Another exemplary method relies on an atrial to right ventricular conduction time, an atrial to left ventricular conduction time and a limit that may be used to decide whether one or more of the conduction times are acceptable. In these examples, an interventricular conduction time may be used in lieu of an atrial to ventricular conduction time, for example, where ventricular activity originates with a common atrial event.

According to various exemplary methods, devices and/or systems, information acquired (e.g., sensed, detected and/or determined) may be used to diagnose cardiac condition. For example, an exemplary method may track AV delays and/or VV delays over time. Such information may then be used to determine subsequent therapy.

Various exemplary methods, devices and/or systems include determining an optimal interventricular delay (e.g., $\Delta_{optimal}$) using a modality such as an echocardiogram. While an internal echocardiogram or implantable hemodynamic sensors may be available or become available and be able to measure such optimal delays for a variety of patient circumstances (e.g., sleep, exercise, etc.), an exemplary method, device and/or system includes use of internal sensors to measure and/or update such an optimal delay and/or to determine values for one or more parameters related to an optimal delay. For example, a blood pressure sensor (e.g., aortic arch, etc.) may be used to determine or to update an optimal delay. Further, information may be collected over a period of time to determine heart condition (e.g., deterioration, improvement, etc.).

In general, an optimal interventricular delay will change as demand and/or heart conditions change. Thus, an exemplary method may determine an optimal interventricular delay during sleep on a nightly, a weekly or some other basis. Such an exemplary method may determine an optimal interventricular delay within a matter of minutes (e.g., approximately 5 heart beats). Such an exemplary method may be triggered according to a change in heart rate or some other parameter related to heart condition. Over time or at time of programming, an exemplary device may store one or more optimal interventricular delays as a function of heart rate, heart condition, etc., and then implement a selected delay from the stored delays upon occurrence of a rate, condition, etc., or a change in rate, condition, etc. Such dynamic control of interventricular delay can improve cardiac performance and potentially allow for an improvement in patient quality of life (e.g., allow for a broader range of patient activity). If after some predetermined period of time or upon occurrence of a particular condition, an exemplary device may indicate a need for a more rigorous determination, for example, via an echocardiogram.

Various exemplary methods, devices, systems, etc., optionally rely on interference between an intrinsic stimulus and a non-intrinsic stimulus or between two non-intrinsic stimuli. A common form of interference is known as "fusion". While various aforementioned examples may aim to avoid fusion, other examples deliberately seek the occurrence of fusion.

Fusion is typically characterized by a wave complex formed by depolarization of the myocardium initiated by two different foci, commonly a non-intrinsic stimulus as from a pacemaker or ICD and an intrinsic stimulus. Again, as described herein, fusion may also result from two non-intrinsic stimuli. Table 1, below, sets forth various fusion scenarios where stimuli and/or consequences thereof may cause fusion.

TABLE 1

Exemplary Fusion Scenarios

| Scenario | Stimulus | Fusion Chamber | Parameters |
|---|---|---|---|
| 1 | P or A to RV; pace RV | RV | $AVF_{RV}/PVF_{RV}$ |
| 2 | P or A to LV; pace LV | LV | $AVF_{LV}/PVF_{LV}$ |
| 3 | P or A to RV conduct to LV; pace LV | LV | Various |
| 4 | P or A to LV conduct to RV; pace RV | RV | Various |
| 5 | RV pace conduct to LV; pace LV | LV/RV | VVF-RL $AVF_{RV}/PVF_{RV}$ |
| 6 | LV pace conduct to RV; Pace RV | RV/LV | VVF-LR $AVF_{LV}/PVF_{LV}$ |

In Table 1, Scenario 1 is for fusion in the right ventricle where a paced stimulus to the right ventricle fuses with an intrinsic or non-intrinsic atrial stimulus conducted to the right ventricle; Scenario 2 is for fusion in the left ventricle where a paced stimulus to the left ventricle fuses with an intrinsic or non-intrinsic atrial stimulus conducted to the left ventricle; Scenario 3 is for fusion in the left ventricle where a paced stimulus to the left ventricle fuses with an intrinsic or non-intrinsic atrial stimulus conducted to the right ventricle and is delayed in conduction to the left ventricle (e.g., where left bundle branch block may exist and delay conduction of the atrial stimulus to the left ventricle) (additional parameters may include $AR_{RV}$ or $PR_{RV}$ and ($AVF_{LV}-S_{RV}$) or ($PVF_{LV}-S_{RV}$), where $S_{RV}$ is a sensed right ventricular R wave); Scenario 4 is for fusion in the right ventricle where a paced stimulus to the right ventricle fuses with an intrinsic or non-intrinsic atrial stimulus conducted to the left ventricle and is delayed in conduction to the right ventricle (e.g., where right bundle branch block may exist and delay conduction of the atrial stimulus to the right ventricle) (additional parameters may include $AR_{LV}$ or $PR_{LV}$ and ($AVF_{RV}-S_{LV}$) or ($PVF_{RV}-S_{LV}$), where $S_{LV}$ is a sensed left ventricular R wave)); Scenario 5 is for fusion in the left ventricle where a paced stimulus to the left ventricle fuses with a paced stimulus to the right ventricle that subsequently conducts to the left ventricle and optionally for fusion in the right ventricle where the paced stimulus to the right ventricle fuses with an intrinsic or non-intrinsic atrial stimulus; and Scenario 6 is for fusion in the right ventricle where a paced stimulus to the right ventricle fuses with a paced stimulus to the left ventricle that subsequently conducts to the right ventricle and optionally for fusion in the left ventricle where the paced stimulus to the left ventricle fuses with an intrinsic or non-intrinsic atrial stimulus. Thus, Scenarios 5 and 6 can allow for detection of fusion in both ventricles.

Table 1 also shows various parameters that may be determined for the various scenarios. AVF and PVF refer to surrogates or substitutes for AR and PR and VVF-RL and VVF-LR refer to surrogates or substitutes for PIVCD-RL and PIVCD-LR, which are discussed elsewhere herein. Where "various" is listed, sensing and/or other circumstances may determine which parameters may be determined or estimated. In the scenarios 3 and 4, an AR or PR may be determined for one ventricle and an AVF or PVF for the other ventricle.

Various exemplary methods, devices, systems, etc., optionally rely on occurrence of fusion or other interference to determine one or more pacing parameters. In particular, a variety of techniques may be used to analyze cardiac activity for fusion or other interference. Such techniques include traditional fusion detection techniques that rely on slope, amplitude, morphology, etc. For example, morphology discrimination may be used to detect fusion. Morphology discrimination typically relies on "dynamic template matching" to discriminate between normal and abnormal events (e.g., fusion, intrinsic depolarization, non-intrinsic depolarization, etc.), which may be present in sensed cardiac activity. Morphology discrimination enables a device to examine multiple characteristics of an electrogram (e.g., sensed cardiac activity), as opposed to techniques which may look only at a complex's width, amplitude and/or slew rate; however, such techniques may be used in conjunction with or as alternatives to one or more morphology discrimination techniques. Morphology discrimination allows for a comparison between a complex, or portion thereof, and a template. For example, morphology discrimination may compare a last acquired complex with a predetermined physician-selected patient-specific template. In commercially available implementations of morphology discrimination (MD), a MD algorithm is normally disabled in the setting of a delivered output pulse. In contrast, various exemplary methods described herein may allow for morphology discrimination or other signal characterization following delivery of an output pulse.

Some morphology discrimination techniques allow for automatic template update whereby a periodic evaluation of a stored template occurs followed by an update, which may be needed, for example, to accommodate changes in a therapy, a patient's rhythm and/or signal characteristics. These techniques allow for modification of a template and/or replacement of a template.

An exemplary morphology detection scenario may include a template for a "normal" waveform and a sensed waveform where the template and the waveform have corresponding time bounds. Morphology discrimination may compare any portion of the sensed waveform with the template. A comparison may determine whether the sensed waveform deviates significantly from the template at one or more points within the time bounds.

Another technique involves use of an integral or area of a signal over time. For example, a depolarization integral based on sampling a polarization signal over time (e.g., within a sampling window) may be used to determine whether fusion occurred. An area or integral value may be compared to a limit to determine whether fusion occurred. With respect to a sampling window, an exemplary window may extend about 80 ms from the delivery of a cardiac stimulus. Certain signal information may be ignored, sensing parameters adjusted, the timing or duration of the window tailored, etc., to improve detection of fusion.

An exemplary method may ensure that the stimulation energy and timing are sufficient to capture, as evidenced by an evoked response. For example, such an exemplary method may commence immediately after a capture threshold assessment test has been performed or it may wait until a capture threshold assessment test has been performed. An evoked response signal acquired during a capture assessment test for an adequate threshold may then be used as a standard. For example, if a subsequent integral that is not greater than 60% of the standard, then this may indicate fusion or a sufficiently diminished signal for purposes of determining one or more pacing parameters.

An exemplary method may alternate between a normally timed pacing stimulus and one aimed at causing fusion. According to such a method, if the normally timed pacing stimulus does not cause an evoked response, then the capture threshold may have changed. Under such circumstances, the "fusion" test should be halted until capture is ensured. Alternatively, a fusion test may use a high energy level (e.g., back-up level or other elevated level).

Figure 19:
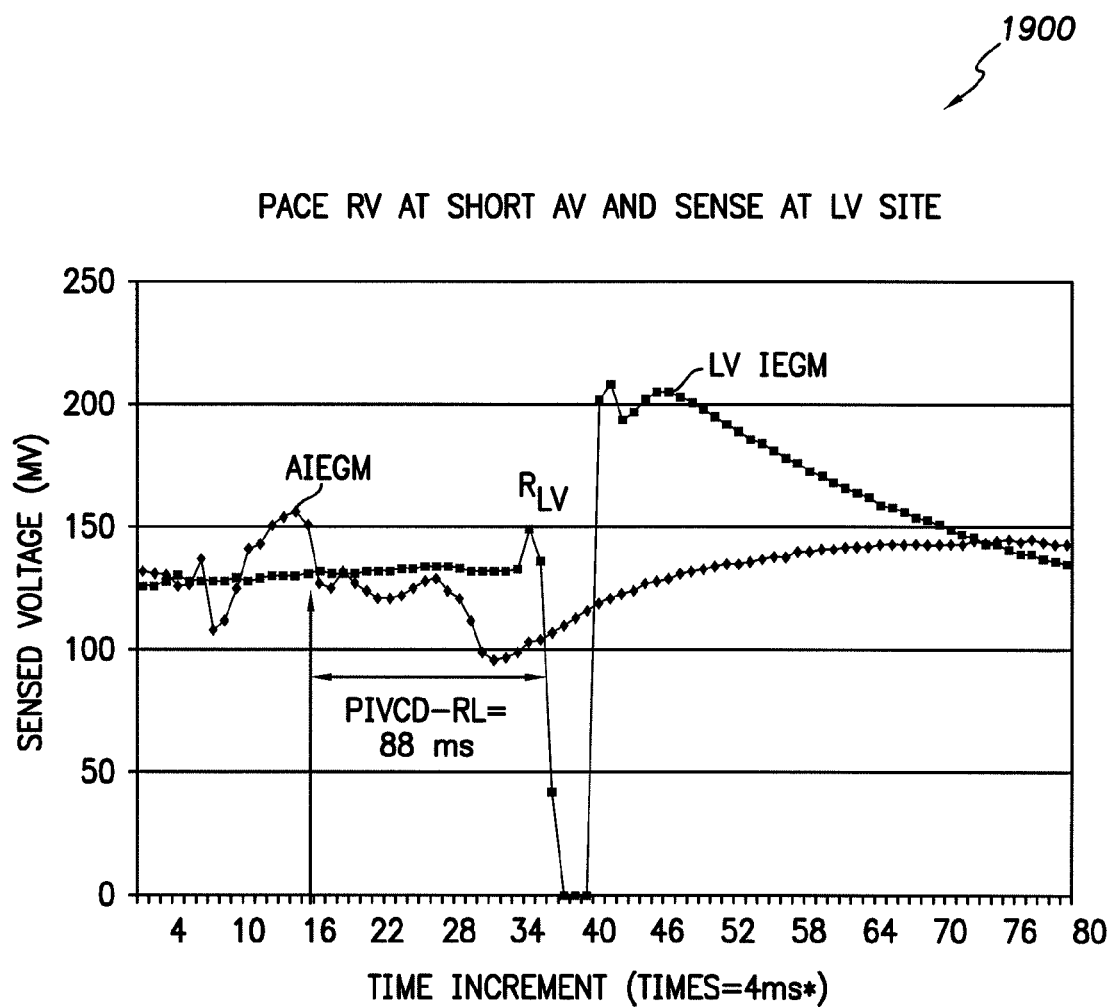
FIG. 19 is an exemplary plot of sensed voltage versus time for right ventricular stimulation and corresponding left ventricular depolarization.

FIG. 19 shows an exemplary plot 1900 of sensed cardiac activity versus time. The sensed cardiac activity includes activity sensed in the atrium and activity sensed in the left ventricle. A short $AV_{RV}$ delay is selected and pacing occurs in the right ventricle according to the selected $AV_{RV}$ delay. Conduction of the right ventricular pacing stimulation then causes a response in the left ventricle at a later time. The time difference between delivery of the right ventricular pacing stimulation and detection of the left ventricular R wave or QRS complex ($R_{LV}$) is referred to as the paced interventricular conduction delay from the right ventricle to the left ventricle (PIVCD-RL). A corresponding time difference also exists between the left ventricle and the right ventricle (PIVCD-LR). Another time difference, $\Delta_{PIVCD}$, may be calculated as the difference between PIVCD-RL and PIVCD-LR.

In the example of plot 1900, PIVCD-RL is approximately 88 ms and can be readily determined from the data. In particular, $R_{LV}$ has a large deviation in sensed voltage where the downward deviation from baseline reaches a sensing or detection limit (e.g., reaches a limit of an analog-to-digital converter). In general, a short AV delay avoids interference from a stimulation wavefront conducted to the ventricles from one or both atria (e.g., conducted via the AV node), which could arrive in the left ventricle earlier than a wavefront from the right ventricular. Such a wavefront could cause fusion in the right ventricle or the left ventricle. For the example of plot 1900, in the right ventricle, fusion could occur between the paced stimulation and conducted atrial stimulation while, in the left ventricle, fusion could occur between the wavefront from the right ventricle and conducted atrial stimulation. As described herein, another form of fusion may occur between paced stimulation in the right ventricle and paced stimulation in the left ventricle (see, e.g., Table 1).

Figure 20:
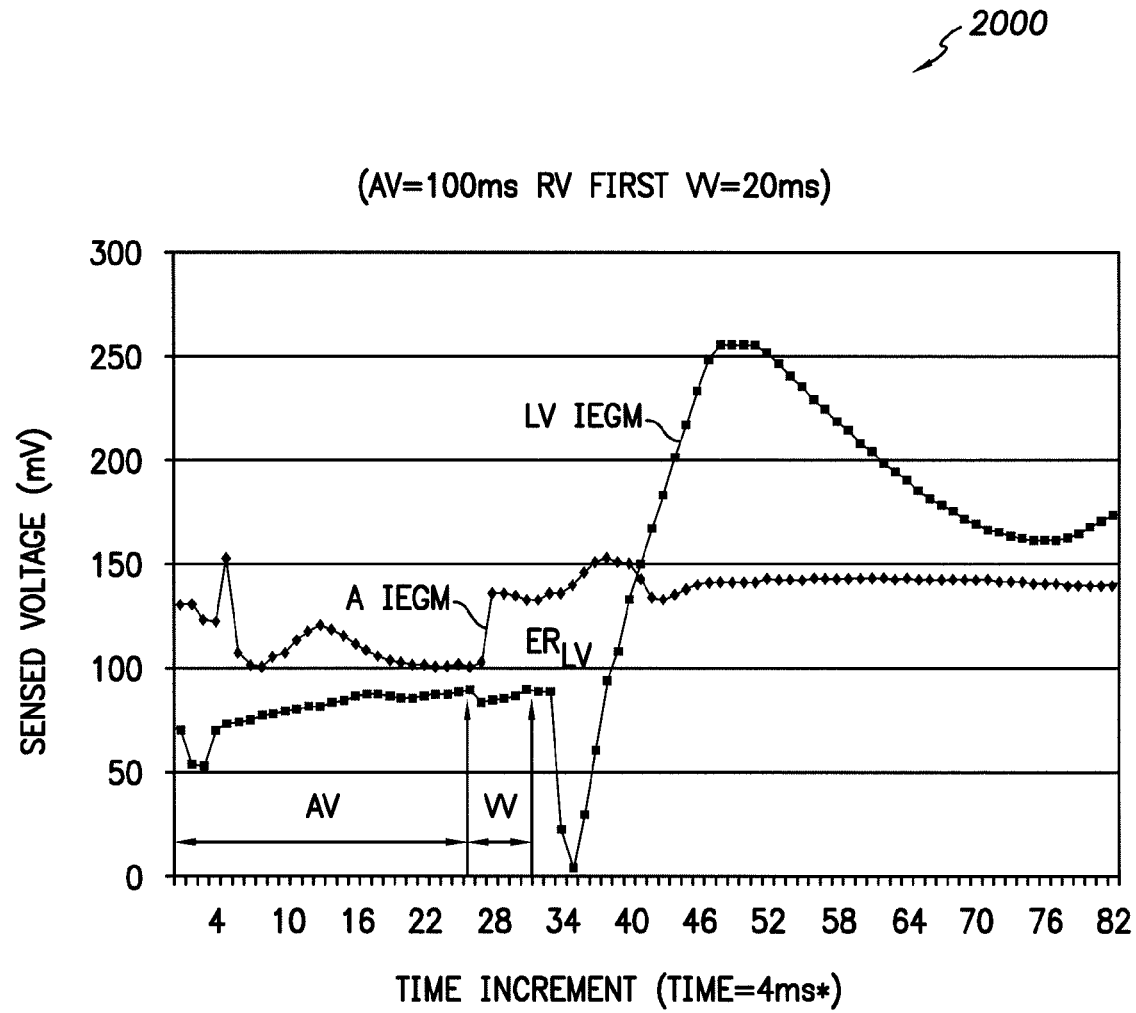
FIG. 20 is an exemplary plot of sensed voltage versus time for right ventricular stimulation and left ventricular stimulation (i.e., biventricular stimulation).

FIG. 20 shows an exemplary plot 2000 of sensed cardiac activity versus time for a short $AV_{RV}$ delay and a VV delay of about 20 ms. The sensed cardiac activity includes activity sensed in the atrium and activity sensed in the left ventricle. In this example, biventricular pacing occurs where right ventricular stimulation occurs prior to left ventricular stimulation. Further, an evoked response occurs in the left ventricle ($ER_{LV}$) prior to propagation of a wavefront from the right ventricle. Consequently, the left ventricular stimulation causes the left ventricle to contract. The left ventricular IEGM (LV IEGM) exhibits a relatively large deviation in voltage over a time period of about 160 ms where the downward deviation from baseline occurs in about the first 20 ms and a return to baseline in about the next 20 ms.

Figure 21:
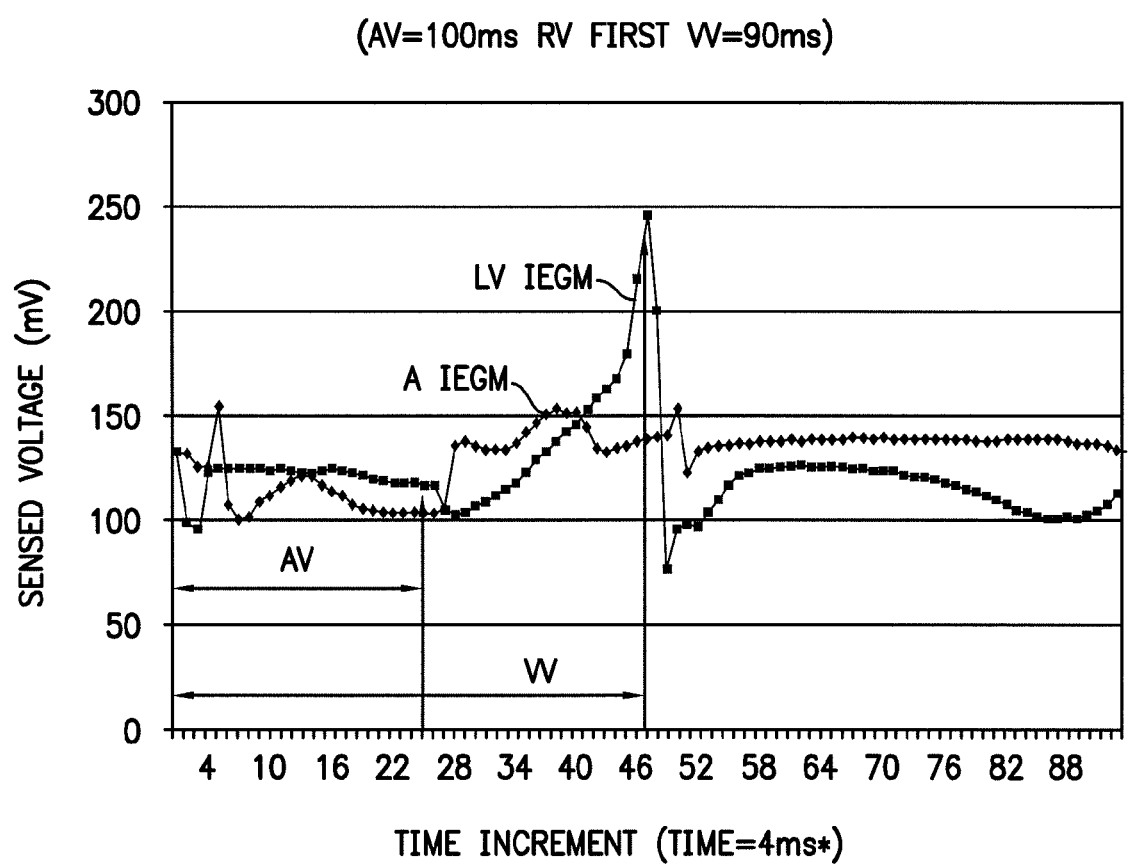
FIG. 21 is an exemplary plot of sensed voltage versus time for right ventricular stimulation and left ventricular stimulation (i.e., biventricular stimulation) where fusion has occurred in the left ventricle.

FIG. 21 shows an exemplary plot 2100 of sensed cardiac activity versus time for a short $AV_{RV}$ delay and a VV delay of about 90 ms. The sensed cardiac activity includes activity sensed in the atrium (A IEGM) and activity sensed in the left ventricle (LV IEGM). In this example, biventricular pacing occurs where right ventricular stimulation occurs prior to left ventricular stimulation (i.e., $AV_{RV} < AV_{LV}$ and $AV_{LV} = AV_{RV} + VV$). However, in contrast to the plot 2000 of FIG. 20, fusion occurs in the left ventricle as the paced stimulus to the right ventricle conducts to the left ventricle and fuses with the paced stimulus to the left ventricle (see, e.g., Scenario 5 of Table 1). In this instance, detection of local fusion in the left ventricle VVF-RL can serve as a surrogate for PIVCD-RL, for example, as described above. If the left ventricle was paced first, then detection of local fusion in the right ventricle VVF-LR can serve as a surrogate for PIVCD-LR. Again, VVF-RL and VVF-LR typically rely on use of AV or PV timing that avoids competition with atrial to ventricular conduction. Noting that the AV timing for the earlier paced ventricle may be adjusted to determine an AVF for the earlier paced ventricle. Thus, surrogates to AR or PR and PIVCD may be determined.

A comparison of the plot 2000 and the plot 2100 demonstrates differences between an evoked response and fusion. In the exemplary plot 2100 the downward deviation in sensed voltage and minimum sensed voltage for the left ventricle is much less than that of the plot 2000 where an evoked response occurred. Various exemplary methods, devices, systems, etc., may rely on IEGM amplitude, slope, area, morphology, etc., to determine whether fusion has occurred.

Sensing through use of an atrial channel may have some advantages. For example, such sensing may allow for atrial capture detection, atrial blanking, far-field R wave sensing, bipolar or unipolar electrode configurations, use of unipolar electrode configuration for far-field sensing. While the various exemplary plots show some drift in atrial channel voltage, blanking may be short and help to balance a baseline.

Figure 22:
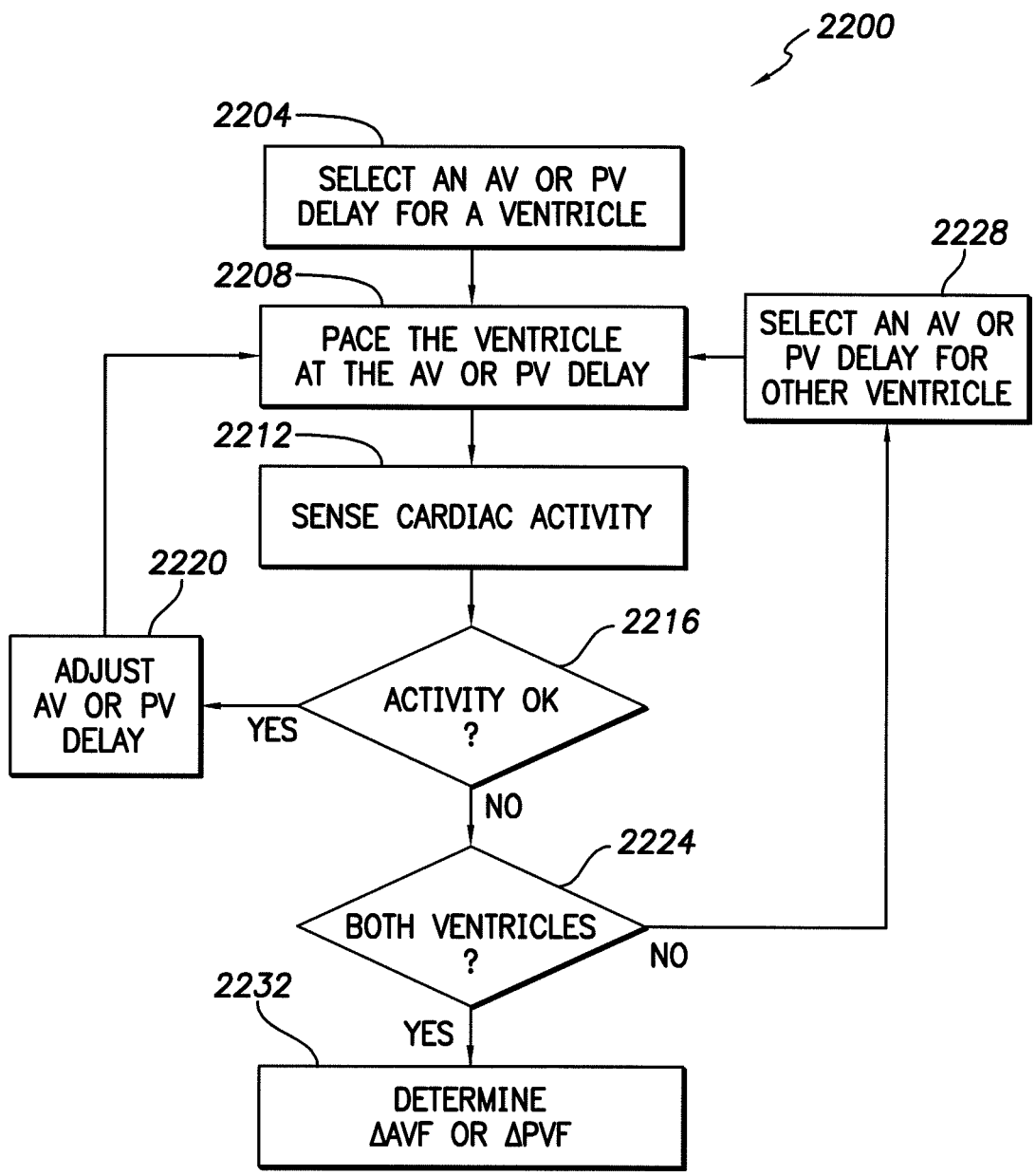
FIG. 22 is a block diagram of an exemplary method that relies on diminished amplitude and/or other morphology to determine one or more ventricular pacing parameters.

FIG. 22 shows an exemplary method 2200 for determining an atrio-ventricular fusion time for a ventricle, which is referred to as $AVF_{RV}$ or $AVF_{LV}$ or $PVF_{RV}$ or $PVF_{LV}$ depending on the ventricle paced and whether an atrial stimulus is used. The exemplary method 2200 optionally finds times for both ventricles as well. The atrio-ventricular fusion time can serve as a surrogate or substitute for a ventricular AR or PR time, as appropriate. Where atrio-ventricular fusion times are measured for both ventricles, then another value may be determined, referred to as $\Delta AVF$ ($AVF_{LV} - AVF_{RV}$) or $\Delta PVF$ ($PVF_{LV} - PVF_{RV}$), depending on whether an atrial stimulus is used, and this value may serve as a substitute for $\Delta$, where $\Delta = AR_{LV} - AR_{RV}$ or $PR_{LV} - PR_{RV}$. Of course, in some instances, a hybrid $\Delta$ (e.g., $\Delta A$-PVF) may be used where one time corresponds to an atrial stimulus and another corresponds to an intrinsic atrial event.

With respect to the exemplary method 1600 of FIG. 16, an AVF or PVF time may be used to determine a master-slave relationship for the ventricles (see, e.g., the decision block 1608). Of course, two AVF or PVF times may be compared or an AVF time and a PVF time or an AR or PR time and an AVF or PVF time. In general, the ventricle with larger time is the master ventricle and the one with smaller time is the slave ventricle. As already mentioned, one or more AVF or PVF times may be used to determine a Δ (see, e.g., the determination block 1620).

According to the exemplary method 2200, the method commences in a selection block 2204 where an AV or a PV delay is selected for a particular ventricle. The selected delay is optionally a short delay that may be incremented or a long delay that may be decremented. Of course, other selections and/or adjustments are possible. A pacing block 2208 paces the ventricle at the selected AV or PV delay. Cardiac activity responsive to the ventricular stimulus delivered according to the selected AV or PV delay is sensed in a sensing block 2212. A decision block 2216 follows that decides if the sensed cardiac activity is representative of an unaffected evoked response (i.e., Activity OK?). For example, the decision block 2216 may compare one or more characteristics of the cardiac activity to a limit or limits.

In the example of FIG. 20, the LV IEGM exhibits an unaffected evoked response that has a downward deviation from an approximate baseline value while in the example of FIG. 21, fusion occurs and the LV IEGM does not exhibit such a downward deviation. To distinguish between these two cases, a limit may be set as a voltage or as a voltage difference (e.g., a difference between a baseline and a minimum value for an evoked response). More specifically, referring to the LV IEGM of FIG. 21, a voltage of about 50 mV could serve as a limit, alternatively, or in addition to, a voltage difference could serve as a limit. Of course, if the polarity of the IEGM sensing was reversed, then the limit or limits would be adjusted accordingly. For example, a maximum in amplitude or a positive deviation from an approximate baseline amplitude (i.e., an amplitude difference) would be compared to a limit or limits. Further, an exemplary method could use both an amplitude and an amplitude difference. Yet further, various exemplary methods could use other techniques as adjuncts or alternatives (e.g., morphology, a derivative, an integral, etc.).

Referring again to the exemplary method 2200 of FIG. 22, if the decision block 2216 decides that the sensed cardiac activity is representative of an evoked response occurred (i.e., a "normal" evoked response), then an adjustment block 2220 adjusts the AV or PV delay and the method 2200 continues at the pacing block 2208. However, if the decision block 2216 decides that the activity is not representative of an evoked response, then it is likely that the ventricular stimulus fused or otherwise interfered with a conducted atrial stimulus, in other words, a fusion beat occurred in the ventricle (see, e.g., the plot 2100). In this instance, the method 2200 sets AVF to the AV or PVF to PV for the ventricle and continues in another decision block 2224 that decides whether information has been acquired for both ventricles (e.g., an $AVF_{RV}$ and an $AVF_{LV}$, etc.). A time limit or other limit(s) may be used to help ensure that the information for both ventricles is comparable. An exemplary method may optionally alternate between ventricles, for example, applying an $AV_{RV}$ and then an $AV_{LV}$, adjusting as required.

If information has been acquired for only one ventricle, then the method 2200 continues at the selection block 2228, which selects the other ventricle. However, if suitable information has been acquired for both ventricles, then the method 2200 continues in a determination block 2232 that determines ΔAVF or ΔPVF, as appropriate. This value may be used as a substitute for the parameter Δ, as described elsewhere herein.

In some instances a correction term may be used to account for a time difference between local fusion and an R wave peak (or valley). Where such a time difference exists, and is similar for both ventricles, then no correction term is needed for ΔAVF or ΔPVF since the subtraction will act to cancel the time differences. While various exemplary methods, devices, systems, etc., apply to the ventricles, the same approach may be applied to the atria to determine inter-atrial conduction delay.

An exemplary method may include delivering repeatedly a stimulus to a ventricle, at a plurality of atrio-ventricular delays, until fusion occurs in the ventricle and determining one or more biventricular pacing parameters based at least in part on the atrio-ventricular delay that caused fusion. Such a method may perform actions such as those described with respect to the exemplary method 2200 of FIG. 22.

Various exemplary methods include delivering repeatedly a stimulus to a ventricle, at a plurality of ventricular activation times, until fusion occurs in the ventricle and determining an atrio-ventricular conduction time for the ventricle based at least in part on the ventricular activation time that caused fusion. A ventricular activation time may be based on an atrio-ventricular delay. A ventricular activation time may be referenced with respect to an event that occurs during a cardiac cycle, whether intrinsic or non-intrinsic, for example, a P wave, an A wave, a prior ventricular activation, etc. In such exemplary methods, the fusion may occur between the stimulus and an intrinsic atrial stimulus conducted to the ventricle via the atrio-ventricular node or between the stimulus and a non-intrinsic atrial stimulus conducted to the ventricle via the atrio-ventricular node.

While the exemplary method 2200 refers to atrio-ventricular fusion delay (AVF) to determine ΔAVF, one or more ventricular activation times may be used to determine ΔAVF. For example, subtracting a ventricular activation time that causes fusion for one ventricle from a ventricular activation time that causes fusion for the other ventricle can yield ΔAVF or ΔPVF, as appropriate.

Various exemplary methods are optionally implemented through use of one or more computer-readable media. For example, a method may be implemented, at least in part, through use of instructions that can instruct a microprocessor or microcontroller (see, e.g., the microcontroller 220 of FIG. 2). An exemplary implantable pacing apparatus may include a power source, a connector for a lead bearing one or more electrodes, a sensing circuit and control logic. For example, exemplary control logic instruct such an apparatus to select a ventricular activation time, to delivery energy from the power source to the connector based at least in part on the selected ventricular activation time, to sense cardiac activity, to decide if fusion occurred based at least in part on the sensed cardiac activity, and, if fusion occurred, adjusting one or more biventricular pacing parameters based at least in part on the ventricular activation time that caused fusion.

Figure 23:
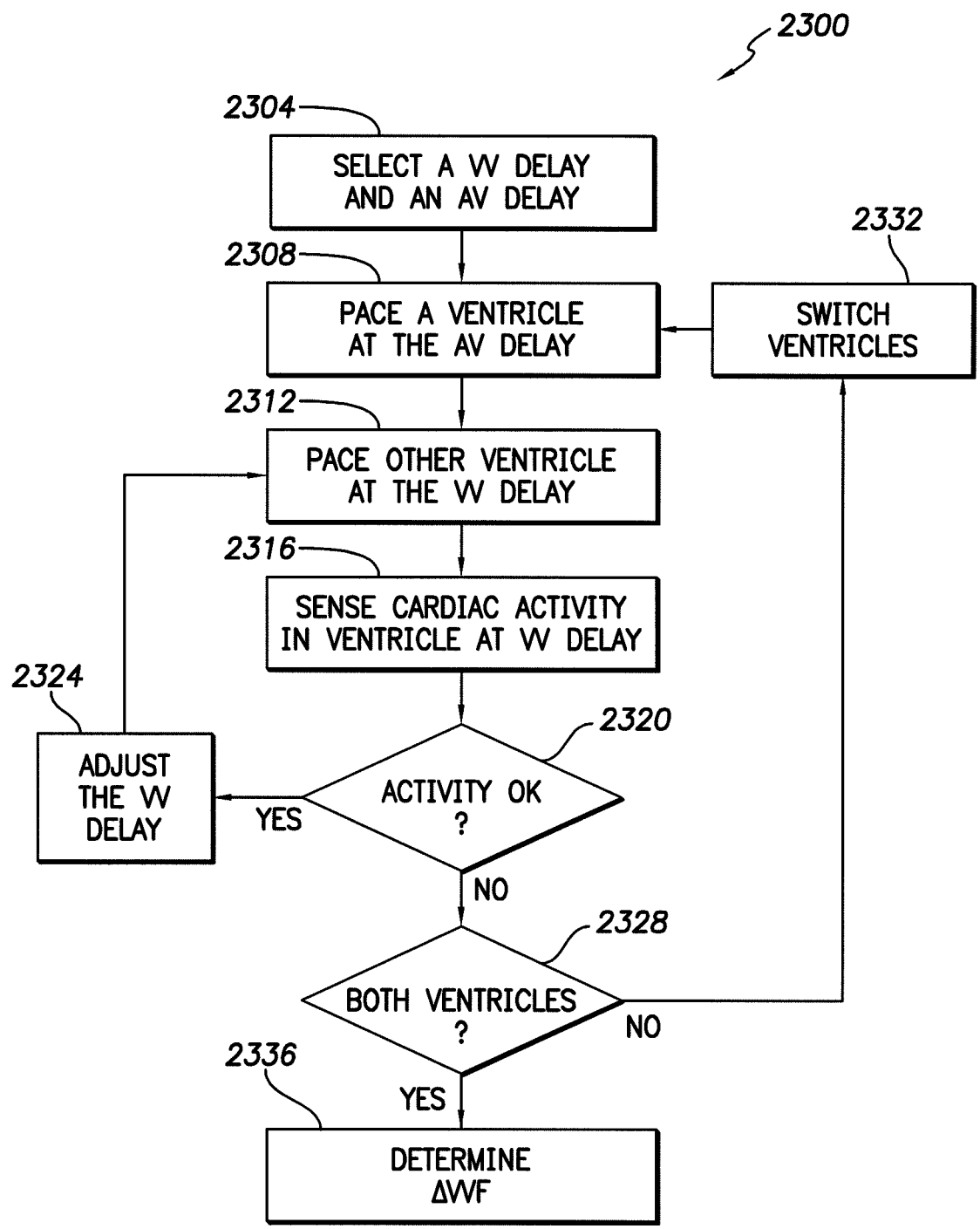
FIG. 23 is a block diagram of an exemplary method that relies on biventricular stimulation and diminished amplitude and/or other morphology to determine one or more ventricular pacing parameters.

FIG. 23 shows an exemplary method 2300 for determining an interventricular fusion time for a ventricle, which is referred to as VVF-RL or VVF-LR depending on which ventricle is paced first. The interventricular fusion time can serve as a surrogate or substitute for an interventricular time PIVCD-RL or PIVCD-LR, as appropriate. Where interventricular fusion times are measured in both directions (i.e., left to right and right to left), then another value may be determined, referred to as ΔVVF (ΔVVF=VVF-LR−VVF-RL), and this value may serve as a substitute for $\Delta_{PIVCD}$, where $\Delta_{PIVCD}$=PIVCD-LR−PIVCD-RL (see, e.g., the exemplary method 1700 of FIG. 17).

The exemplary method 2300 commences in a selection block 2304 where a VV delay and an AV delay are selected. In general, the AV delay is set short to avoid competition with conduction of the atrial stimulus to one or both of the ventricles. While AV delay is mentioned, PV delay may also be used. A pacing block 2308 follows where one of the ventricles is paced according to the selected AV delay. Another pacing block 2312 then occurs where the other ventricle is paced according to the selected VV delay. A sensing block 2316 senses cardiac activity that would indicate whether any interference occurred between the latter delivered ventricular stimulus and the prior delivered ventricular stimulus as it may have conducted to the latter delivered ventricle. Again, the AV delay and VV delay are typically set to avoid ventricular depolarization from an atrial stimulus conducted to one or both of the ventricles. In some examples, a discrimination algorithm may be able to determine if an atrial stimulus (intrinsic or non-intrinsic) conducted to the latter paced ventricle caused interference as opposed to, or in addition to, a conducted wavefront from the earlier paced ventricle. Further, as mentioned with respect to the Scenarios 5 and 6 of Table 1, the selected AV delay of the selection block 2304 may be adjusted to determine an AVF time for the earlier paced ventricle.

After sensing, a decision block 2320 decides if the sensed cardiac activity is representative of an unaffected evoked response (i.e., Activity OK?). For example, the decision block 2320 may compare one or more characteristics of the cardiac activity to a limit or limits as discussed with respect to the exemplary method 2200. In the exemplary method 2300, if the decision block 2320 decides that the sensed cardiac activity is representative of an evoked response occurred then an adjustment block 2324 adjusts the VV delay. With respect to VV delay, while a VV delay of 80 ms may be tolerable in humans for therapy, for such an exemplary method, the VV delay could be longer. After the adjustment block 2324, the method 2300 continues at the pacing block 2312. However, if the decision block 2320 decides that the activity is not representative of an evoked response, then it is likely that the ventricular stimulus fused or otherwise interfered with a conducted atrial stimulus, in other words, a fusion beat occurred in the ventricle (see, e.g., the plot 2100). In this instance, the method 2300 sets VV to VVF-RL or VVF-LR for the ventricle and continues in another decision block 2328 that decides whether information has been acquired for both directions, i.e., left to right and right to left. A time limit or other limit(s) may be used to help ensure that the information for both directions is comparable. An exemplary method may optionally alternate between directions, i.e., right to left and then left to right, in determining VVF-RL and VVF-LR.

If the decision block 2328 decides that information has been acquired for only one direction, then the method 2300 continues at a switch block 2332, which switches the direction. However, if suitable information has been acquired for both directions, then the method 2300 continues in a determination block 2336 that determines the parameter $\Delta VVF$. This value may be used as a substitute for the parameter $\Delta_{PIVCD}$, as described elsewhere herein.

While various exemplary methods, devices, systems, etc., apply to the ventricles, the same approach may be applied to the atria to determine inter-atrial conduction delay.

In the foregoing, various techniques have been set forth for estimating optimal AV/PV pacing delays for use by a pacemaker or ICD, hereinafter generally referred to as a pacer/ICD, and for then controlling the delivery of pacing therapy. To briefly summarize some of the foregoing techniques, optimal AV/PV pacing delays are estimated by first determining or inputting a paced interventricular conduction delay ($\Delta_{PIVCD}$) and an intrinsic interventricular conduction delay ($\Delta$). AR/PR conduction delays are measured within the patient, then the optimal AV/PV pacing delays are determined or estimated based on the measured conduction delays along with $\Delta_{PIVCD}$ and $\Delta$ and, typically, a predetermined interventricular correction term ($\epsilon$). Preferably, optimal AV/PV pacing delays are determined for both the LV and the RV. (See, e.g., FIGS. 10-12.)

Note that, in some examples set forth above, the calculation of the optimal AV/PV pacing delays for the LV and the RV exploit pre-determined values referred to $AV_{OPTIMAL}$ and $PV_{OPTIMAL}$. See, e.g., Eqns. 2 and 3, above. These values may initially be determined for the patient using otherwise conventional AV/PV optimization techniques (such as by using a programmer-based optimization procedure) or may be initially set by a clinician or may be set to suitable default values. The initial or default values for $AV_{OPTIMAL}$ and $PV_{OPTIMAL}$ may then be updated as described above in Eqn. 12. These predetermined values should not be confused with the optimal AV/PV delays values discussed in the following sections, which are determined as part of the optimization procedure for use in the delivery of actual pacing therapy. Also, it should be understood that any of the various optimized or optimal values discussed herein are estimates of optimal values, which are expected to provide effective therapy but which are not necessarily absolutely optimal. These values are also referred to herein as "preferred" values.

Figure 30:
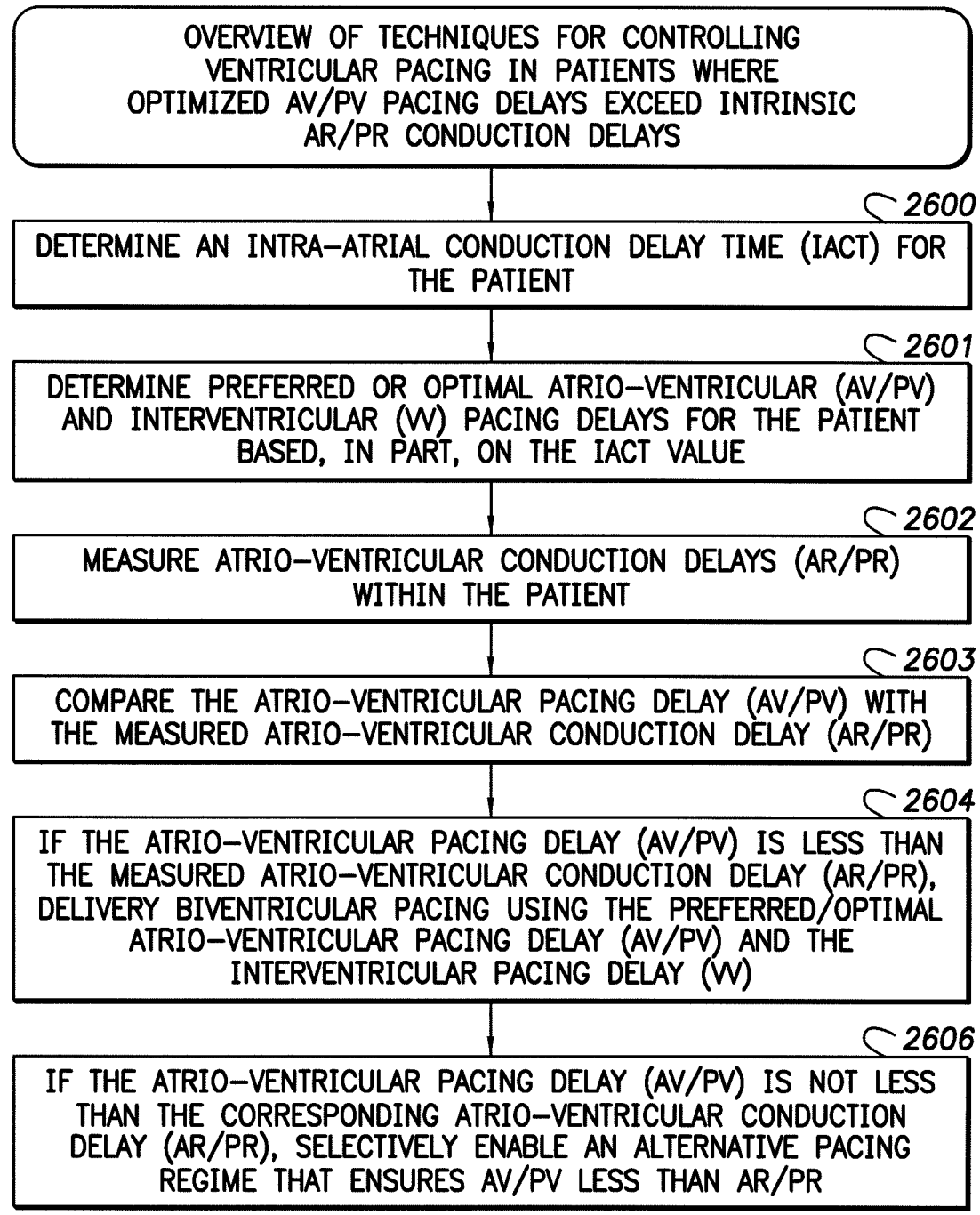
FIG. 30 is a flow chart summarizing an exemplary method for controlling ventricular pacing in patients where optimized AV/PV pacing delays exceed intrinsic AR/PR conduction delays due to long inter-atrial conduction delays.
Figure 31:
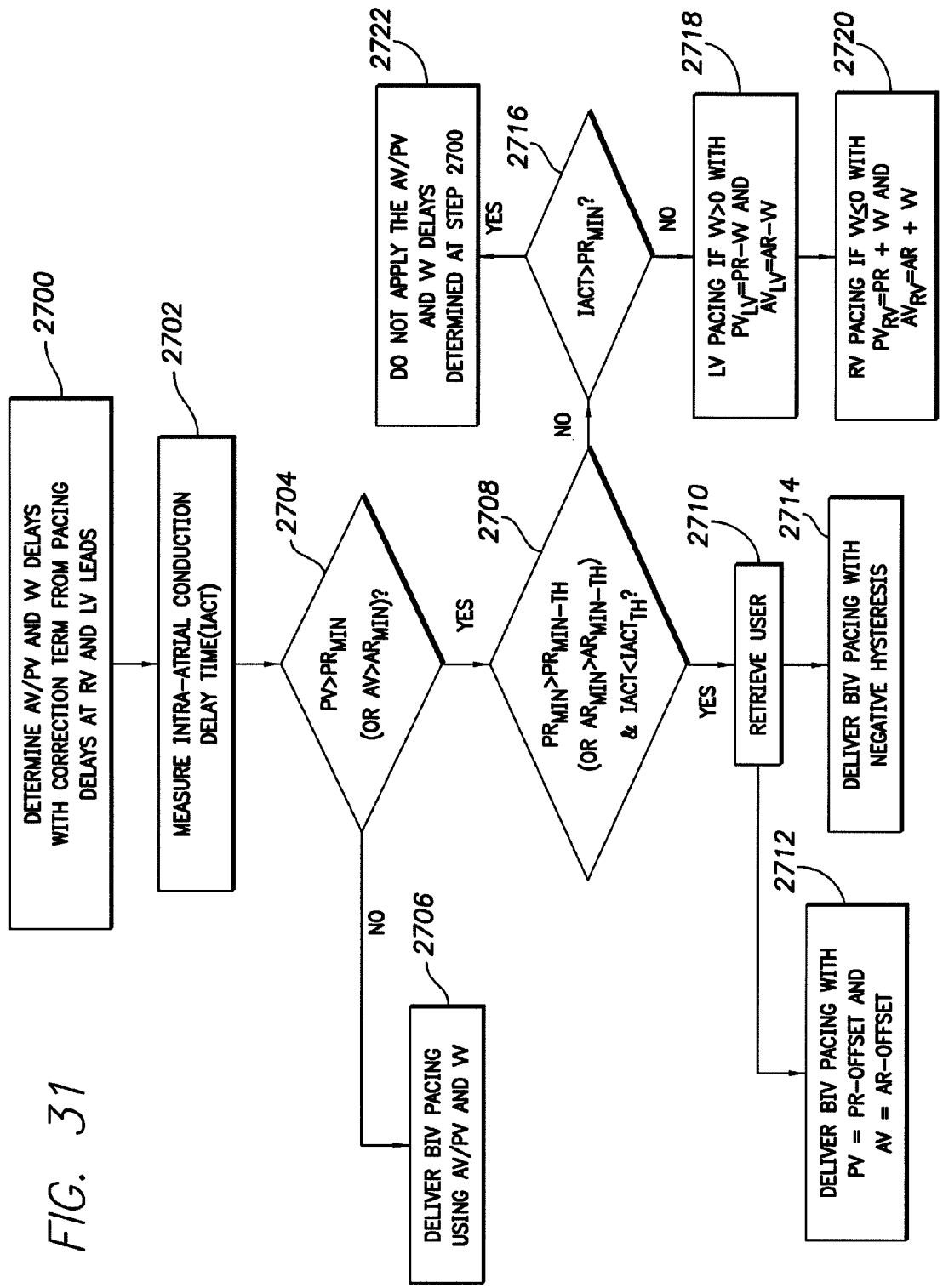
FIG. 31 is a flow chart illustrating an exemplary implementation of the technique of FIG. 30, which distinguishes among various pacing regimes if the optimized AV/PV pacing delays exceed the intrinsic AR/PR conduction delays.
Figure 32:
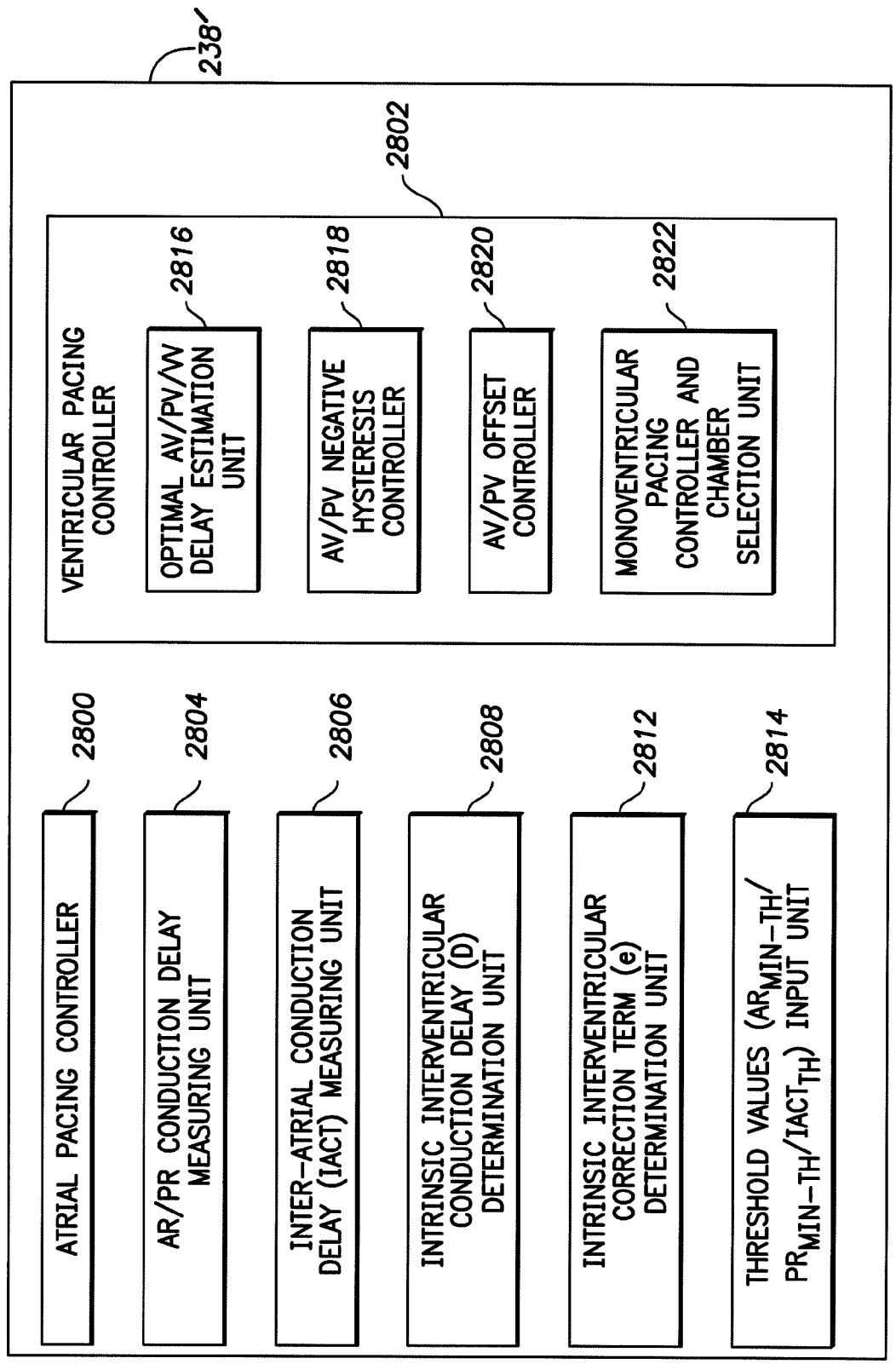
FIG. 32 is a block diagram illustrating pertinent components of the AA/AV/VV module of FIG. 2 for use in implementing the techniques of FIGS. 24-31.

With reference to the remaining figures, techniques are described that modify, expand or supersede the above-described procedures. In particular, FIGS. 24-25 set forth alternative procedures for estimating optimal AV/PV delays, which exploit measured inter-atrial conduction delays rather than measured atrio-ventricular conduction delays. FIGS. 26-29 set forth alternative procedures for estimating optimal AV/PV pacing delays and VV pacing delays, which exploit both inter-atrial conduction delays and interventricular conduction delays. The alternative procedures of FIGS. 24-29 are preferred over those of FIGS. 1-23. FIGS. 30-32 set forth techniques that address circumstances where the calculated AV/PV pacing delays exceed measured AR/PR conduction delays. These techniques are particularly helpful for use in patients with long inter-atrial conduction delays, but the techniques may be exploited in other patients as well.

Optimization Techniques Exploiting Measured Inter-Atrial (AE/PE) Delays

Figure 24:
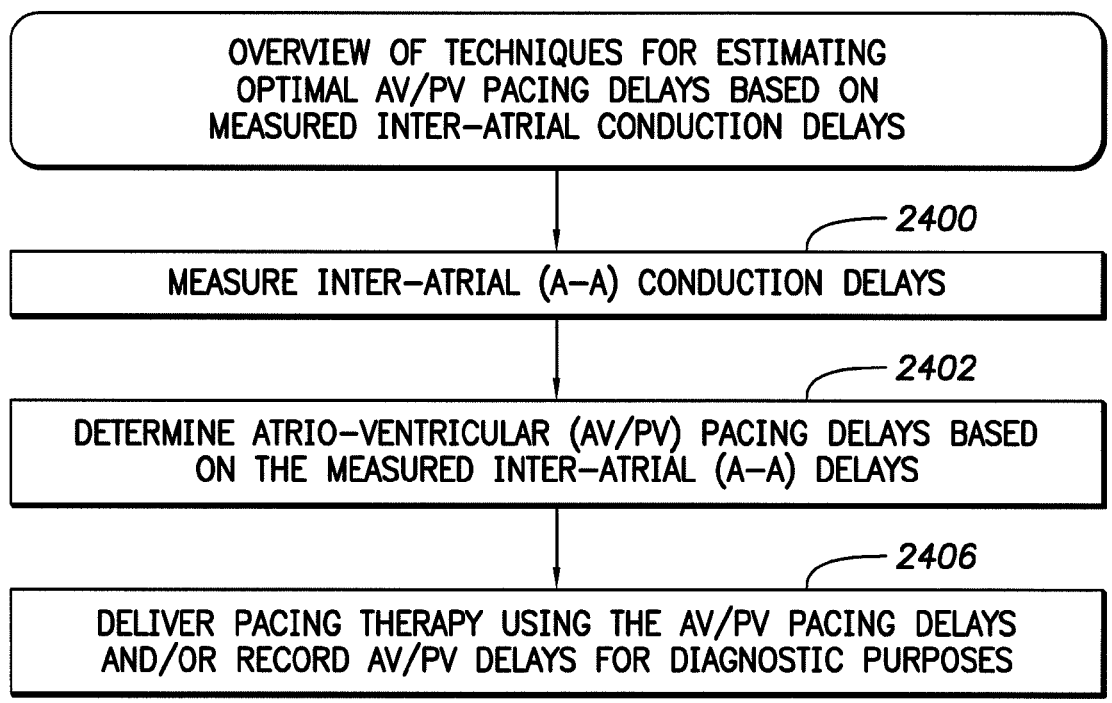
FIG. 24 is a flow chart summarizing an exemplary method for estimating optimal AV/PV pacing delays using inter-atrial delays (AE/PE).

FIG. 24 provides an overview of techniques that exploit inter-atrial delays for determining AV/PV pacing delays. Beginning at step 2400, the pacer/ICD measured inter-atrial conduction (A-A) delays (also referred to herein as IACT delays) with the patient and, at step 2402, determines AV/PV pacing delays based on the measured inter-atrial (A-A) conduction delays. Pacing therapy is delivered to the patient at step 2406 using the AV/PV pacing delays. Alternatively, the AV/PV pacing delays are recorded for diagnostic purposes. The inter-atrial conduction delays may be estimated based on the duration of atrial events, i.e. the duration of P-waves or atrial evoked responses. The duration of the P-wave is referred to herein as PE. The duration of the atrial evoked response is referred to herein as AE. Additional information regarding the determination and exploitation of inter-atrial conduction delays is set forth in U.S. Pat. No. 7,248,925, cited above. Herein, inter-atrial delays refer to delays measured between two points on or within one or both of the atria. In the exemplary embodiments described herein, one point is on or within the left atrium and the other is on or within the right atrium; however, other embodiments may involve measurements taken between two points on or within one atrial chamber. Accordingly, these inter-atrial delays may alternatively be referred to as intra-atrial delays.

Figure 25:
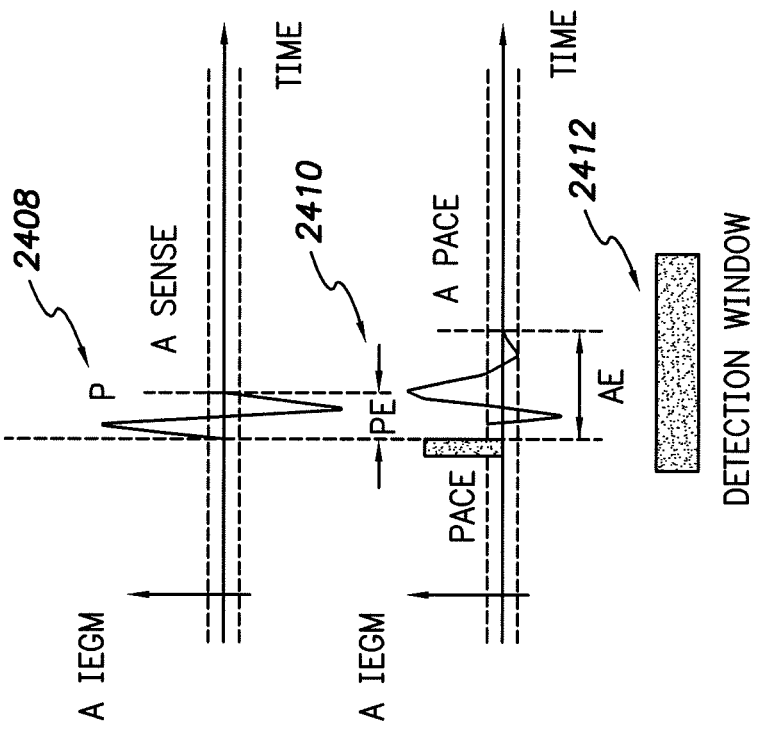
FIG. 25 is an exemplary graph summarizing AV/PV delay estimation of FIG. 24, including exemplary formulas.

FIG. 25 illustrates an example showing a P-wave 2408 and its duration PE and an atrial evoked response and its duration AE. A detection window 2412 may be used to detect P-waves and/or atrial evoked responses, as shown. The detection window ends at the ventricular event (either V sensed or V paced event). FIG. 25 also provides formula for determining PV based on PE, and for determining AV based on AE, as follows:

$$AV=AE+\delta; \text{if } AE<150 \text{ ms}, \delta=60 \text{ ms}; \text{if } AE \geq 150 \text{ ms}, \delta=30 \text{ ms}.$$

$$PV=PE+\delta; \text{if } PE<100 \text{ ms}, \delta=60 \text{ ms}; \text{if } PE \geq 100 \text{ ms}, \delta=30 \text{ ms}.$$

More generally, for AV delays, $\delta$ is set to a first programmable or hard-coded offset value ($T_1$) if AE is at least equal to a programmable threshold ($W_{AE}$) and is instead set to a second programmable value ($T_2$) if AE is less than $W_{AE}$. In the example shown, $T_1$ is 30 milliseconds (ms), $T_2$ is 60 ms, and $W_{AE}$ is 150 ms. Although these values are typically preferred, other suitable values for $T_1$, $T_2$, and $W_{AE}$ may potentially be used as determined, e.g., via otherwise routine experimentation. Likewise, for PV delays, $\delta$ is set to a first programmable value ($T_1$) if PE is at least equal to $W_{PE}$ and is instead set to a second programmable value $T_2$ if PE is less than $W_{PE}$. In the example shown, $T_1$ is again 30 ms and $T_2$ is 60 ms. $W_{PE}$ is 100 ms. Although these values are typically preferred, other suitable values for $T_1$, $T_2$, and $W_{PE}$ may potentially be used as determined, e.g., via otherwise routine experimentation. Also, the $T_1$ and $T_2$ use for calculating AV may differ from those used for calculating PV.

The techniques of FIGS. 24-25 are appropriate for use in generating AV/PV pacing delays for use in single-chambered (i.e. monoventricular) pacing. Alternatively, the techniques may be used to estimate AV/PV pacing delays for diagnostic purposes. In either case, the techniques are simple but effective.

Figure 26:
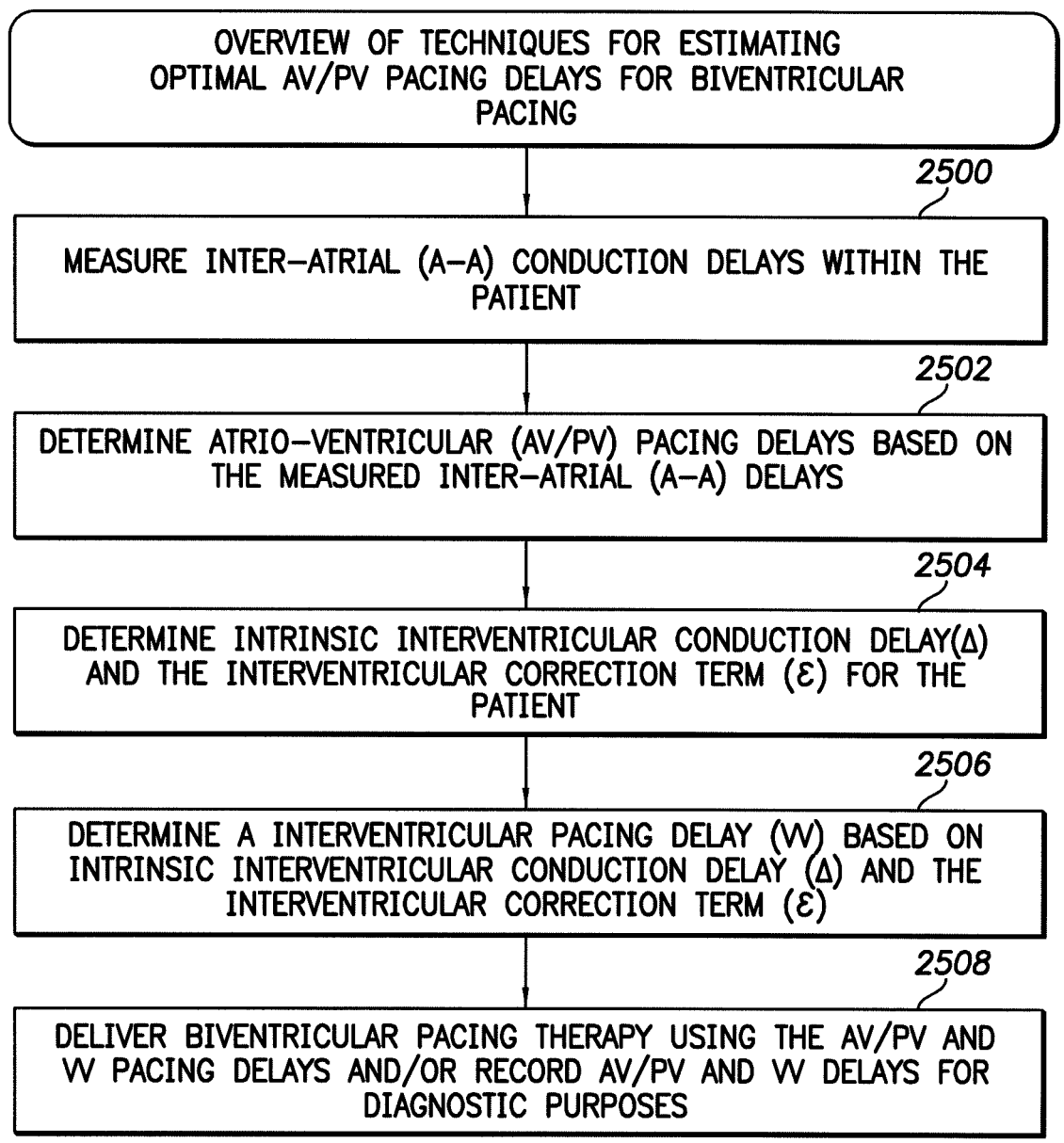
FIG. 26 is a flow chart summarizing an exemplary method for estimating optimal AV/PV/VV pacing delays using inter-atrial delays (AE/PE) and various interventricular values including $\Delta$ and $\epsilon$.

FIG. 26 provides an overview of techniques that exploit inter-atrial delays and various interventricular for determining AV/PV delays, as well as VV delays. Beginning at step 2500, the pacer/ICD measures inter-atrial conduction (A-A) delays with the patient and, at step 2502, determines AV/PV pacing delays based on the measured inter-atrial (A-A) conduction delays, as in FIG. 25. At step 2504, the pacer/ICD then determines the intrinsic interventricular conduction delay ($\Delta$) and the interventricular correction term ($\epsilon$) within the patient and, at step 2506, the pacer/ICD determines an interventricular pacing delay (VV) based on $\Delta$ and $\epsilon$. Exemplary techniques for determining $\Delta$ and $\epsilon$, and for then calculating VV based on $\Delta$ and $\epsilon$ are discussed below. Depending upon the implementation, this may be performed to yield separate atrio-ventricular pacing delays for the LV and the RV. Pacing therapy is delivered to the patient at step 2508 using the AV/PV and VV pacing delays pacing delays. Alternatively, the AV/PV and VV pacing delays are recorded for diagnostic purposes. Also note that the various tests or procedures to determine AV/PV and VV pacing delays can be independent of one another.

Figure 27:
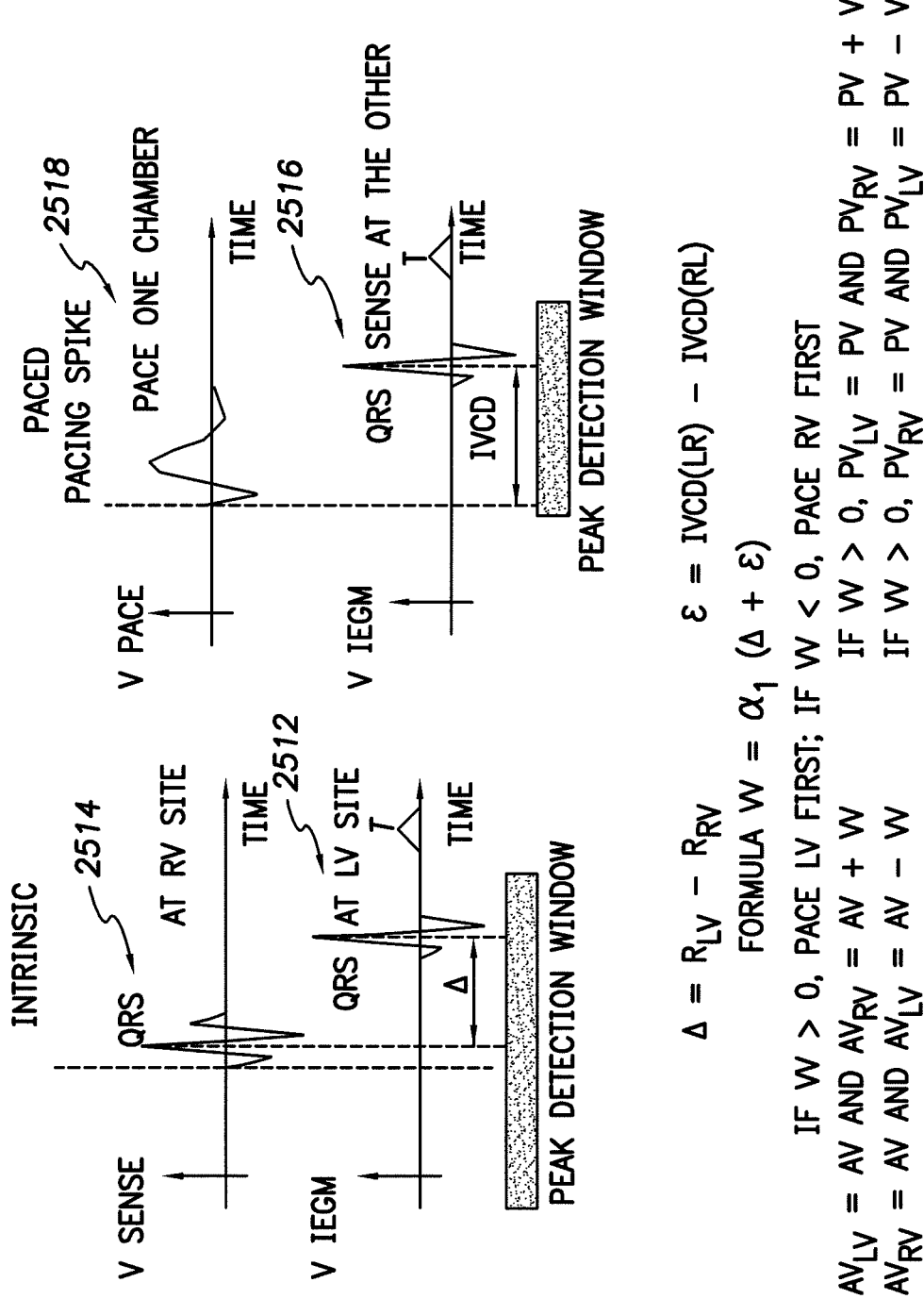
FIG. 27 is an exemplary graph summarizing a first implementation of the AV/PV/VV delay estimation technique of FIG. 26, including exemplary formulas exploiting $\Delta$ and $\epsilon$.

FIG. 27 illustrates an example showing an LV QRS-complex 2512 and an RV QRS-complex 2514 and indicating the intrinsic interventricular conduction delay ($\Delta$) therebetween (measured from peak to peak). As such, $\Delta = R_{LV} - R_{RV}$. FIG. 27 also illustrates a QRS-complex 2516 in one ventricular chamber and a preceding evoked response 2518 in the other ventricular chamber (triggered by a V-pulse) and further indicating the interventricular conduction delay (IVCD) therebetween. The interventricular correction term ($\epsilon$) is calculated by determining an IVCD value for conduction from the LV to the RV (i.e. IVCD(LR)) and an IVCD value for conduction from the RV to the LV (i.e. IVCD(RL)), then subtracting one from the other. That is, $\epsilon = \text{IVCD(LR)} - \text{IVCD(RL)}$. This may be achieved by first pacing the LV and determining the IVCD to the RV, then pacing the RV and determining the IVCD to the LV.

As shown in FIG. 27, VV is then calculated using:

$$VV=\alpha_1(\Delta+\epsilon)$$

where $\alpha_1$ is a programmable or hard-coded parameter that may vary from patient to patient. In some examples, $\alpha_1$ is set to 0.5, which may also be used as a default value.

Then, if VV>0, the LV is paced first; otherwise the RV is paced first. That is, for an AV example:

If $VV>0, AV_{LV}=AV$ and $AV_{RV}=AV+VV$.

If $VV<0, AV_{RV}=AV$ and $AV_{LV}=AV-VV$.

If $VV=0, AV_{RV}=AV_{LV}=AV$

For a PV example:

If $VV>0, PV_{LV}=PV$ and $PV_{RV}=PV+VV$.

If $VV<0, PV_{RV}=PV$ and $PV_{LV}=PV-VV$.

If $VV=0, PV_{RV}=PV_{LV}=PV$

Figure 28:
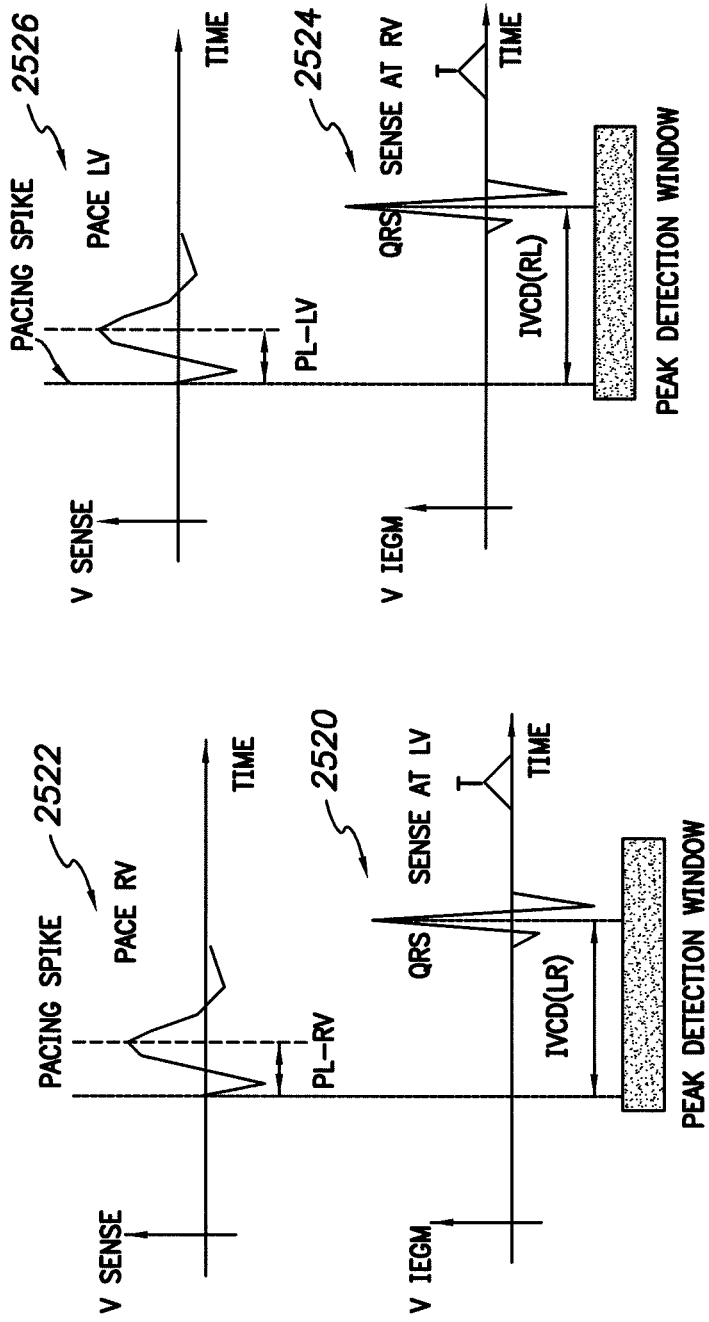
FIG. 28 is an exemplary graph summarizing a second implementation of the AV/PV/VV delay estimation technique of FIG. 26, including exemplary formulas exploiting $\Delta$ and $\epsilon$, as well as a correction factor $\theta$.

FIG. 28 illustrates another example wherein an additional correction term $\theta$ is used. The correction term ($\theta$) is determined based on $\Delta$ and $\epsilon$ as follows. VV is calculated based on $\Delta$ and $\epsilon$, as already described. Then, if VV>0, a time delay ($PL_{LV}$) is measured from pacing pulse until the peak of the resulting LV evoked response. A baseline value is then subtracted from $PL_{LV}$ to yield $\theta$. Conversely, if VV<0, a time delay ($PL_{RV}$) is measured from a V-pulse until the peak of the resulting RV evoked response. The baseline value is then subtracted from $PL_{RV}$ to yield $\theta$. In either case, the baseline value can be within a range of values such as 60 ms–80 ms and can be set to, e.g., 70 ms.

The figure illustrates the LV QRS-complex 2520 and the preceding evoked response 2522 in the RV (triggered by a V-pulse) and further indicates the interventricular conduction delay IVCD(LR) from LV to RV. Also shown is a $PL_{RV}$ value, which represents the time delay from the V-pulse to the peak of the evoked response in the RV. The figure additionally shows an RV QRS-complex 2524 and a preceding evoked response 2526 in the LV (triggered by a V-pulse) and further indicating the interventricular conduction delay IVCD(RL) from RV to LV. Also shown is a $PL_{LV}$ value, which represents the time delay from the V-pulse to the peak of the evoked response in the LV.

Once $\theta$ has been determined, AV and PV delays are calculated as follows:

$$AV=AE+\delta-\theta; \text{if } AE<150 \text{ ms}, \delta=60 \text{ ms}; \text{if } AE \geq 150 \text{ ms}, \delta=30 \text{ ms}.$$

$$PV=PE+\delta-\theta; \text{if } PE<100 \text{ ms}, \delta=60 \text{ ms}; \text{if } PE \geq 100 \text{ ms}, \delta=30 \text{ ms}.$$

The various values used therein (30 ms, 100 ms, etc.) are merely exemplary and different values may potentially be used (as determined using suitable experimental techniques.) Again, $\delta$ may be a programmable or hard-coded offset value.

As with the example of FIG. 27, if VV>0, the LV is paced first; otherwise the RV is paced first. That is, for an AV example:

If $VV>0, AV_{LV}=AV$ and $AV_{RV}=AV+VV$.

If $VV<0, AV_{RV}=AV$ and $AV_{LV}=AV-VV$.

If $VV=0, AV_{RV}=AV_{LV}=AV$

For a PV example:

If $VV>0, PV_{LV}=PV$ and $PV_{RV}=PV+VV$.

If $VV<0, PV_{RV}=PV$ and $PV_{LV}=PV-VV$.

If $VV=0, PV_{RV}=PV_{LV}=PV$.

Depending upon the capabilities of the pacer/ICD, the various quick optimization techniques thus far described can be implemented using differing numbers of sensing channels. Some devices, for example, provide only two sensing channels, whereas others provide three or more. With a two-channel implementation, quick optimization is typically performed by initially setting at least one channel to sense an atrial IEGM. The atrial channel signals are used to determine the AV/PV delays (as in FIGS. 24 and 25.) The, the pacer/ICD is reset so that the two channels sense RV and LV IEGM signals, respectively, which are used to determine the VV delay (as in FIGS. 26-28.) Three-channel systems instead allow the atrial channel IEGM and both LV and RV IEGMs to be sensed at the same time, permitting both the AV/PV and VV delays to be determined more readily.

Figure 29:
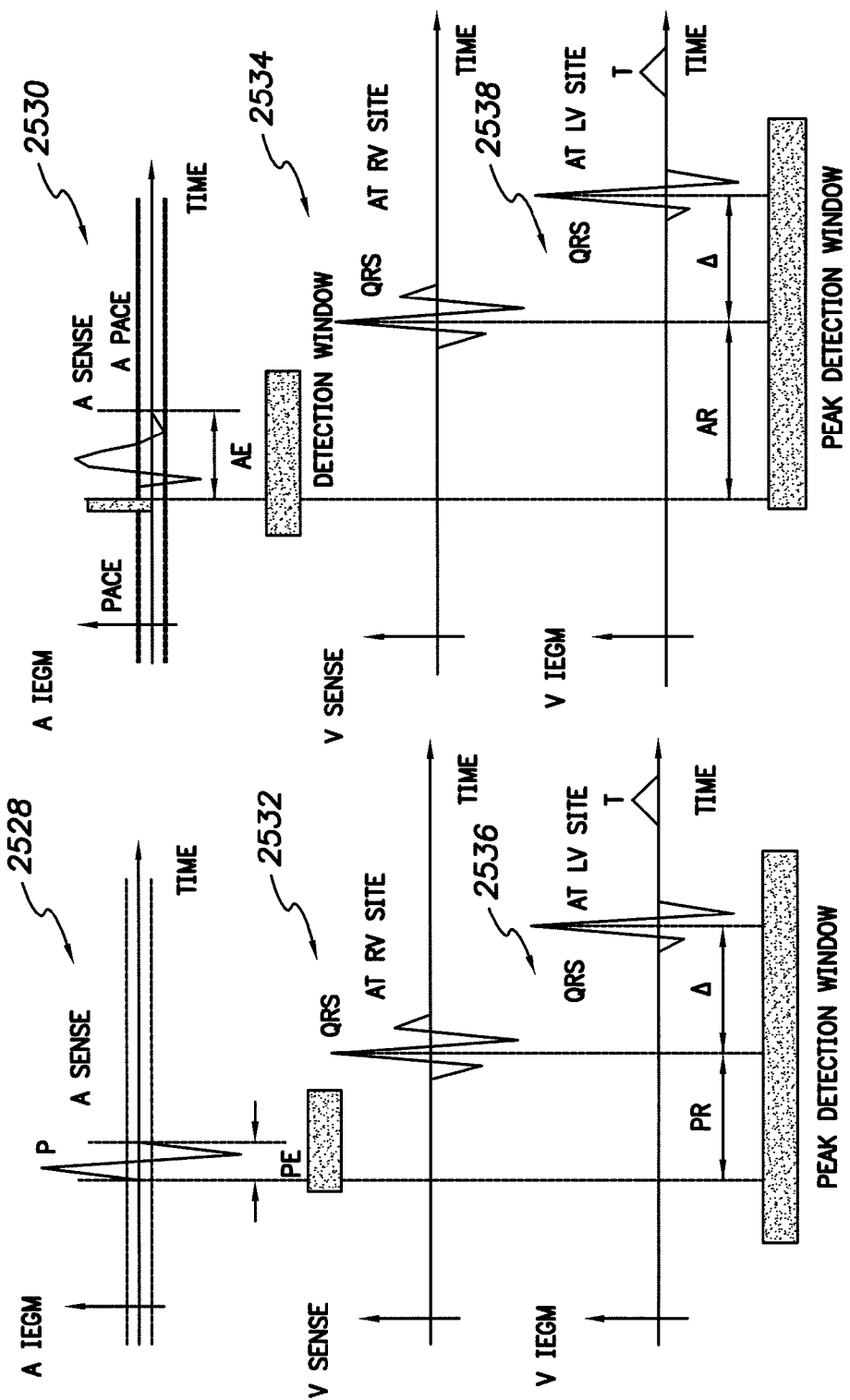
FIG. 29 is an exemplary graph summarizing a three-channel implementation.

FIG. 29 illustrates a three channel system set to sense an atrial IEGM and both LV and RV IEGMs. For each channel, two graphs are provided, one with atrial sensed event (i.e. a P-wave) and one with an atrial paced event (i.e. an atrial evoked response triggered by an A-pulse.) More specifically, graph 2528 shows a P-wave sensed on the atrial channel; whereas graph 2530 shows an atrial evoked response sensed on the atrial channel. Graph 2532 shows an RV QRS-complex subsequent to the P-wave, as sensed on the RV channel; whereas graph 2534 shows an RV QRS-complex subsequent to the atrial evoked response, as also sensed on the RV channel. Graph 2536 shows an LV QRS-complex following the RV QRS-complex, as sensed on the RV channel; whereas graph 2538 shows an LV QRS-complex following the RV QRS-complex, as also sensed on the LV channel.

FIG. 29 additionally illustrates some of the delay parameters the pace/ICD can measure, such as the PE and AE inter-atrial delays (which are measured on the atrial channel) and the intrinsic interventricular delay (Δ), which is measured on the LV channel. Also, as shown, the pacer/ICD can directly measure the PR conduction delay (i.e. the delay between the P-wave and the peak of the QRS-complex on the RV channel) or the AR conduction delay (i.e. the delay between the A-pulse and the peak of the QRS-complex on the RV channel.) [In other cases, the LV QRS-complex may appear first, in which case the PR/AR delays are measured from the atrial event to the peak of the LV QRS-complex.] The PR/AR conduction delays may also be exploited in the optimization of the AV/PV pacing delays (as described elsewhere in this patent application.) Note, also, that various other delay parameters (such as the ICVD terms or the PL terms) can also be measured using the three-channel signals of FIG. 29 or otherwise derived from the sensed signals. Thus, the three-channel implementation provides greater flexibility and efficiency as compared to the two-channel implementations.

Insofar as measuring the AE and PE delays are concerned, in some implementations, only one or the other are measured. For example, atrial pacing may be deactivated to ensure that all atrial beats are intrinsic. PE conduction delays are then measured, which are used to determine suitable PV pacing delays. Then, AV delays are derived from the PV values. Preferably, though, both AE and PE delays are measured and counted within the patient, as described in application Ser. No. 11/952,743, cited above. If a majority of atrial beats are paced, then AV delays are calculated from the measured AE delays (with PV delays then derived from the AV delays.) Conversely, if a majority of atrial beats are intrinsic, then PV delays are calculated from the measured PE delays (with AV delays then derived from the PV delays.) With that technique, no special atrial pacing procedures are required to accommodate patients wherein a majority of atrial events are paced. In any case, VV delays are preferably then used to specify separate pacing delays for the LV and RV.

The following sections address circumstances wherein the resulting pacing delays are longer than the intrinsic conduction delays to the LV and RV, as might result in patients with long inter-atrial conduction delays.

Pacing Regime Selection Techniques Where AV/PV Exceeds AR/PR

FIG. 30 provides an overview of the pacing regime selection techniques. Beginning at step 2600, the pacer/ICD determines the IACT value (or A-A value) of the patient using techniques already described with reference to FIGS. 24-29.) At step 2601, the pacer/ICD determines preferred or optimal AV/PV and VV pacing delays using, e.g., the rapid optimization techniques of FIGS. 24-29. Also, various techniques set forth in application Ser. No. 11/952,743, cited above may also be exploited, which use both atrial paced and atrial sensed beats to determine optimal AV/PV delays. At step 2602, the pacer/ICD measures or inputs atrio-ventricular conduction delays (AR/PR) within the patient. Preferably, AR/PR values are determined for both the left and right ventricles (i.e. $AR_{LV}/AR_{RV}$ and/or $PR_{LV}/PR_{RV}$). At step 2603, the pacer/ICD compares the atrio-ventricular pacing delays (AV/PV) with the measured atrio-ventricular conduction delay (AR/PR). That is, for atrial pacing, AV is compared to AR. For intrinsic atrial beats, PV is compared to PR. If separate AR/PR values have been determined for both the LV and RV, the pacer/ICD preferably used the minimum of $PR_{LV}$ and $PR_{RV}$ for comparison with PR (or the minimum of $AR_{LV}$ and $AR_{RV}$ for comparison with AV.)

At step 2604, if the atrio-ventricular pacing delay (AV/PV) is found to be less than the corresponding measured atrio-ventricular conduction delay (AR/PR), biventricular pacing is delivered using the preferred/optimal atrio-ventricular pacing delay (AV/PV) and the interventricular pacing delay (VV). That is, since AV/PV does not exceed AR/PR, there are no problems with delivering biventricular pacing using the values already determined for AV/PV and VV, as discussed above with reference to FIGS. 24-29.

However, if it is found, at step 2606, that the atrio-ventricular pacing delay (AV/PV) is not less than the corresponding atrio-ventricular conduction delay (AR/PR), an alternative pacing regime is selectively enabled that ensures AV/PV less than AR/PR. Suitable alternative pacing regimes include monoventricular pacing, biventricular pacing with negative hysteresis, or biventricular pacing with AV/PV delays reduced using predetermined offset values. The alternative regimes are provided, e.g., to ensure that the AV/PV pacing delays properly exceed the AV/AR conductions delays within the patient despite the long IACT of the patient. These alternative regimes, and the manner by which the device selects among them, will not be described with reference to FIG. 31.

Beginning at step 2700 of FIG. 31, the pacer/ICD determines AV/PV and VV delays via the rapid optimization techniques of FIGS. 24-29. In particular, the correction term (θ) shown in FIG. 28 is used while determining AV/PV and VV. At step 2702, the pacer/ICD measures the IACT (also called the A-A delay) for the patient, as already discussed. At step 2704, the pacer/ICD then compares PV to $PR_{MIN}$ for atrial sensed events (or AV to $AR_{MIN}$ for atrial paced events) to determine if $PV>PR_{MIN}$ (or $AV>AR_{MIN}$). $PR_{MIN}$ represents the minimum of $PR_{LV}$ and $PR_{RV}$ (i.e. the smaller or shorter of $PR_{LV}$ and $PR_{RV}$). Likewise, $AR_{MIN}$ represents the minimum of $AR_{LV}$ and $AR_{RV}$. If $PV>PR_{MIN}$ (or $AV>AR_{MIN}$), then biventricular pacing is delivered at step 2706 using AV/PV and VV, as discussed above. However, if not, then step 2708 is performed wherein the pacer/ICD begins to distinguish among the various alternative pacing regimes.

At step 2708, the pacer/ICD inputs predetermined threshold values for PR, (or AR for atrial paced beats), and IACT. The threshold value for PR is referred to herein as $PR_{MIN-TH}$ and may be, e.g., set in the range of 60 to 80 milliseconds (ms). (The threshold value for AR is referred to herein as $AR_{MIN-TH}$ and may be, e.g., set in the range of 80 to 100 ms.) The threshold value for IACT is referred to herein as $IACT_{TH}$ and may be, e.g., set in the range of 80 to 100 ms. If $PR_{MIN}>PR_{MIN-TH}$ (or $AR_{MIN}>AR_{MIN-TH}$) and $IACT<IACT_{TH}$, then either biventricular pacing with negative hysteresis or biventricular pacing with offsets is employed. If the pacer/ICD is equipped to perform either of these two pacing regimes, the pacer/ICD determines, at step 2710, which of the two regimes to employ by retrieving from memory a prior user selection (originally programmed into the device by a clinician or set to an initial default setting.) If offset pacing is selected, then the pacer/ICD, at step 2712, begins delivering biventricular pacing with offset-adjusted AV/PV values:

$$PV=PR-\text{OFFSET and}$$

$$AV=AR-\text{OFFSET}$$

where OFFSET is a preprogrammed values set, e.g., in the range of 10-40 ms. By using this offset, AV/PV can be set less than AR/PR. (If the initial offset is not sufficient to ensure that AV/PV<AR/PR, the offset can be increased.)

If negative hysteresis pacing is selected, then the pacer/ICD, at step 2714, instead begins delivering biventricular pacing with negative hysteresis. With negative hysteresis, the pacer/ICD tracks PR (or AR) and programs PV (or AV) delay to be shorter than PR (or AR.) Negative hysteresis is discussed in, e.g., U.S. Pat. No. 6,058,328 to Levine, et al., entitled "Implantable stimulation device having means for operating in a preemptive pacing mode to prevent tachyarrhythmias and method thereof." The negative hysteresis is set so as to reduce AV/PV below AR/PR.

Returning to step 2708, if either $PR_{MIN}\leq PR_{MIN-TH}$ (or $AR_{MIN}\leq AR_{MIN-TH}$ for atrial paced beats) or $IACT\geq IACT_{TH}$, then monoventricular pacing is considered at step 2716. That is, at step 2716, the pacer/ICD compares IACT against $PR_{MIN}$. If $IACT\leq PR_{MIN}$, monoventricular pacing is initiated with the chamber selected based on VV. If VV>0, then LV-only pacing is performed at step 2718 with $$PV_{LV}=PR-VV \text{ and}$$

$$AV_{LV}=AR-VV.$$

If $VV\leq 0$ then RV-only pacing is instead performed at step 2720 with $$PV_{RV}=PR+VV \text{ and}$$

$$AV_{RV}=AR+VV.$$

Hence, the condition "VV>0" indicates that the LV is pre-activated. The condition "VV<0" indicates that the RV is preactivated.

That is, so long as IACT is not too long (i.e. it is not longer than $PR_{MIN}$), monoventricular pacing is performed to address the situation where the calculated pacing delays are longer than measured conduction delays, as can occur within patients with long inter-atrial delays but otherwise normal atrio-ventricular conduction delays. In such patients, monoventricular pacing appears to provide a particularly effective pacing regime and helps prevent blood from being pumped back into the left atrium (LA) from the LV. If the IACT is too long (i.e. it is longer than $PR_{MIN}$), then the AV/PV and VV delays initially determined at step 2700 are not used. Rather, depending upon the programming of the device, other AV/V and VV delays may be employed, such as default values. Alternatively, warning signals can be generated to alert the clinician of the unique situation within the patient for manual programming of pacing parameters. For these patients, alternative procedures (i.e. other than the above-described rapid optimization techniques) may be appropriate for setting AV/PV and VV values within the patient.

To summarize, if AV/PV>AR/PR, then within patients with relatively normal PR or AR values (>=60-80 ms or >=80-100 ms & IACT<=80-100 ms), one of the following pacing regimes is exploited:

Negative Hysteresis: pacer/ICD tracks PR or AR and program PV or AV delay shorter than PR or AR.

Directly program pacer/ICD with PV=PR−offset or AR−offset; where offset=10-40 ms.

LV-only or RV-only pacing: Pre-activate the chamber with longer PR or AR by exploiting QuickOpt suggested PV or AV delay Within patients with comparatively short PR or AR (e.g. <60-80 ms or 80-100 ms) [and with AV/PV>AR/PR]:

If IACT is long (>80-100 ms), patient might required for other means of CRT optimization.

FIG. 32 illustrates pertinent components of an exemplary AA/AV/VV module 238' for use within the microcontroller of the pacer/ICD of FIG. 2 to implement the techniques of FIGS. 24-31. Briefly, the module includes an atrial pacing controller 2800 and a ventricular pacing controller 2802 for controlling the delivery of pacing pulses to the atria and ventricles, respectively. Among other functions, the ventricular pacing controller operates to determine the particular pacing regime to be performed, in accordance with the techniques of FIGS. 30-31.

An AR/PR conduction delay measuring unit 2804 measures conduction delays to the LV and RV for use in determining which pacing regime to employ or for other purposes. An inter-atrial conduction delay measuring unit 2806 measures AE and/or PE delays for use in determining IACT (i.e. A-A) or for other purposes. An intrinsic interventricular conduction delay determination unit 2808 and an intrinsic interventricular correction term determination unit 2810 determine the aforementioned Δ and ε values, respectively, which are exploited to determine VV. A conduction delay threshold input unit 2814 inputs suitable threshold values for use in implementations exploiting the techniques of FIG. 32 including $AR_{MIN-TH}$, $PR_{MIN-TH}$, $IACT_{TH}$.

An optimal AV/PV/VV pacing delay determination unit 2816 determines AV/PV/VV pacing delays based on information obtained by, e.g., units 2806, 2808, and 2810. The ventricular pacing controller uses this information along with the threshold values and the measured AR/PR and IACT values to determine the appropriate ventricular pacing regime. An AV/PV negative hysteresis controller 2818 is provided for applying negative hysteresis when appropriate. An AV/PV offset controller 2820 is provided for applying offsets to AV/PV values when appropriate. A monoventricular pacing controller 2822 is provided for controlling monoventricular pacing, when appropriate, and for selecting the particular chamber. Depending upon the implementation, the various components illustrated within FIG. 32 may be implemented as separate hardware or software modules. However, the modules may be combined so as to permit single modules to perform multiple functions.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method for controlling the delivery of cardiac pacing therapy using an implantable cardiac stimulation device, the method comprising:
    measuring an inter-atrial conduction time delay (IACT) and an atrio-ventricular conduction delay (AR/PR);
    determining an atrio-ventricular pacing delay (AV/PV) and an interventricular pacing delay (VV) for use in pacing the heart of the patient based, in part, on the measured inter-atrial conduction time delay (IACT);
    comparing the atrio-ventricular pacing delay (AV/PV) with the measured atrio-ventricular conduction delay (AR/PR);
    if the atrio-ventricular pacing delay (AV/PV) is less than the measured atrio-ventricular conduction delay (AR/PR), delivering biventricular pacing using the atrio-ventricular pacing delay (AV/PV) and the interventricular pacing delay (VV); and
    if the atrio-ventricular pacing delay (AV/PV) is not less than the corresponding atrio-ventricular conduction delay (AR/PR), selectively enabling an alternative pacing regime;
    wherein selectively enabling an alternative pacing regime includes selectively enabling one of monoventricular pacing, biventricular pacing with negative hysteresis, and biventricular pacing with AV/PV delays reduced using predetermined offset values;
    wherein selectively enabling monoventricular pacing includes:
    determining a minimum value ($PR_{MIN}/AR_{MIN}$) for the atrio-ventricular conduction delay (PR/AR) based on a comparison of AR/PR values measured for the left ventricle (LV) and the right ventricle (RV);
    comparing the minimum value ($PR_{MIN}/AR_{MIN}$) for the atrio-ventricular conduction delay against a predetermined minimum delay threshold ($PR_{MIN-TH}/AR_{MIN-TH}$) while also comparing the inter-atrial conduction delay (IACT) against a predetermined inter-atrial conduction delay threshold ($IACT_{TH}$); and
    selectively enabling monoventricular pacing if either the inter-atrial conduction delay (IACT) is greater than the inter-atrial delay threshold ($IACT_{TH}$) or if the minimum value ($PR_{MIN}/AR_{MIN}$) for the intrinsic atrio-ventricular pacing delay (IACT) is less than the predetermined minimum delay threshold ($PR_{MIN-TH}/AR_{MIN-TH}$).

2. The method of claim 1 wherein comparing the atrio-ventricular pacing delay (AV/PV) with the measured atrio-ventricular conduction delay (AR/PR) is performed to compare the atrio-ventricular pacing delay (AV/PV) with a minimum value ($PR_{MIN}/AR_{MIN}$) of the measured atrio-ventricular conduction delay (AR/PR) derived based on a comparison of atrio-ventricular conduction delay (AR/PR) values measured for the left ventricle (LV) and the right ventricle (RV).

3. The method of claim 1 wherein selectively enabling monoventricular pacing therapy further includes:
    comparing the inter-atrial conduction delay (IACT) to the minimum intrinsic atrio-ventricular conduction delay ($PR_{MIN}$); and
    enabling monoventricular pacing only if the inter-atrial conduction delay (IACT) does not exceed the minimum intrinsic atrio-ventricular conduction delay ($PR_{MIN}$).

4. The method of claim 3 wherein enabling monoventricular pacing therapy further includes:
    delivering monoventricular pacing to the left ventricle if VV>0; and
    delivering monoventricular pacing to the right ventricle if VV≦0.

5. The method of claim 1 wherein the implantable device is equipped to perform biventricular pacing with negative hysteresis and biventricular pacing with AV/PV delays reduced using predetermined offset values and wherein the device selects between the two based on a user selection.

6. A method for controlling the delivery of cardiac pacing therapy using an implantable cardiac stimulation device, the method comprising:
    measuring an inter-atrial conduction time delay (IACT) and an atrio-ventricular conduction delay (AR/PR);
    determining an atrio-ventricular pacing delay (AV/PV) and an interventricular pacing delay (VV) for use in pacing the heart of the patient based, in part, on the measured inter-atrial conduction time delay (IACT);
    comparing the atrio-ventricular pacing delay (AV/PV) with the measured atrio-ventricular conduction delay (AR/PR);
    if the atrio-ventricular pacing delay (AV/PV) is less than the measured atrio-ventricular conduction delay (AR/PR), delivering biventricular pacing using the atrio-ventricular pacing delay (AV/PV) and the interventricular pacing delay (VV); and
    if the atrio-ventricular pacing delay (AV/PV) is not less than the corresponding atrio-ventricular conduction delay (AR/PR), selectively enabling an alternative pacing regime;
    wherein selectively enabling an alternative pacing regime includes selectively enabling one of monoventricular pacing, biventricular pacing with negative hysteresis, and biventricular pacing with AV/PV delays reduced using predetermined offset values;
    wherein selectively enabling biventricular pacing with negative hysteresis includes:
    determining a minimum value ($PR_{MIN}/AR_{MIN}$) for the atrio-ventricular conduction delay (PR/AR) based on a comparison of AR/PR values measured for the left ventricle (LV) and the right ventricle (RV);
    comparing the minimum value ($PR_{MIN}/AR_{MIN}$) for the atrio-ventricular conduction delay against a predetermined minimum delay threshold ($PR_{MIN-TH}/AR_{MIN-TH}$) while also comparing the inter-atrial conduction delay (IACT) against a predetermined inter-atrial conduction delay threshold ($IACT_{TH}$); and
    selectively enabling biventricular pacing with negative hysteresis if the inter-atrial conduction delay (IACT) is less than the inter-atrial delay threshold ($IACT_{TH}$) and if the minimum value ($PR_{MIN}/AR_{MIN}$) for the intrinsic atrio-ventricular pacing delay (IACT) is greater than the predetermined minimum delay threshold ($PR_{MIN-TH}/AR_{MIN-TH}$).

7. A method for controlling the delivery of cardiac pacing therapy using an implantable cardiac stimulation device, the method comprising:

measuring an inter-atrial conduction time delay (IACT) and an atrio-ventricular conduction delay (AR/PR);

determining an atrio-ventricular pacing delay (AV/PV) and an interventricular pacing delay (VV) for use in pacing the heart of the patient based, in part, on the measured inter-atrial conduction time delay (IACT);

comparing the atrio-ventricular pacing delay (AV/PV) with the measured atrio-ventricular conduction delay (AR/PR);

if the atrio-ventricular pacing delay (AV/PV) is less than the measured atrio-ventricular conduction delay (AR/PR), delivering biventricular pacing using the atrio-ventricular pacing delay (AV/PV) and the interventricular pacing delay (VV); and if the atrio-ventricular pacing delay (AV/PV) is not less than the corresponding atrio-ventricular conduction delay (AR/PR), selectively enabling an alternative pacing regime;

wherein selectively enabling an alternative pacing regime includes selectively enabling one of monoventricular pacing, biventricular pacing with negative hysteresis, and biventricular pacing with AV/PV delays reduced using predetermined offset values;

wherein selectively enabling biventricular pacing with AV/PV delays reduced using predetermined offset values includes:

determining a minimum value ($PR_{MIN}/AR_{MIN}$) for the atrio-ventricular conduction delay (PR/AR) based on a comparison of AR/PR values measured for the left ventricle (LV) and the right ventricle (RV);

comparing the minimum value ($PR_{MIN}/AR_{MIN}$) for the atrio-ventricular conduction delay against a predetermined minimum delay threshold ($PR_{MIN-TH}/AR_{MIN-TH}$) while also comparing the inter-atrial conduction delay (IACT) against a predetermined inter-atrial conduction delay threshold ($IACT_{TH}$); and selectively enabling biventricular pacing with AV/PV delays reduced using predetermined offset values if the inter-atrial conduction delay (IACT) is less than the inter-atrial delay threshold ($IACT_{TH}$) and if the minimum value ($PR_{MIN}/AR_{MIN}$) for the intrinsic atrio-ventricular pacing delay (IACT) is greater than the predetermined minimum delay threshold ($PR_{MIN-TH}/AR_{MIN-TH}$).

8. The method of claim 7 wherein the offset values are in the range of 10-40 milliseconds (ms).

9. A method for controlling the delivering cardiac pacing therapy using an implantable cardiac stimulation device, the method comprising:

measuring an inter-atrial conduction time delay (IACT) and an atrio-ventricular conduction delay (AR/PR);

determining an atrio-ventricular pacing delay (AV/PV) and an interventricular pacing delay (VV) for use in pacing the heart of the patient based, in part, on the measured inter-atrial conduction time delay (IACT);

comparing the atrio-ventricular pacing delay (AV/PV) with the measured atrio-ventricular conduction delay (AR/PR);

if the atrio-ventricular pacing delay (AV/PV) is less than the measured atrio-ventricular conduction delay (AR/PR), delivering biventricular pacing using the atrio-ventricular pacing delay (AV/PV) and the interventricular pacing delay (VV); and if the atrio-ventricular pacing delay (AV/PV) is not less than the corresponding atrio-ventricular conduction delay (AR/PR), selectively enabling an alternative pacing regime;

wherein determining the atrio-ventricular pacing delay (AV/PV) and the interventricular pacing delay (VV) includes:

measuring inter-atrial conduction time (IACT) delays with the patient;

determining atrio-ventricular (AV/PV) pacing delays based on the measured inter-atrial conduction time (IACT) delays;

determining an intrinsic interventricular conduction delay ($\Delta$) and an interventricular correction term ($\epsilon$) for the patient; and determining an interventricular pacing delay (W) based on the intrinsic interventricular conduction delay ($\Delta$) and the interventricular correction term ($\epsilon$).

10. The method of claim 9 wherein determining the interventricular pacing delay (VV) based on the intrinsic interventricular conduction delay ($\Delta$) and the interventricular correction term ($\epsilon$) includes setting:

$VV=\alpha_1(\Delta+\epsilon)$, where $\alpha_1$ is a coefficient that is one of programmable or hard-coded within a range of values including 0.5.

11. The method of claim 9 wherein determining atrio-ventricular (AV/PV) pacing delays includes exploiting a correction factor $\theta$.

12. The method of claim 11 further including the step of measuring 9 within the patient based on interventricular delays.

13. The method of claim 12 wherein measuring $\theta$ within the patient includes:

if the interventricular pacing delay (VV) is greater than zero, measuring a time delay ($PL_{LV}$) from a paced event in the ventricles until the resulting left ventricular (LV) evoked response, then subtracting a baseline value to yield $\theta$; and if the interventricular pacing delay (VV) is not greater than zero, measuring a time delay ($PL_{RV}$) from a paced event in the ventricles until the resulting right ventricular (RV) evoked response, then subtracting the baseline value to yield $\theta$.

* * * * *